(12) United States Patent
Azouz et al.

(10) Patent No.: US 11,564,905 B2
(45) Date of Patent: *Jan. 31, 2023

(54) COMPOSITIONS AND METHODS FOR TREATING ALLERGIC INFLAMMATORY CONDITIONS

(71) Applicant: CHILDREN'S HOSPITAL MEDICAL CENTER, Cincinnati, OH (US)

(72) Inventors: Nurit P. Azouz, Cincinnati, OH (US); Marc E. Rothenberg, Cincinnati, OH (US)

(73) Assignee: CHILDREN'S HOSPITAL MEDICAL CENTER, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/946,984

(22) Filed: Jul. 14, 2020

(65) Prior Publication Data
US 2020/0338043 A1 Oct. 29, 2020

Related U.S. Application Data

(63) Continuation of application No. 16/069,412, filed as application No. PCT/US2016/068238 on Dec. 22, 2016, now Pat. No. 10,821,094.

(60) Provisional application No. 62/278,246, filed on Jan. 13, 2016.

(51) Int. Cl.
| | |
|---|---|
| A61K 38/55 | (2006.01) |
| A61K 38/57 | (2006.01) |
| A61K 31/37 | (2006.01) |
| A61K 31/711 | (2006.01) |
| A61P 37/08 | (2006.01) |
| A61K 31/7105 | (2006.01) |
| C12N 15/113 | (2010.01) |

(52) U.S. Cl.
CPC ............ *A61K 31/37* (2013.01); *A61K 31/711* (2013.01); *A61K 31/7105* (2013.01); *A61K 38/55* (2013.01); *A61K 38/57* (2013.01); *A61P 37/08* (2018.01); *C12N 15/113* (2013.01)

(58) Field of Classification Search
CPC .... A61K 31/352; A61K 38/005; A61K 38/55; A61K 38/57; A61K 39/3955; A61P 37/08
See application file for complete search history.

(56) References Cited

U.S. PATENT DOCUMENTS

| | | |
|---|---|---|
| 4,376,110 A | 3/1983 | David et al. |
| 4,522,811 A | 6/1985 | Eppstein et al. |
| 4,675,604 A | 6/1987 | Moyer et al. |
| 4,675,904 A | 6/1987 | Silverman |
| 5,148,483 A | 9/1992 | Silverman |
| 5,288,644 A | 2/1994 | Beavis et al. |
| 5,412,073 A | 5/1995 | Kalsheker et al. |
| 5,445,934 A | 8/1995 | Fodor et al. |
| 5,530,101 A | 6/1996 | Queen et al. |
| 5,700,637 A | 12/1997 | Southern |
| 5,744,305 A | 4/1998 | Fodor et al. |
| 5,888,510 A | 3/1999 | Kishimoto et al. |
| 5,945,334 A | 8/1999 | Besemer et al. |
| 5,976,081 A | 11/1999 | Silverman |
| 6,054,270 A | 4/2000 | Southern |
| 6,300,063 B1 | 10/2001 | Lipshutz et al. |
| 6,403,782 B1 | 6/2002 | Luster et al. |
| 6,429,027 B1 | 8/2002 | Chee et al. |
| 6,733,977 B2 | 5/2004 | Besemer et al. |
| 6,780,973 B1 | 8/2004 | Luster et al. |
| 6,825,350 B2 | 11/2004 | Crooks et al. |
| 6,858,394 B1 | 2/2005 | Chee et al. |
| 7,364,858 B2 | 4/2008 | Barany et al. |
| 7,514,209 B2 | 4/2009 | Dai et al. |
| 7,582,620 B2 | 9/2009 | Lew |
| 7,592,326 B2 | 9/2009 | Karaolis |
| 7,879,547 B2 | 2/2011 | Rothenberg et al. |
| 8,030,003 B2 | 10/2011 | Rothenberg |
| 8,409,565 B2 | 4/2013 | Levi-schaffer et al. |
| 9,260,756 B2 | 2/2016 | Rothenberg et al. |
| 9,345,763 B2 | 5/2016 | Rothenberg et al. |
| 9,517,238 B2 | 12/2016 | Rochman et al. |
| 9,624,545 B2 | 4/2017 | Rothenberg et al. |
| 9,691,411 B2 | 6/2017 | Scherer et al. |
| 9,803,244 B2 | 10/2017 | Rothenberg et al. |
| 9,928,344 B2 | 3/2018 | Rothenberg et al. |
| 9,982,303 B2 | 5/2018 | Rothenberg |
| 10,155,985 B2 | 12/2018 | Rothenberg et al. |

(Continued)

FOREIGN PATENT DOCUMENTS

| | | |
|---|---|---|
| CN | 101275941 A | 10/2008 |
| EP | 0619321 A1 | 10/1994 |

(Continued)

OTHER PUBLICATIONS

Goettig et al. Natural and synthetic inhibitors of kallikrein-related peptidases (KLKs). Biochimie. vol. 92, pp. 1546-1567. (Year: 2010).*

Michael et al. Biochemical and Enzymatic Characterization of Human Kallikrein 5 (hK5), a Novel Serine Protease Potentially Involved in Cancer Progression. The Journal of Biological Chemistry. Apr. 15, 2005, vol. 280, No. 15, pp. 14628-14635. (Year: 2005).*

Weber et al, Abstract-Characterization of the protease inhibitor SPINK7 in human skin, 41st Annual Meeting of the Arbeitsgemeinschaft Dermatolgische Forschung, Experiemental Dermatology, Mar. 13-15, 2014, vol. 23, pp. 1-52.

(Continued)

*Primary Examiner* — Jeffrey E. Russel
(74) *Attorney, Agent, or Firm* — KDB Firm PLLC

(57) ABSTRACT

The invention provides methods of treating an allergic inflammatory condition characterized by inflammation of the squamous epithelium of a target tissue by administering to the subject a pharmaceutical composition comprising a kallikrein 5 (KLK5) inhibitor, and a pharmaceutically acceptable carrier.

3 Claims, 20 Drawing Sheets

(56) References Cited

U.S. PATENT DOCUMENTS

| | | | |
|---|---|---|---|
| 10,294,517 B2 | 5/2019 | Rothenberg et al. | |
| 10,422,004 B2 | 9/2019 | Rothenberg et al. | |
| 10,821,094 B2* | 11/2020 | Azouz | A61K 31/37 |
| 2002/0077825 A1 | 6/2002 | Silverman et al. | |
| 2003/0078768 A1 | 4/2003 | Silverman et al. | |
| 2003/0157479 A1 | 8/2003 | Bachmann et al. | |
| 2003/0167189 A1 | 9/2003 | Lutgen et al. | |
| 2003/0194404 A1 | 10/2003 | Greenfeder et al. | |
| 2004/0033502 A1 | 2/2004 | Williams et al. | |
| 2004/0141951 A1 | 7/2004 | Rothenberg et al. | |
| 2005/0163764 A1 | 7/2005 | Medzhitov et al. | |
| 2007/0059720 A9 | 3/2007 | Fuqua et al. | |
| 2007/0233468 A1 | 10/2007 | Ozdas et al. | |
| 2007/0233498 A1 | 10/2007 | Silverman et al. | |
| 2008/0187908 A1 | 8/2008 | Adra | |
| 2008/0201280 A1 | 8/2008 | Martin et al. | |
| 2009/0233275 A1 | 9/2009 | Rothenberg | |
| 2009/0269774 A1 | 10/2009 | Rothenberg et al. | |
| 2010/0151472 A1 | 6/2010 | Mcgarrigle et al. | |
| 2010/0240965 A1 | 9/2010 | Furuta et al. | |
| 2010/0262603 A1 | 10/2010 | Odom et al. | |
| 2011/0123530 A1 | 5/2011 | Arron et al. | |
| 2011/0144183 A1 | 6/2011 | Paquet et al. | |
| 2011/0195500 A1 | 8/2011 | Rothenberg | |
| 2011/0301046 A1 | 12/2011 | Rothenberg et al. | |
| 2012/0004205 A1 | 1/2012 | Rothenberg | |
| 2012/0041911 A1 | 2/2012 | Pestian et al. | |
| 2012/0283117 A1 | 11/2012 | Rothenberg | |
| 2012/0288068 A1 | 11/2012 | Jaiswal et al. | |
| 2013/0035961 A1 | 2/2013 | Yegnanarayanan | |
| 2013/0065972 A1 | 3/2013 | Dent et al. | |
| 2013/0324435 A1 | 12/2013 | Rothenberg et al. | |
| 2014/0073801 A1 | 3/2014 | Storer et al. | |
| 2014/0113372 A1 | 4/2014 | Haque et al. | |
| 2014/0228301 A1 | 8/2014 | Meade et al. | |
| 2014/0228315 A1 | 8/2014 | Rothenberg et al. | |
| 2014/0286896 A1 | 9/2014 | Rothenberg et al. | |
| 2014/0328861 A1* | 11/2014 | Payton | A61K 31/573 424/158.1 |
| 2014/0343255 A1* | 11/2014 | Gonzalez | C07K 1/36 530/387.1 |
| 2015/0038552 A1 | 2/2015 | Rothenberg et al. | |
| 2015/0045334 A1 | 2/2015 | Rothenberg et al. | |
| 2015/0182499 A1 | 7/2015 | Rebound-Ravaux et al. | |
| 2015/0355180 A1 | 12/2015 | Resnick et al. | |
| 2016/0129012 A1 | 5/2016 | Rochman et al. | |
| 2016/0177394 A1 | 6/2016 | Rothenberg et al. | |
| 2016/0180041 A1 | 6/2016 | Pestian et al. | |
| 2016/0213681 A1* | 7/2016 | Santus | A61K 31/56 |
| 2016/0264658 A1 | 9/2016 | Ahmed et al. | |
| 2016/0304960 A1 | 10/2016 | Rothenberg | |
| 2016/0312282 A1 | 10/2016 | Rothenberg et al. | |
| 2017/0061073 A1 | 3/2017 | Sadhasivam | |
| 2017/0067111 A1 | 3/2017 | Rothenberg et al. | |
| 2017/0183719 A1 | 6/2017 | Rothenberg et al. | |
| 2017/0233813 A1 | 8/2017 | Rothenberg et al. | |
| 2019/0000799 A1 | 1/2019 | Azouz et al. | |
| 2019/0046444 A1 | 2/2019 | Konduri et al. | |
| 2021/0080453 A1 | 3/2021 | Rothenberg et al. | |

FOREIGN PATENT DOCUMENTS

| | | |
|---|---|---|
| EP | 0619321 B1 | 1/1999 |
| EP | 0949271 A1 | 10/1999 |
| WO | 8910977 A1 | 11/1989 |
| WO | 9937319 A1 | 7/1999 |
| WO | 2005007175 A2 | 1/2005 |
| WO | 2005033134 A2 | 4/2005 |
| WO | 2005106492 A2 | 11/2005 |
| WO | 2005106492 A3 | 5/2006 |
| WO | 2006083390 A2 | 8/2006 |
| WO | 2006119343 A1 | 11/2006 |
| WO | 2006083390 A3 | 12/2006 |
| WO | 2009015434 A1 | 2/2009 |
| WO | 2009018493 A1 | 2/2009 |
| WO | 2009061819 A1 | 5/2009 |
| WO | 2009089062 A2 | 7/2009 |
| WO | 2009089062 A3 | 9/2009 |
| WO | 2009089062 A8 | 9/2010 |
| WO | 2010126867 A1 | 11/2010 |
| WO | 2012025765 A1 | 3/2012 |
| WO | 2012094643 A2 | 7/2012 |
| WO | 2012094643 A3 | 11/2012 |
| WO | 2012174549 A2 | 12/2012 |
| WO | 2012177945 A2 | 12/2012 |
| WO | 2012178188 A2 | 12/2012 |
| WO | 2012174549 A9 | 2/2013 |
| WO | 2012177945 A3 | 2/2013 |
| WO | 2013082308 A1 | 6/2013 |
| WO | 2012178188 A3 | 7/2013 |
| WO | 2013126834 A1 | 8/2013 |
| WO | 2013155010 A1 | 10/2013 |
| WO | 2014059178 A1 | 4/2014 |
| WO | 2014190269 A1 | 11/2014 |
| WO | 2015017731 A1 | 2/2015 |
| WO | 2015127379 A1 | 8/2015 |
| WO | 2015142739 A1 | 9/2015 |
| WO | 2016023026 A1 | 2/2016 |
| WO | 2016196146 A1 | 12/2016 |
| WO | 2017123401 A1 | 7/2017 |
| WO | 2019204580 A1 | 10/2019 |

OTHER PUBLICATIONS

International Search Report and Written Opinion of the International Searching Authority dated Mar. 27, 2017 for International Application No. PCT/US2016/068238, filed Dec. 22, 2016, 8 pages.

Azouz, N. et al., (2016). "Loss of SPINK7 in esophageal epithelial cells unleashes a pro-inflammatory response characterized by excessive cytokine production and loss of barrier function." J. Allergy Clin. Immunol. 137(2) Suppl. p. AB280#915. 1 page.

Azouz, N. et al., (Jun. 6, 2018). "The antiprotease SPINK7 serves as an inhibitory checkpoint for esophageal epithelial inflammatory responses." Sci. Transl. Med. 10(444): doi:10.1126/scitranslmed. aap9736. 29 pages.

Valeska, H. et al., (May 2019). "Wheat amylase/trypsin inhibitors aggravate eosinophilic esophagitis." Gastroenterol. 156(6, Suppl. 1) S619. 1 page.

Von Arnim, U. et al., (2014). "Eosinophilic esophagitis-treatment of eosinophil esophagitis with drugs: corticosteroids." Digestive Diseases 32:126-129.

Extended European Search Report dated Jul. 23, 2019 for International Application No. PCT/US2016/068238, filed Dec. 22, 2016, 15 pages.

Liesveld, "Hypereosinophilic Syndrome". Dec. 2018, Merck Manual Professional Version (5 pages). (Year: 2018).

Rahaghi et al. Long-term clinical outcomes following treatment with alpha 1-proteinase inhibitor for COPD associated with alpha-1 antitrypsin deficiency: a look at the evidence. Respiratory Research. 2017, vol. 18:105 (9 pages).—(Year: 2017).

Spergel et al. Treatment of eosinophilic esophagitis with specific food elimination diet directed by a combination of skin prick and patch tests. Annals of Allergy, Asthma & Immunology. Oct. 2005, vol. 95, pp. 336-343 (Year: 2005).

Smith et al. Serine proteases, their inhibitors and allergy. Allergy 2006: 61: 1441-1447 (Year: 2006) (7 pages).

Azouz et al. Functional role of kallikrein 5 and proteinase-activated receptor 2 in eosinophilic esophagitis. Science Translational Medicine, vol. 12, Issue 545, (Year: 2020) (May 27, 2020) (15 pages).

Gonsalves et al. Diagnosis and treatment of eosinophilic esophagitis. J Allergy Clin Immunol. Jan. 2020. (Year: 2020) (7 pages).

Rank et al. Technical review on the management of eosinophilic esophagitis: a report from the AGA institute and the joint task force on allergy-immunology practice parameters. Annals of Allergy, Asthma & Immunology, vol. 124, Issue 5, May 2020, pp. 424-440 (Year: 2020) (34 pages).

Furuta et al. (Oct. 2007) "Eosinophilic Esophagitis in Children and Adults: A Systematic Review and Consensus Recommendations for Diagnosis and Treatment", Gastroenterology, 133(4):1342-1363.

(56) References Cited

OTHER PUBLICATIONS

Garbacki et al. (Jan. 28, 2011) "MicroRNAs Profiling in Murine Models of Acute and Chronic Asthma: A Relationship with mRNAs Targets", PLoS One, e16509, 6(1):23 pages.
Garcia-Echeverria et al. (Apr. 2004) "In Vivo Antitumor Activity of NVP-AEW541—A Novel, Potent, and Selective Inhibitor of the IGF-IR Kinase", Cancer Cell, 5(3):231-239.
Garçon et al. (Aug. 1, 2011) "Development of an AS04-adjuvanted HPV Vaccine with the Adjuvant System Approach", BioDrugs, 25(4):217-226.
Garrett et al. (Jan. 2004) "Anti-interleukin-5 (Mepolizumab) Therapy for Hypereosinophilic Syndrome", Journal of Allergy and Clinical Immunology, 113(1):115-119.
Kihara et al. (Sep. 1, 2001) "Prediction of Sensitivity of Esophageal Tumors to Adjuvant Chemotherapy by cDNA Microarray Analysis of Gene-expression Profiles", Cancer Research, 61(17):6474-6479.
Kim et al. (2004) "Microarray Applications in Cancer Research", Cancer Research and Treatment, 36(4):207-213.
Kim et al. (Dec. 2004) "Rebound Eosinophilia after Treatment of Hypereosinophilic Syndrome and Eosinophilic Gastroenteritis with Monoclonal Anti-IL-5 Antibody SCH55700", The Journal of Allergy and Clinical Immunology, 114(6):1449-1455.
Georgantas et al. (Feb. 20, 2007) "CD34+ Hematopoietic Stem-progenitor Cell MicroRNA Expression and Function: A Circuit Diagram of Differentiation Control", Proceedings of the National Academy of Sciences of the United States of America, 104(8):2750-2755.
Gilbert et al. (Aug. 1978) "Effects of Acute Endotoxemia and Glucose Administration on Circulating Leukocyte Populations in Normal and Diabetic Subjects", Metabolism, 27(8):889-899.
Gong et al. (May 30, 2013) "Gene polymorphisms of OPRM1 A118G and ABCB1 C3435T may influence opioid requirements in Chinese patients with cancer pain", Asian Pacific Journal of Cancer Prevention, 14(5):2937-2943.
Gonsalves et al. (Sep. 2006) "Histopathologic Variability and Endoscopic Correlates in Adults with Eosinophilic Esophagitis", Gastrointestinal Endoscopy, 64(3):313-319.
Griffiths-Jones et al. (2006) "miRBase: MicroRNA Sequences, Targets and Gene Nomenclature", Nucleic Acids Research, 34:D140-D144.
Griffiths-Jones et al. (Jan. 2008) "miRBase: Tools for Micro RNA Genomics", Nucleic Acids Research, 36 (Database issue):D154-D158.
Gupta et al. (Jan. 2006) "Cytokine Expression in Normal and Inflamed Esophageal Mucosa: A Study into the Pathogenesis of Allergic Eosinophilic Esophagitis", Journal of Pediatric Gastroenterology and Nutrition, 42(1):22-26.
Gupta et al. (May 1998) "Expression of Inducible Nitric Oxide Synthase (iNOS) mRNA in Inflamed Esophageal and Colonic Mucosa in a Pediatric Population", American Journal of Gastroenterology, 93(5):795-798.
Guyon et al. (Jan. 2002) "Gene Selection for Cancer Classification using Support Vector Machines", Machine Learning, 46:389-422.
Hahn et al. (Apr. 2006) "Airway Epithelial Cells Produce Neurotrophins and Promote the Survival of Eosinophils During Allergic Airway Inflammation", Journal of Allergy and Clinical Immunology, 117(4):787-794.
Hamilton et al. (1980) "Regulation of the Plasminogen Activator Activity of Macrophage Tumor Cell Lines", International Journal of Immunopharmacology, 2(4):353-362.
Hamoui et al. (Aug. 2004) "Increased Acid Exposure in Patients With Gastroesophageal Reflux Disease Influences Cyclooxygenase-2 Gene Expression in the Squamous Epithelium of the Lower Esophagus", Archives of Surgery, 139(7):712-716.
Hardiman Gary (Nov. 5, 2004) "Microarray Platforms—Comparisons and Contrasts", Pharmacogenomics, 5(5):487-502.
Hatley et al. (Sep. 14, 2010) "Modulation of K-Ras-dependent Lung Tumorigenesis by MicroRNA-21", Cancer Cell, 18(3):282-293.
Hennessy et al. (Apr. 2010) "Targeting Toll-Like Receptors: Emerging Therapeutics?", Nature Reviews Drug Discovery, 9(4):293-307.
Himes et al. (Mar. 4, 2009) "Prediction of Chronic Obstructive Pulmonary Disease (COPD) in Asthma Patients Using Electronic Medical Records", Journal of the American Medical Informatics Association, 16(3):371-379.
Hogan et al. (May 2008) "Eosinophils: Biological Properties and Role in Health and Disease", Clinical & Experimental Allergy, 38(5):709-750.
Hogan et al. (Dec. 2004) "The Eosinophil as a Therapeutic Target in Gastrointestinal Disease", Alimentary Pharmacology and Therapeutics, 20(11-12):1231-1240.
Hotchkiss et al. (Jun. 1, 2001) "Sepsis-induced Apoptosis Causes Progressive Profound Depletion of B and CD4+ T Lymphocytes in Humans", Journal of Immunology, 166(11):6952-6963.
Huang et al. (Jul. 1, 2006) "RegRNA: An Integrated Web Server for Identifying Regulatory RNA Motifs and Elements", Nucleic Acids Research, 34:W429-W434.
Hwang et al. (Apr. 30, 2005) "Expression of IL-17 Homologs and their Receptors in the Synovial Cells of Rheumatoid Arthritis Patients", Molecular Cell, 19(2):180-184.
Indo Y. (Dec. 2001) "Molecular Basis of Congenital Insensitivity to Pain with Anhidrosis (CIPA): Mutations and Polymorphisms in TRKA (NTRK1) Gene Encoding the Receptor Tyrosine Kinase for Nerve Growth Factor", Human Mutation, 18(6):462-471.
Indo et al. (Aug. 1996) "Mutations in the TRKA/NGF Receptor Gene in Patients with Congenital Insensitivity to Pain with Anhidrosis", Nature Genetics, 13(4):485-488.
Indo Y. (Oct. 2012) "Nerve Growth Factor and the Physiology of Pain: Lessons from Congenital Insensitivity to Pain with Anhidrosis", Clinical Genetics, 82(4):341-350.
Ip et al. (Dec. 2007) "Interleukin-31 Induces Cytokine and Chemokine Production from Human Bronchial Epithelial Cells through Activation of Mitogen-activated Protein Kinase Signalling Pathways: Implications for the Allergic Response", Immunology, 122(4):532-541.
Iwasaki et al. (Jun. 20, 2005) "Identification of Eosinophil Lineage-committed Progenitors in the Murine Bone Marrow", Journal of Experimental Medicine, 201(12):1891-1897.
Jacobsen et al. (Jun. 2007) "Eosinophils: Singularly Destructive Effector Cells or Purveyors of Immunoregulation?", The Journal of Allergy and Clinical Immunology, 119(6):1313-1320.
Jakiela et al. (Oct. 2009) "Intrinsic Pathway of Apoptosis in Peripheral Blood Eosinophils of Churg-strauss Syndrome", Rheumatology (Oxford), 48(10):1202-1207.
Jia et al. (Nov. 2008) "Mist1 Regulates Pancreatic Acinar Cell Proliferation through p21 CIP1/WAF1", Gastroenterology, 135(5):1687-1697.
Jiang et al. (Jul. 2011) "The Emerging Role of MicroRNAs in Asthma", Molecular and Cellular Biochemistry, 353(1-2):35-40.
Juffali et al. (2010) "The WiNAM project: Neural data analysis with applications to epilespy", Biomedical Circuits and Systems Conference, 45-48.
Junttila et al. (Oct. 27, 2008) "Tuning Sensitivity to IL-4 and IL-13: Differential Expression of IL-4Ralpha, IL-13Ralpha1, and Gammac Regulates Relative Cytokine Sensitivity", Journal of Experimental Medicine, 205(11):2595-2608.
Kaiko et al. (Feb. 2011) "New Insights into the Generation of Th2 Immunity and Potential Therapeutic Targets for the Treatment of Asthma", Current Opinion in Allergy and Clinical Immunology, 11(1):39-45.
Kaimal et al. (Jul. 2010) "Toppcluster: A Multiple Gene List Feature Analyzer for Comparative Enrichment Clustering and Network-based Dissection of Biological System", Nucleic Acids Research, 38:W96-W102.
Kanzler et al. (May 3, 2007) "Therapeutic Targeting of Innate Immunity with Toll-like Receptor Agonists and Antagonists", Nature Medicine, 13(5):552-559.
Kariyawasam et al. (Sep. 2009) "Activin and Transforming Growth Factor-β Signaling Pathways are Activated after Allergen Challenge in Mild Asthma", The Journal of Allergy and Clinical Immunology, 124(3):454-462.
Kaur et al. (Jul. 1, 2002) "Rofecoxib Inhibits Cyclooxygenase 2 Expression and Activity and Reduces Cell Proliferation in Barrett's Esophagus", Gastroenterology, 123(1):60-67.

(56) References Cited

OTHER PUBLICATIONS

Kelly et al. (Apr. 9, 2012) "More codeine fatalities after tonsillectomy in North American children", Pediatrics, 129(5):e1343-1347.
Kerstjens et al. (Oct. 2019) "Airway Pharmacology: Treatment Options and Algorithms to Treat Patients with Chronic Obstructive Pulmonary Disease", Journal of Thoracic Disease, 11(S17):S2200-S2209.
Kihara et al., "Prediction of Sensitivity of Esophageal Tumors to Adjuvant Chemotherapy by cDNA Microarray Analysis of Gene-expression Profiles", Cancer Research, Sep. 1, 2001, 61(17):6474-6479.
Kim et al., "Microarray Applications in Cancer Research", Cancer Research and Treatment, 2004, 36(4):207-213.
Kim et al., "Rebound Eosinophilia after Treatment of Hypereosinophilic Syndrome and Eosinophilic Gastroenteritis with Monoclonal Anti-IL-5 Antibody SCH55700", The Journal of Allergy and Clinical Immunology, Dec. 2004, 114(6):1449-1455.
Chen et al. (Jul. 1, 2009) "ToppGene Suite for Gene List Enrichment Analysis and Candidate Gene Prioritization", Nucleic Acids Research, 37(Suppl. 2):W305-W311.
Cheverud Jamesm. (Jul. 2001) "A Simple Correction for Multiple Comparisons in Interval Mapping Genome Scans", Heredity, 87(Pt 1):52-58.
Cho et al. (Mar. 24, 2006) "Role of Early Growth Response-1 (Egr-1) in Interleukin-13-induced Inflammation and Remodeling", Journal of Biological Chemistry, 281(12):8161-8168.
Chu et al. (Jan. 9, 2011) "Eosinophils are Required for the Maintenance of Plasma Cells in the Bone Marrow", Nature Immunology, 12(2):151-159.
Clavijo et al. (Mar. 12, 2011) "A sensitive assay for the quantification of morphine and its active metabolites in human plasma and dried blood spots using high-performance liquid chromatography-tandem mass spectrometry", Analytical and Bioanalytical Chemistry, 400(3):715-728.
Cohen et al. (Aug. 2012) "Pharmacogenetics in perioperative medicine", Current opinion in anaesthesiology, 25(4):419-427.
Collins et al. (Jun. 2008) "Clinical, Pathologic, and Molecular Characterization of Familial Eosinophilic Esophagitis Compared With Sporadic Cases", Clinical Gastroenterology and Hepatology, 6(6):621-629.
Collins et al. (Mar. 2017) "Newly Developed and Validated Eosinophilic Esophagitis Histology Scoring System and Evidence that it Outperforms Peak Eosinophil Count for Disease Diagnosis and Monitoring", Diseases of the Esophagus, 30(3):1-8.
Collins et al. (Oct. 2005) "Online Selection of Discriminative Tracking Features", IEEE Transactions on Pattern Analysis and Machine Intelligence, 27(10):1631-1643.
Collison et al. (Jul. 2011) "Inhibition of House Dust Mite-induced Allergic Airways Disease by Antagonism of MicroRNA-145 is Comparable to Glucocorticoid Treatment", The Journal of Allergy and Clinical Immunology, e4, 128(1):160-167.
Corren et al. (Sep. 22, 2011) "Lebrikizumab Treatment in Adults with Asthma", The New England Journal of Medicine, 365(12):1088-1098.
Crews et al. (Jan. 29, 2014) "Clinical Pharmacogenetics Implementation Consortium Guidelines for Cytochrome P450 2d6 Genotype and Codeine Therapy", Clinical Pharmacology & Therapeutics, 95(4):376-382.
Czajkowsky et al. (Oct. 2012) "Fc-fusion Proteins: New Developments and Future Prospectives", EMBO Molecular Medicine, 4(10):1015-1028.
D'Agostini et al. (Jul. 2005) "Antitumour Effect of Om-174 and Cyclophosphamide on Murine B16 Melanoma in Different Experimental Conditions", International Immunopharmacology, 5(7-8):1205-1212.
Dalal et al. (Oct. 31, 1997) "Molecular Characterization of Neurotrophin Expression and the Corresponding Tropomyosin Receptor Kinases (trks) in Epithelial and Stromal Cells of the Human Prostate", Molecular and Cellular Endocrinology, 134(1):15-22.

Davis Carla M. (Feb. 11, 2011) "Diagnosis and Treatment of Eosinophilic Gastrointestinal Disorders", Pediatric Allergy, Immunology, and Pulmonology, 23(4):237-242.
De Bruin et al. (Oct. 7, 2010) "Eosinophil Differentiation in the Bone Marrow is Inhibited by T Cell-derived IFN-γ ", Blood, 116(14):2559-2569.
Debrosse et al. (Jul. 2010) "Identification, Epidemiology and Chronicity of Pediatric Esophageal Eosinophilia from 1982-1999", The Journal of Allergy and Clinical Immunology, 126(1):112-119.
Dellon et al. (Oct. 22, 2013) "Clinical and Endoscopic Characteristics do not Reliably Differentiate PP I-responsive Esophageal Eosinophilia and Eosinophilic Esophagitis in Patients undergoing Upper Endoscopy: A Prospective Cohort Study", The American Journal of Gastroenterology, 108(12):1854-1860.
Dellon (Jul. 2012) "Eosinophilic Esophagitis: Diagnostic Tests and Criteria", Current Opinion in Gastroenterology, 28(4):382-388.
Dellon et al. (May 1, 2014) "Immunohistochemical Evidence of Inflammation Is Similar in Patients with Eosinophilic Esophagitis and PPI-Responsive Esophageal Eosinophilia: A Prospective Cohort Study", Gastroenterology, 146(5):S17.
Dellon et al. (Feb. 2011) "Tryptase Staining of Mast Cells may Differentiate Eosinophilic Esophagitis from Gastroesophageal Reflux Disease", The American Journal of Gastroenterology, 106(2):264-271.
Dent et al. (Nov. 1, 1990) "Eosinophilia in Transgenic Mice Expressing Interleukin 5", Journal of Experimental Medicine, 172(5):1425-1431.
Descamps et al. (Jul. 2005) "Expression of Nerve Growth Factor Receptors and their Prognostic Value in Human Breast Cancer", Oncology Reports, 14(1):161-171.
Dewson et al. (Oct. 1, 2001) "Interleukin-5 Inhibits Translocation of Bax to the Mitochondria, Cytochrome C Release, and Activation of Caspases in Human Eosinophil", Blood, 98(7):2239-2247.
Dohrman et al. (Aug. 1997) "Ethanol Reduces Expression of the Nerve Growth Factor Receptor, but not Nerve Growth Factor Protein Levels in the Neonatal Rat Cerebellum", Alcoholism: Clinical and Experimental Research, 21(5):882-893.
Donato et al. (Jan. 1, 2002) "Human HTm4 is a Hematopoietic Cell Cycle Regulator", Journal of Clinical Investigation, 109(1):51-58.
Driss et al. (Apr. 2, 2009) "TLR2-dependent Eosinophil Interactions with Mycobacteria: Role of Alpha-defensins", Blood, 113(14):3235-3244.
Dyer et al. (Sep. 15, 2008) "Functionally Competent Eosinophils Differentiated Ex Vivo in High Purity From Normal Mouse Bone Marrow", Journal of Immunology, 181(6):4004-4009.
Dyer et al. (Jan. 1, 2009) "Generation of Eosinophils from Unselected Bone Marrow Progenitors: Wild-type, TLR- and Eosinophil-deficient Mice", The Open Immunology Journal, 2:163-167.
Dyer et al. (Jun. 1, 2010) "Mouse and Human Eosinophils De Granulate in Response to Platelet-activating Factor (PAF) and C21 LysoPAF Via A PAF receptor-independent Mechanism: Evidence for a Novel Receptor", Journal of Immunology, 184(11):6327-6334.
Dyer et al. (Sep. 24, 2009) "Pneumoviruses Infect Eosinophils and Elicit MyD88-dependent Release of Chemoattractant Cytokines and Interleukin-6", Blood, 114(13):2649-2656.
Ehlers et al. (1991) "Differentiation of T Cell Lymphokine Gene Expression: The in Vitro Acquisition of T Cell Memory", Journal of Experimental Medicine, 173(1):25-36.
Eissing et al. (Feb. 1, 2012) "Pharmacogenomics of Codeine, Morphine, and Morphine-6-Glucuronide: Model-Based Analysis of the Influence of CYP2D6 Activity, UGT2B7 Activity, Renal Impairment, and CYP3A4 Inhibition", Molecular Diagnosis & Therapy, 16(1):43-53.
Elsner (Nov. 1992) "The CC Chemokine Antagonist Met-RANTES Inhibits Eosinophil Effector Functions through the Chemokine Receptors CCR1 and CCR3", European Journal of Immunology, 27(11):2892-2998.
Fulkerson et al. (Feb. 2013) "Targeting Eosinophils in Allergy, Inflammation and Beyond", Nature Reviews Drug Discovery, 12(2):117-129.
Fahy et al. (Nov. 15, 2001) "Remodeling of the Airway Epithelium in Asthma", American Journal of Respiratory and Critical Care Medicine, 164(10 Pt2):S46-S51.

(56) References Cited

OTHER PUBLICATIONS

Fardet et al. (Jan. 22, 2006) "Severe Strongyloidiasis in Corticosteroid-treated Patients: Case Series and Literature Review", Journal of Infection, 54(1):18-27.
Faubion Jr. et al. (Jul. 1998) "Treatment of Eosinophilic Esophagitis with Inhaled Corticosteroids", Journal of Pediatric Gastroenterology and Nutrition, 27(1):90-93.
Festuccia et al. (Jan. 2007) "Tyrosine Kinase Inhibitor CEP-701 Blocks the NTRK1/NGF Receptor and Limits the Invasive Capability of Prostate Cancer Cells in Vitro", International Journal of Oncology, 30(1):193-200.
Flower et al. (Nov. 16, 1999) "Modelling G-protein-coupled Receptors for Drug Design", Biochimica et Biophysica Acta, 1422(3):207-234.
Fox et al. (Aug. 2002) "Eosinophilic Esophagitis: It's Not Just Kid's Stuff", Gastrointestinal Endoscopy, 56(2):260-270.
Freund-Michel et al. (Jan. 2008) "The Nerve Growth Factor and its Receptors in Airway Inflammatory Diseases", Pharmacology & Therapeutics, 117(1):52-76.
Frossard et al. (Oct. 1, 2004) "Nerve Growth Factor and its Receptors in Asthma and Inflammation", European Journal of Pharmacology, 500(1-3):453-465.
Fuentebella et al. (Sep. 2010) "Increased Number of Regulatory T Cells in Esophageal Tissue of Patients with Eosinophilic Esophagitis in Comparison to Gastro Esophageal Reflux Disease and Control Groups", Journal of Pediatric Gastroenterology and Nutrition, 51(3):283-589.
Fukada et al. (Jul. 2013) "OCT1 Genetic Variants Influence the Pharmacokinetics of Morphine in Children", Pharmacogenomics, 14(10):1141-1151.
Fukao (Jun. 2007) "An Evolutionarily Conserved Mechanism for MicroRNA-223 Expression Revealed by MicroRNA Gene Profiling", Cell, 129(3):617-631.
Fukuda et al. (Feb. 2013) "Oral Session II-A (OII-A) Special Populations 3:45 pm-4:45 pm", Clinical Pharmacology & Therapeutics, 93:S49-S51.
Fulkerson et al. (Oct. 31, 2006) "A Central Regulatory Role for Eosinophils and the Eotaxin/CCR3 Axis in Chronic Experimental Allergic Airway Inflammation", Proceedings of the National Academy of Sciences of the United States of America, 103(44):16418-16423.
Fulkerson et al., "A Central Regulatory Role for Eosinophils and the Eotaxin/CCR3 Axis in Chronic Experimental Allergic Airway Inflammation", Proceedings of the National Academy of Sciences of the United States of America, Oct. 31, 2006, 103(44):16418-16423.
Phipps et al. (Sep. 1, 2007) "Eosinophils Contribute to Innate Antiviral Immunity and Promote Clearance of Respiratory Syncytial Virus", Blood, 110(5):1578-1586.
Plötz et al. (Jan. 1, 2001) "The Interaction of Human Peripheral Blood Eosinophils with Bacterial Lipopolysaccharide is CD14 Dependent", Blood, 97(1):235-241.
Polikepahad et al. (Sep. 24, 2010) "Proinflammatory Role for let-7 MicroRNAS in Experimental Asthma", Journal of Biological Chemistry, 285(39):30139-30149.
Pouladi et al. (Jan. 2004) "Interleukin-13-dependent Expression of Matrix Metalloproteinase-12 is Required for the Development of Airway Eosinophilia in Mice", American Journal of Respiratory Cell and Molecular Biology, 30(1):84-90.
Proudfoot et al. (Nov. 5, 1999) "Amino-terminally Modified RANTES Analogues Demonstrate Differential Effects on RANTES Receptors", Journal of Biological Chemistry, 274(45):32478-32485.
Prows et al. (Nov. 13, 2013) "Codeine-related Adverse Drug Reactions in Children Following Tonsillectomy: A Prospective Study", Laryngoscope, 124(5):1242-1250.
Prussin et al. (Dec. 2009) "Eosinophilic Gastrointestinal Disease and Peanut Allergy are Alternatively Associated with IL-5+ and IL-5(−) T(H)2 Responses", The Journal of Allergy and Clinical Immunology, 124(6):1326-1332.

Shah et al. (Mar. 2009) "Histopathologic Variability in Children with Eosinophilic Esophagitis", The American Journal of Gastroenterology, 104(3):716-721.
Sharma et al. (Aug. 5, 2011) "Protein Kinase R as Mediator of the Effects of Interferon (IFN) Gamma and Tumor Necrosis Factor (TNF) Alpha on Normal and Dysplastic Hematopoiesis", Journal of Biological Chemistry, 286(31):27506-27514.
Raap et al. (Feb. 2010) "The Role of Neurotrophins in the Pathophysiology of Allergic Rhinitis", Current Opinion in Allergy and Clinical Immunology, 10(1):8-13.
Rabinowits et al. (Jan. 2009) "Exosomal microRNA: a Diagnostic Marker for Lung Cancer", Clinical Lung Cancer, 10(1):42-46.
Ramirez et al. (Dec. 15, 2004) "Cell and Tumor Biology Immortalization of Human Bronchial Epithelial Cells in the Absence of Viral Oncoproteins", Cancer Research, 64(24):9027-9034.
Ramirez et al. (Aug. 2006) "Transcriptional Regulation of the Human α2(I) Collagen Gene (COL1A2), an Informative Model System to Study Fibrotic Diseases", Matrix Biology, 25(6):365-372.
Ray et al. (May 16, 2011) "Human Mu Opioid Receptor (OPRM1 A 118G) Polymorphism is Associated with Brain Mu-opioid Receptor Binding Potential in Smokers", PNAS, 108(22):9268-9273.
Raychaudhuri et al. (2000) "Principal Components Analysis to Summarize Microarray Experiments: Application to Sporulation Time Series", Pacific Symposium on Biocomputing, 5:452-463.
Robinson et al. (Jan. 1999) "CD34(+)/Interleukin-5Ralpha Messenger RNA+ Cells in the Bronchial Mucosa in Asthma: Potential Airway Eosinophil Progenitors", American Journal of Respiratory Cell and Molecular Biology, 20(1):9-13.
Rochman et al. (Jun. 1, 2007) "Cutting Edge: Direct Action of Thymic Stromal Lymphopoietin on Activated Human CD4+ T cells", The Journal of Immunology, 178(11):6720-6724.
Rochman et al. (Jul. 2015) "Neurotrophic Tyrosine Kinase Receptor 1 is a Direct Transcriptional and Epigenetic Target of IL-13 Involved in Allergic Inflammation", Immunology, 8(4):785-798.
Rodrigo et al. (Feb. 2008) "High Intraepithelial Eosinophil Counts in Esophageal Squamous Epithelium Are Not Specific for Eosinophilic Esophagitis in Adults", The American Journal of Gastroenterology, vol. 103, Issue 2, Feb. 2008, 103(2);435-442.
Romani et al. (Jul. 9, 2002) "Cluster Analysis of Gene Expression Dynamics", Proceedings of the National Academy of Sciences, 99(14):9121-9126.
Rosas et al. (Jul. 2006) "IL-5-mediated Eosinophil Survival Requires Inhibition of GSK-3 and Correlates with β-catenin Relocalization", Journal of Leukocyte Biology, 80(1):186-195.
Rothenberg Marc E. (Oct. 2009) "Biology and Treatment of Eosinophilic Esophagitis", Gastroenterology, 137(4):1238-1249.
Rothenberg et al. (Apr. 2010) "Common Variants at 5q22 Associate with Pediatric Eosinophilic Esophagitis", Nature Genetics, 42(4):289-291.
Rothenberg et al. (Jan. 2004) "Eosinophilic Gastrointestinal Disorders (EGID)", The Journal of Allergy and Clinical Immunologythe Journal of Allergy and Clinical Immunology, 113(1):11-28.
Rothenberg (Apr. 21, 2016) "Humanized anti-IL-5 Antibody Therapy", Cell, 165(3):1 page.
Rothenberg et al. (Dec. 2001) "Pathogenesis and Clinical Features of Eosinophilic Esophagitis", The Journal of Allergy and Clinical Immunology, 108(6):891-894.
Rothenberg et al. (Apr. 2010) "The Eosinophil", Annual Review of Immunology, 24:147-174.
Rothenberg et al. (Mar. 20, 2008) "Treatment of Patients with the Hypereosinophilic Syndrome with Mepolizumab", The New England Journal of Medicine, 358(12):1215-1228.
Russ et al. (2013) "T Cell Immunity as a Tool for Studying Epigenetic Regulation of Cellular Differentiation", Frontiers in Genetics, 4:218.
Sabroe et al. (Aug. 25, 2000) "A Small Molecule Antagonist of Chemokine Receptors CCR1 and CCR3", The Journal of Biological Chemistry, 275(34):25985-25992.
Sabroe et al. (May 1, 2002) "Toll-Like Receptor (TLR)2 and TLR4 in Human Peripheral Blood Granulocytes: A Critical Role for Monocytes in Leukocyte Lipopolysaccharide Responses", The Journal of Immunology, 168(9):4701-4710.

(56) References Cited

OTHER PUBLICATIONS

Sadhasivam et al. (2014) "Genetics of Pain Perception, COMT and Postoperative Pain Management in Children", The Pharmacogenomics Journal, 15(3):277-284.

Sadhasivam et al. (Jul.-Aug. 2012) "Morphine Clearance in Children: Does Race or Genetics Matter?", Journal of Opioid Management, 8(4):217-226.

Sadhasivam et al. (2015) "Novel Associations between FAAH Genetic Varients an Postoperative Central Opioid Related Adverse Effects", The Pharmacogenomics Journal, 15(5):436-442.

Sadhasivam et al. (Jun. 13, 2012) "Preventing Opioid-Related Deaths in Children Undergoing Surgery", Pain Medicine, 13(7):982-983.

Sadhasivam et al. (Apr. 23, 2012) "Race and Unequal Burden of Perioperative Pain and Opioid Related Adverse Effects in Children", Pediatrics, 129(5):832-838.

Saeki et al. (Mar. 2, 2001) "Identification of a Potent and Nonpeptidyl CCR3 Antagonist", Biochemical and Biophysical Research Communications, 281(3):779-782.

Saini et al. (Nov. 27, 2008) "Annotation of Mammalian Primary microRNAs", BMC Genomics, Article No. 564, 9(1):19 pages.

Saito et al. (Mar. 15, 2002) "Pathogenesis of Murine Experimental Allergic Rhinitis: A Study of Local and Systemic Consequences of IL-5 Deficiency", The Journal of Immunology, 168(6):3017-3023.

Sato et al. (May 2011) "MicroRNAs and Epigenetics", The FEBS Journal, 278(10):1598-1609.

Sayed et al. (Jul. 2011) "MicroRNAs in Development and Disease", Physiological Reviews, 91(3):827-887.

Scherer et al. (2013) "Investigating the Speech Characteristics of Suicidal Adolescents", International Conference on Acoustics, Speech and Signal Processing, 5 pages.

Schmid-Grendelmeier et al. (Jul. 15, 2002) "Eosinophils Express Functional IL-13 in Eosinophilic Inflammatory Diseases", Journal of Immunology, 169(2):1021-1027.

Schoneberg et al. (Mar. 2, 2018) "Structural Basis of G Protein-coupled Receptor Function", Molecular and Cellular Endocrinology, 151(1-2):181-193.

Schultz et al. (May 26, 1998) "SMART, a Simple Modular Architecture Research Tool: Identification of Signaling Domains", Proceedings of the National Academy of Sciences of the United States of America, 95(11):5857-5864.

Sehmi et al. (Nov. 15, 1997) "Allergen-induced Increases in IL-5 Receptor Alpha-subunit Expression on Bone Marrow-derived CD34+ Cells from Asthmatic Subjects. A Novel Marker of Progenitor Cell Commitment Towards Eosinophilic Differentiation", Journal of Clinical Investigation, 100(10):2466-2475.

Sexton et al. (Sep. 2009) "Recent Advances in our Understanding of Peptide Hormone Receptors and RAMPS", Current Opinion in Drug Discovery & Development, 2(5):440-448.

Shaaban et al. (Dec. 2010) "Eosinopenia: Is it a Good Marker of Sepsis in Comparison to Procalcitonin and C-reactive Protein Levels for Patients Admitted to a Critical Care Unit in an Urban Hospital?", Journal of Critical Care, 25(4):570-575.

Schultz et al., "SMART, a Simple Modular Architecture Research Tool: Identification of Signaling Domains", Proceedings of the National Academy of Sciences of the United States of America, May 26, 1998, 95(11):5857-5864.

Sehmi et al., "Allergen-induced Increases in IL-5 Receptor Alpha-subunit Expression on Bone Mariow-derived CD34+ Cells from Asthmatic Subjects. A Novel Marker of Progenitor Cell Commitment Towards Eosinophilic Differentiation", Journal of Clinical Investigation, Nov. 15, 1997, 100(10):2466-2475.

Kledal et al. (Sep. 12, 1997) "A Broad-Spectrum Chemokine Antagonist Encoded by Kaposi's Sarcoma-Associated Herpesvirus", Science, 277(5332):1656-1659.

Klingelhofer et al. (Nov. 2002) "Dynamic Interplay Between Adhesive and Lateral E-Cadherin Dimers", Molecular and Cellular Biology, 22(21):7449-7458.

Komiya et al. (Oct. 2003) "Concerted Expression of Eotaxin-1, Eotaxin-2, and Eotaxin-3 in Human Bronchial Epithelial Cells", Cellular Immunology, 225(2):91-100.

Kong et al. (Jan. 2012) "MicroRNA-375 Inhibits Tumour Growth and Metastasis in Oesophageal Squamous Cell Carcinoma Through Repressing Insulin-like Growth Factor 1 Receptor", Gut, 61(1):33-42.

Konikoff et al. (Nov. 2006) "A Randomized, Double-blind, Placebo-controlled Trial of Fluticasone Propionate for Pediatric Eosinophilic Esophagitis", Gastroenterology, 131(5):1381-1391.

Konturek et al. (Aug. 2004) "Activation of NFκB Represents the Central Event in the Neoplastic Progression Associated with Barrett's Esophagus: A Possible Link to the Inflammation and Overexpression of COX-2, PPARγ and Growth Factors", Digestive Diseases and Sciences, 49(7-8):1075-1083.

Kottyan et al. (Jul. 13, 2014) "Genome-wide Association Analysis of Eosinophilic Esophagitis Provides Insight into the Tissue Specificity of this Allergic Disease", Nature Genetics, 46(8):895-900.

Kouro et al. (Dec. 2009) "IL-5- and Eosinophil-mediated Inflammation: From Discovery to Therapy", International Immunology, 21(12):1303-1309.

Krichevsky et al. (Jan. 2009) "MIR-21: A Small Multi-faceted RNA", Journal of Cellular and Molecular Medicine, 13(1):39-53.

Krutzfeldt et al. (Dec. 1, 2005) "Silencing of MicroRNAs in Vivo with 'Antagomirs'", Nature, 438(7068):685-689.

Kumar et al. (Nov. 2011) "Let-7 microRNA-mediated Regulation of IL-13 and Allergic Airway Inflammation", The Journal of Allergy and Clinical Immunology, e10, 128(5):1077-1085.

Kuperman et al. (Aug. 2002) "Direct Effects of Interleukin-13 on Epithelial Cells Cause Airway Hyperreactivity and Mucus Overproduction in Asthma", Nature Medicine, 8(8):885-889.

Kuperman et al. (Mar. 16, 1998) "Signal Transducer and Activator of Transcription Factor 6 (Stat6)-deficient Mice are Protected from Antigen-induced Airway Hyperresponsiveness and Mucus Production", Journal of Experimental Medicine, 187(6):939-948.

Laprise et al. (Mar. 23, 2004) "Functional Classes of Bronchial Mucosa Genes that are Differentially Expressed in Asthma", BMC Genomics, 5(1):10 pages.

Lavigne et al. (Nov. 12, 2004) "Human Bronchial Epithelial Cells Express and Secrete MMP-12", Biochemical and Biophysical Research Communications, 324(2):534-546.

Lee et al. (Apr. 2010) "Eosinophils in Health And Disease: The LIAR Hypothesis", Clinical & Experimental Allergy, 40(4):563-575.

Lee et al. (Jan. 2006) "ERK1/2 Mitogen-activated Protein Kinase Selectively Mediates IL-13-induced Lung Inflammation and Remodeling in Vivo", Journal of Clinical Investigation, 116(1):163-173.

Lee et al. (Oct. 2001) "Interleukin-13 Induces Dramatically Different Transcriptional Programs in Three Human Airway Cell Types", American Journal of Respiratory Cell and Molecular, 25(4):474-485.

Lei et al. (Mar. 2007) "Transcriptional Regulation of Trk Family Neurotrophin Receptors", Cellular and Molecular Life Sciences, 64(5):522-532.

Leigh et al. (Apr. 1, 2004) "Type 2 Cytokines in the Pathogenesis of Sustained Airway Dysfunction and Airway Remodeling in Mice", American Journal of Respiratory and Critical Care Medicine, 169(7):860-867.

Leschziner et al. (Sep. 12, 2006) "ABCB1 Genotype and PGP Expression, Function and Therapeutic Drug Response: A Critical Review and Recommendations for Future Research", The Pharmacogenomics Journal, 7(3):154-179.

Letunic et al. (Jan. 2012) "SMART 7: Recent Updates to the Protein Domain Annotation Resource", Nucleic Acids Research, 40:D302-D305.

Levi-Montalcini R. (Sep. 4, 1987) "The Nerve Growth Factor 35 Years Late", Science, 237(4819):1154-1162.

Lexmond et al. (Aug. 2013) "Elevated Levels Of leukotriene C4 Synthase mRNA Distinguish a Subpopulation of Eosinophilic Oesophagitis Patients", Clinical & Experimental Allergy, 43(8):902-913.

(56) References Cited

OTHER PUBLICATIONS

Li et al. (Oct. 2011) "Epigenetic Silencing of microRNA-375 Regulates PDKI Expression in Esophageal Cancer", Digestive Diseases and Sciences, 56(10):2849-2856.
Li et al. (Mar. 31, 2011) "miR-223 Regulates Migration and Invasion by Targeting Artemin in Human Esophageal Carcinoma", Journal of Biomedical Science, 18(1):9 pages.
Liacouras et al. (Jul. 2011) "Eosinophilic Esophagitis: Updated Consensus Recommendations for Children and Adults", Journal of Allergy and Clinical Immunology, 128(1):3-26.
Liacouras et al. (Sep. 2007) "Summary of the First International Gastrointestinal Eosinophil Research Symposium", Journal of Pediatric Gastroenterology and Nutrition, 45(3):370-391.
Lim et al. (Jan. 1, 2014) "Demethylation of the Human Eotaxin-3 Gene Promoter Leads to the Elevated Expression of Eotaxin-3", Journal of Immunology, 192(1):466-474.
Lim et al. (Apr. 15, 2011) "Epigenetic Regulation of the IL-13-induced Human Eotaxin-3 Gene by CREB-binding Protein-mediated Histone 3 Acetylation", Journal of Biological Chemistry, 286(15):13193-13204.
Lin et al. (Mar. 31, 2011) "miR-142-3p as a Potential Prognostic Biomarker for Esophageal Squamous Cell Carcinoma", Journal of Surgical Oncology, 105(2):175-182.
Linch et al. (Nov. 2009) "Mouse Eosinophils Possess Potent Antibacterial Properties in Vivo", Infection and Immunity, 77(11):4976-4982.
Linch et al. (Jun. 2011) "The Role of Eosinophils in Non-parasitic Infections", Endocrine, Metabolic & Immune Disorders—Drug Targets, 11(2):165-172.
Lipkin Stefanien (Apr. 1979) "Eosinophil Counts in Bacteremia", Archives of Internal Medicine, 139(4):490-491.
Liu et al. (Feb. 2012) "Role of microRNA let-7 and Effect to HMGA2 in Esophageal Squamous Cell Carcinoma", Molecular Biology Reports, 39(2):1239-1246.
Livak et al. (2001) "Analysis of Relative Gene Expression Data using Real-Time Quantitative PCR and the 2-Delta DeltaCT Method", Methods, 25:402-408.
Lo et al. (Dec. 16, 2011) "Identification of a Novel Mouse p53 Target Gene DDA3", Oncogene, 18(54):7765-7774.
Long et al. (Jun. 1, 2002) "Disruption of the NAD(P)H:quinone Oxidoreductase 1 (NQO1) Gene in Mice Causes Myelogenous Hyperplasia", Cancer Research, 62(11):3030-3036.
Lovinsky-Desir et al. (Jun. 2012) "Epigenetics, Asthma, and Allergic Diseases: A Review of the Latest Advancements", Current Allergy and Asthma Reports, 12(3):211-220.
Lu et al. (2013) "Diagnostic, Functional, and Therapeutic Roles of microRNA in Allergic Diseases", Journal of Allergy and Clinical Immunology, 132(1):3-13.
Lu et al. (Sep. 17, 2010) "Function of miR-146a in Controlling Treg Cell-mediated Regulation of Th1 Responses", Cell, 142(6):914-929.
Lu et al. (Jul. 16, 2012) "MicroRNA Profiling in Mucosal Biopsies of Eosinophilic Esophagitis Patients Pre and Post Treatment with Steroids and Relationship with mRNA Targets", PLoS One, e40676, 7(7):11 pages.
Lu et al. (Apr. 15, 2009) "MicroRNA-21 is Up-Regulated in Allergic Airway Inflammation and Regulates IL-12p35 Expression", Journal of Immunology, 182(8):4994-5002.
Lu et al. (Sep. 15, 2011) "MicroRNA-21 Limits in Vivo Immune Response-mediated Activation of the IL-12/IFN-gamma Pathway, Th1 Polarization, and the Severity of Delayed-type Hypersensitivity", Journal of Immunology, 187(16):3362-3373.
Lu et al. (Apr. 2012) "MicroRNA signature in Patients with Eosinophilic Esophagitis, Reversibility with Glucocorticoids, and Assessment as Disease Biomarkers", The Journal of Allergy and Clinical Immunology, e9, 129(4):1064-1075.
Lu et al. (Feb. 15, 2013) "miR-223 Deficiency Increases Eosinophil Progenitor Proliferation", Journal of Immunology, 190(4):1576-1582.

Lu et al. (Jul. 2012) "MiR-375 is Downregulated in Epithelial Cells after IL-13 Stimulation and Regulates an IL-13-induced Epithelial Transcriptome", Mucosal Immunology, 5(4):388-396.
Lu et al. (Mar. 22, 2013) "Targeted Ablation of miR-21 Decreases Murine Eosinophil Progenitor Cell Growth", PLoS One, e59397, 8(3):8 pages.
Lucendo et al. (Jun. 15, 2011) "Montelukast Was Inefficient in Maintaining Steroid-Induced Remission in Adult Eosinophilic Esophagitis", Digestive Diseases and Sciences, 56(12):3551-3558.
Lucendo et al. (Sep. 2008) "Treatment with Topical Steroids Downregulates IL-5, Eotaxin-1/CCL11, and Eotaxin-3/CCL26 Gene Expression in Eosinophilic Esophagitis", The American Journal of Gastroenterology, 103(9):2184-2193.
Accession No. E-MEXP-3298, (May 2, 2014).
Accession No. E-MEXP-3345, (Jun. 3, 2014).
Accession No. E-MEXP-3346, (Jun. 3, 2014).
Accession No. E-MEXP-3350, (Feb. 6, 2013).
Accession No. E-MEXP-3351, (Sep. 10, 2014).
Accession No. E-MEXP-3353, (May 2, 2014).
(Oct. 10, 2017) Asthma and Immunology, American College of Allergy.
(Oct. 10, 2017) Eosinophilic Esophagitis, American College of Gastroenterology.
European Patent Organisation, Office Action, mailed in counterpart European Patent Application No. 12732079.4, dated Apr. 22, 2014, 11 pages.
Extended European Search Report for EP Application No. 15828951. 2, dated Nov. 16, 2017, 8 pages.
Extended European Search Report dated Feb. 13, 2015 for European Application No. EP12802640, filed on Dec. 27, 2012.
Extended European Search Report dated Oct. 4, 2018 for International Application No. PCT/US2016/034185, filed May 25, 2016, 8 pages.
International Preliminary Report on Patentability received for PCT International Application No. PCT/US16/68238, dated Jul. 26, 2018, 7 pages.
International Search Report and Written Opinion of the International Searching Authority dated Jul. 8, 2019 for International Application No. PCT/US2019/028076, dated Apr. 18, 2019, 15 pages.
International Search Report for PCT Application No. PCT/US2006/016948, filed May 3, 2006, 1 page.
International search report issued in PCT/US2015/020768, dated Jun. 12, 2015.
International Search Report dated Dec. 27, 2012 for International Application No. PCT/US2012/043640, filed Jun. 21, 2012.
International Search Report dated Mar. 25, 2013 for International Application No. PCT/US2012/044061, filed Jun. 25, 2012.
International Search Report dated Sep. 9, 2016 for International Application No. PCT/US2016/034185, filed May 25, 2016, 4 pages.
International Search Report received for PCT Patent International Application No. PCT/US2014/039357, dated Sep. 24, 2014, 8 pages.
International Search Report received for PCT Patent International Application No. PCT/US2014/049301, dated Dec. 8, 2014, 8 pages.
International Search Report received for PCT Patent International Application No. PCT/US2015/017134, dated May 6, 2015, 11 pages.
International Search Report and Written Opinion received in connection with PCT/US2005/044456, filed Dec. 7, 2006, dated Sep. 11, 2006, 18 pages.
Mus Musculus TaqMan Probe Mm00446968_m1 for Hypoxanthine Guanine Phosphoribosyl Transferase (Hprt).
Mus musculus TaqMan probe Mm01216172_m1 for chemokine (C-C motif) receptor 3 (Ccr3).
Anonymous (Jul. 7, 2015) "TaqMan(R) Human Micro RNA Arrays", 2 pages.
Anthony et al. (Sep. 2012) "Response to Imatinib Mesylate in Patients with Hypereosinophilic Syndrome", International Journal of Hematology, 96(3):320-326.
April et al. (Dec. 3, 2009) "Whole-Genome Gene Expression Profiling of Formalin-Fixed, Paraffin-Embedded Tissue Samples", Plos One, e8162, 4(12):10 pages.

(56) References Cited

OTHER PUBLICATIONS

Armour et al. (Mar. 31, 2010) "Expression of Human FcγRllla as a GPI-linked Molecule on CHO Cells to Enable Measurement of Human IgG Binding", Journal of Immunological Methods, 354(1-2):20-33.

Arroyo et al. (Mar. 22, 2011) "Argonaute2 Complexes Carry a Population of Circulating MicroRNAs Independent of Vesicles in Human Plasma", Proceedings of the National Academy of Sciences of the United States of America, 108(12):5003-5008.

Assa'ad et al. (Nov. 2011) "An Antibody Against IL-5 Reduces Numbers of Esophageal Intraepithelial Eosinophils in Children With Eosinophilic Esophagitis", Gastroenterology, 141(5):1593-1604.

Abidi et al. (2008) "Eosinopenia is a Reliable Marker of Sepsis on Admission to Medical Intensive Care Units", Critical Care, R59, 12(2):10 pages.

Abonia et al. (2012) "Eosinophilic Esophagitis: Rapidly Advancing Insights", Annual Review of Medicine, 63:421-434.

Abonia et al. (Jul. 2010) "Involvement of Mast Cells in Eosinophilic Esophagitis", The Journal of Allergy and Clinical Immunology, 126(1):140-149.

Aceves et al. (Jan. 2007) "Esophageal Remodeling in Pediatric Eosinophilic Esophagitis", The Journal of Allergy and Clinical Immunology, 119(1):206-212.

Aceves et al. (Dec. 2010) "Mast Cells Infiltrate the Esophageal Smooth Muscle in Patients with Eosinophilic Esophagitis, Express TGF-β1, and Increase Esophageal Smooth Muscle Contraction", The Journal of Allergy and Clinical Immunology, e4, 126(6):1198-204.

Ackerman et al. (Apr. 26, 2002) "Charcot-Leyden Crystal Protein (Galectin-10) Is Not a Dual Function Galectin with Lysophospholipase Activity but Binds a Lysophospholipase Inhibitor in a Novel Structural Fashion", Journal of Biological Chemistry, 277(17):14859-14868.

Adachi et al. (Dec. 15, 2007) "Transduction of Phosphatase and Tensin Homolog Deleted on Chromosome 10 into Eosinophils Attenuates Survival, Chemotaxis, and Airway Inflammation", The Journal of Immunology, 179(12):8105-8111.

Akuthota et al. (2011) "Eosinophils: Offenders or General Bystanders in Allergic Airway Disease and Pulmonary Immunity?", Journal of Innate Immunity, 3(2):113-119.

Alexander Jeffreya. (May 2014) "Topical Steroid Therapy for Eosinophilic Esophagitis", Gastroenterology & Hepatology, 10(5):327-329.

Allakhverdi et al. (Feb. 2009) "CD34+ Hemopoietic Progenitor Cells are Potent Effectors of Allergic Inflammation", Journal of Allergy and Clinical Immunology, 123(2):472-478.

Anderson et al. (Sep. 2011) "Evaluation of a morphine maturation model for the prediction of morphine clearance in children", British Journal of Clinical Pharmacology, 72(3):518-520.

Andrews "Allosteric Small Molecule Inhibitors of the NGF/TrkA Pathway a New Approach to Treating Inflammatory Pain", Available at: http://www.arraybiopharma.com/files/6313/9810/8021/PubAttachment587.pdf, 33 pages.

Angus et al. (Jul. 2009) "Epidemiology of Severe Sepsis in the United States: Analysis of Incidence, Outcome, and Associated Costs of Care", Critical Care Medicine, 29(7):1303-1310.

Assa'ad et al., "Pediatric Patients With Eosinophilic Esophagitis: An 8-year Follow-up", The Journal of Allergy and Clinical Immunology, Mar. 2007, 119(3):731-738.

Attwood et al., "Esophageal Eosinophilia with Dysphagia. A Distinct Clinicopathologic Syndrome", Digestive Diseases and Sciences, Jan. 1993, 38(1):109-116.

Aune et al., "Epigenetics and T helper 1 Differentiation", Immunology, Mar. 2009, 126(3):299-305.

Ayala et al., "Differential Induction of Apoptosis in Lymphoid Tissues during Sepsis: Variation in Onset, Frequency, and the Nature of the Mediators", Blood, May 15, 1996, 87(10):4261-4275.

Baker et al., "The Central Role of Receiver Operating Characteristic (ROC) Curves in Evaluating Tests for the Early Detection of Cancer", Journal of the National Cancer Institute, Apr. 2, 2003, 95(7):511-515.

Baldrick et al., "Pollinex Quattro Ragweed: Safety Evaluation of a New Allergy Vaccine Adjuvanted with Monophosphoryl Lipid a (MPL) for the Treatment of Ragweed Pollen Allergy", Journal of Applied Toxicology, Jul.-Aug. 2007, 27(4):399-409.

Van Rooij et al. (Feb. 3, 2012) "Developing microRNA Therapeutics", Circulation Research, 110(3):496-507.

Vandepapeliere et al. (Jan. 14, 2008) "Vaccine Adjuvant Systems Containing Monophosphoryl Lipid A and QS21 Induce Strong C63 and Persistent Humoral and T Cell Responses Against Hepatitis B Surface Antigen in Healthy Adult Volunteers", Vaccine, 33(8):1084-1091.

Varnes et al. (Apr. 5, 2004) "Discovery of N-propylurea 3-benzylpiperidines as Selective CC Chemokine Receptor-3 (CCR3) Antagonists", Bioorganic & Medicinal Chemistry Letters, 14(7):1645-1649.

Velasco et al. (Mar. 2005) "Toll-like Receptor 4 or 2 Agonists Decrease Allergic Inflammation", American Journal of Respiratory Cell and Molecular Biology, 32(3):218-224.

Velu et al. (May 7, 2009) "Gfi1 Regulates miR-21 and miR-196b to Control Myelopoiesis", Blood, 113(19):4720-4728.

Venek et al. (2014) "Adolescent Suicidal Risk Assessment in Clinician-Patient Interaction: A Study of Verbal and Acoustic Behaviors", Spoken Language Technology Workshop, 6 pages.

Venge Per (May 2010) "The Eosinophil and Airway Remodelling in Asthma", The Clinical Respiratory Journal, 4 (Suppl 1):15-19.

Venkatasubramanian et al. (Jul. 2014) "ABCC3 and OCT1 genotypes influence pharmacokinetics of morphine in children", Pharmacogenomics, 15(10):1297-1309.

Verspoor et al. (Jun. 15, 2009) "The textual characteristics of traditional and Open Access scientific journals are similar", BMC Bioinformatics, 10:183.

Vicario et al. (Jan. 2010) "Local B Cells and IgE Production in the Oesophageal Mucosa in Eosinophilic Oesophagitis", Gut, 59(1):12-20.

Vincent et al. (Dec. 2, 2009) "International Study of the Prevalence and Outcomes of Infection in Intensive Care Units", JAMA, 302(21):2323-2329.

Von Ahlfen et al. (2007) "Determinants of RNA Quality from FFPE Samples", PLoS One, e1261, 2(12): 7 pages.

Wacker et al. (Jul. 8, 2002) "CCR3 Antagonists: A Potential New Therapy for the Treatment of Asthma. Discovery and Structure-activity Relationships", Bioorganic & Medicinal Chemistry Letters, 12(13):1785-1789.

Wan et al. (Feb. 2004) "Foxa2 Regulates Alveolarization and Goblet Cell Hyperplasia", Development, 131(4):953-964.

Wang et al. (May 2010) "Differential Functions of Growth Factor Receptor-Bound Protein 7 (GRB7) and Its Variant GRB7v in Ovarian Carcinogenesis", Clinical Cancer Research, 16(9):2529-2539.

Wang et al. (May 15, 1994) "Sepsis-induced Apoptosis of the Thymocytes in Mice", Journal of Immunology, 152(10):5014-5021.

Wechsler et al. (Jul. 2018) "Esophagitis Reference Score Accurately Identifies Disease Activity and Treatment Effects in Children", Clinical Gastroenterology and Hepatology, 16(7):1056-1063.

Wen et al. (Aug. 23, 2013) "Molecular diagnosis of eosinophilic esophagitis by gene expression profiling", Gastroenterology, 145(6):19 Pages.

Wen et al. (Oct. 19, 2014) "Transcriptome analysis of proton pump inhibitor-responsive esophageal eosinophilia reveals proton pump inhibitor-reversible allergic inflammation", Journal of Allergy and Clinical Immunology, 135(1):187-197.

White (Nov. 24, 2000) "Identification of Potent, Selective Non-peptide CC Chemokine Receptor-3 Antagonist that Inhibits Eotaxin-, Eotaxin-2-, and Monocyte Chemotactic Protein-4-induced Eosinophil Migration", The Journal of Biological Chemistry, 275(47):36626-36631.

Wills-Karp Marsha (Dec. 2004) "Interleukin-13 in Asthma Pathogenesis", Immunological Reviews, 202:175-190.

(56) References Cited

OTHER PUBLICATIONS

Winter et al. (Mar. 2009) "Many Roads to Maturity: microRNA Biogenesis Pathways and their Regulation", Nature Cell Biology, 11(3):228-234.
Wolska et al. (Apr. 2009) "The Role of Toll-Like Receptors in Hematopoietic Malignancies", Current Molecular Medicine, 9(3):324-335.
Wong et al. (Jul. 2007) "Intracellular Signaling Mechanisms Regulating Toll-like Receptor-mediated Activation of Eosinophils", American Journal of Respiratory Cell and Molecular Biology, 37(1):85-96.
Wong et al. (Feb. 2013) "Microrna-21* Regulates the Prosurvival Effect of GM-CSF on Human Eosinophils", Immunobiology, 218(2):255-262.
Woodruff et al. (Oct. 2, 2007) "Genome-wide Profiling Identifies Epithelial Cell Genes Associated with Asthma and With Treatment Response to Corticosteroids", Proceedings of the National Academy of Sciences of the United States of America, 10(40):15858-15863.
Wu et al. (Nov. 2008) "MicroRNAs Are Differentially Expressed in Ulcerative Colitis and Alter Expression of Macrophage Inflammatory Peptide-2α", Gastroenterology, e24, 135(5):1624-1635.
Xanthou Marietta (Sep. 2008) "Leucocyte Blood Picture in III Newborn Babies", Archives of Disease in Childhood, 47(255):741-746.
Xiang et al. (Feb. 15, 2008) "Wound Repairand Proliferation of Bronchial Epithelial Cells Regulated by CTNNAL1", Journal of Cellular Biochemistry, 103(3):920-930.
Xing et al. (Aug. 23, 2011) "Protease Phenotype of Constitutive Connective Tissue and of Induced Mucosal Mast Cells in Mice Is Regulated by the Tissue", Proceedings of the National Academy of Sciences of the United States of America, 108(34):4210-1421.
Yamazaki et al. (Nov. 2006) "Allergen-specific In Vitro Cytokine Production in Adult Patients with Eosinophilic Esophagitis", Digestive Diseases and Sciences, 51(11):1934-1941.
Yang et al. (Oct. 15, 2006) "Inhibition of Arginase I Activity by RNA Interference Attenuates IL-13-Induced Airways Hyperresponsiveness", The Journal of Immunology, 177(8):5595-5603.
Yang et al. (May 2009) "Th17 and Natural Treg Cell Population Dynamics in Systemic Lupus Erythematosus", Arthritis & Rheumatology, 60(5):1472-1483.
Yee et al. (Jul. 3, 2012) "Insulin-like Growth Factor Receptor Inhibitors: Baby or the Bathwater?", Journal of the National Cancer Institute, 104(13):975-981.
Yi et al. (Mar. 13, 2008) "A Skin MicroRNA Promotes Differentiation by Repressing 'Sternness'", Nature, 452(7184):225-229.
Yin et al. (Jan. 2010) "Targeting the Insulin-like Growth Factor-1 Receptor by Picropodophyllin as a Treatment Option for Glioblastoma", Neuro-Oncology, 12(1):19-27.
Yousefi et al. (Aug. 10, 2008) "Catapult-like Release of Mitochondrial DNA by Eosinophils Contributes to Antibacterial Defense", Nature Medicine, 14(9):949-953.
Yuan et al. (Feb. 7, 2011) "Microrna-203 Inhibits Cell Proliferation by Repressing Δnp63 Expression in Human Esophageal Squamous Cell Carcinoma", BMC Cancer, 11:10 pages.
Zahm et al. (Jul. 2011) "Circulating MicroRNA Is a Biomarker of Pediatric Crohn Disease", Journal of Pediatric Gastroenterology and Nutrition, 53(1):26-33.
Zediak et al. (Mar. 1, 2011) "Cutting Edge: Persistently Open Chromatin at Effector Gene Loci in Resting Memory CD8+ T Cells Independent of Transcriptional Status", Journal of Immunology, 186(5):2705-2709.
Zeng et al. (Feb. 2006) "Extracting Principal Diagnosis, Co-morbidity and Smoking Status for Asthma Research: Evaluation of a Natural Language Processing System", BMC Medical Informatics and Decision Making, 6(1):9 pages.
Zhang et al. (Dec. 2009) "Effects of Endogenous Glucocorticoids on Allergic Inflammation and T(H)1/T(H)2 Balance in Airway Allergic Disease", Annals of Allergy, Asthma & Immunology, 103(6):525-534.
Zhen et al. (Feb. 2007) "IL-13 and Epidermal Growth Factor Receptor Have Critical but Distinct Roles in Epithelial Cell Mucin Production", American Journal of Respiratory Cell and Molecular Biology, 36(2):244-253.
Zheng et al. (Mar. 2009) "Transgenic Expression of Interleukin-13 in the Skin Induces a Pruritic Dermatitis and Skin Remodeling", Journal of Investigative Dermatology, 129(3):742-751.
Zimmerman et al. (Feb. 2003) "Chemokines in Asthma: Cooperative Interaction between Chemokines and IL-13", The Journal of Allergy and Clinical Immunology, 111(2):227-242.
Zimmermann et al. (Apr. 30, 1999) "CC Chemokine Receptor-3 Undergoes Prolonged Ligand-induced Internalization", Journal of Biological Chemistry, 274(18):12611-12618.
Zuo et al. (Jul. 1, 2010) "IL-13 Induces Esophageal Remodeling and Gene Expression by an Eosinophil-Independent, IL-13Rα2-Inhibited Pathway", The Journal of Immunology, 185(1):660-669.
Shen et al. (Apr. 2011) "Plasma MicroRNAs as Potential Biomarkers for Non-small-cell Lung Cancer", Laboratory Investigation, 91(4):579-587.
Sheng et al. (Jun. 2011) "The MUC13 Cell Surface Mucin Protects Against Intestinal Inflammation by Inhibiting Epithelial Cell Apoptosis", Gut, 60(12):1661-1670.
Sherrill et al. (Jul. 2011) "Genetic Dissection of Eosinophilic Esophagitis Provides Insight into Disease Pathogenesis and Treatment Strategies", The Journal of Allergy and Clinical Immunology, 128(1):23-32.
Sherrill et al. (Jul. 1, 2010) "Variants of Thymic Stromal Lymphopoietin and its Receptor Associate with Eosinophilic Esophagitis", Journal of Allergy and Clinical Immunology, 126(1):160-165.
Shinkai et al. (Aug. 1, 1999) "A Novel Human CC Chemokine, Eotaxin-3, Which Is Expressed in IL-4-Stimulated Vascular Endothelial Cells, Exhibits Potent Activity Toward Eosinophils", The Journal of Immunology, 163(3):1602-1610.
Shinkai et al. (Nov. 2002) "N-terminal Domain of Eotaxin-3 is Important for Activation of CC Chemokine Receptor 3", Protein Engineering, Design and Selection, 15(11):923-929.
Shoda et al. (Jan. 2020) "Molecular, Endoscopic, Histologic, and Circulating Biomarker-based Diagnosis of Eosinophilic Gastritis: Multi-site Study", The Journal of Allergy and Clinical Immunology, 145(1):255-269.
Valadi et al. (Jun. 2007) "Exosome-Mediated Transfer of mRNA and microRNA is a Novel Mechanism of Genetic Exchange Between Cells", Nature Cell Biology, 9(6):654-659.
Simon et al. (Oct. 10, 2005) "Roadmap for Developing and Validating Therapeutically Relevant Genomic Classifiers", Journal of Clinical Oncology, 23(29):7332-7341.
Simonini et al. (Nov. 15, 2010) "Epigenetically Deregulated Microrna-375 is Involved in a Positive Feedback Loop with Estrogen Receptor Alpha in Breast Cancer Cells", Cancer Research, 70(22):9175-9184.
Sin et al. (Sep. 2011) "Nerve Growth Factor or IL-3 Induces more IL-13 Production from Basophils of Allergic Subjects than from Basophils of Nonallergic Subjects", The Journal of Allergy and Clinical Immunology, 108(3):387-393.
Sinicropi et al. (2006) "Gene Expression Profiling Utilizing Microarray Technology and RT-PCR", BioMEMS and Biomedical Nanotechnology, 23-46.
Slonim Donnak (Dec. 2002) "From Patterns to Pathways: Gene Expression Data Analysis Comes of Age", Nature Genetics, 32:502-508.
Smith et al. (Jun. 2010) "Insulin-Like Growth Factor-I Regulation of Immune Function: A Potential Therapeutic Target in Autoimmune Diseases?", Pharmacological Reviews, 62(2):199-236.
Smith et al. (Feb. 7, 2010) "MicroRNAs, Development of Barrett's Esophagus, and Progression to Esophageal Adenocarcinoma", World Journal of Gastroenterology, 16(5):531-537.
Sonkoly et al. (Jul. 2007) "MicroRNAs: Novel Regulators Involved in the Pathogenesis of Psoriasis?", PLoS One, e610, 2(7):8 pages.
Sonkoly et al. (Dec. 2010) "MIR-155 is Overexpressed in Patients with Atopic Dermatitis and Modulates T-cell Proliferative Responses by Targeting Cytotoxic T Lymphocyte-associated Antigen 4", The Journal of Allergy and Clinical Immunology, 126(3):581-589.

(56) References Cited

OTHER PUBLICATIONS

Sprenger et al. (Jan. 2009) "Eosinophilic Oesophagitis: An Enigmatic, Emerging Disease", The Netherlands Journal of Medicine, 67(1):8-12.
Spry C. (Sep. 1976) "Eosinophilia in Addison's Disease", Yale Journal of Biology and Medicine, 49(4):411-413.
Stansfield et al. (Dec. 2009) "Periostin Is a Novel Factor in Cardiac Remodeling After Experimental and Clinical Unloading of the Failing Heart", The Annals of Thoracic Surgery, 88(6):1916-1921.
Stappert et al. (Aug. 1994) "A Short Core Region of E-cadherin is Essential for Catenin Binding and is Highly Phosphorylated", Cell Communication & Adhesion, 2(4):319-327.
Stein et al. (Jun. 2008) "Anti-IL-5 (Mepolizumab) Therapy Reduces Eosinophil Activation Ex Vivo and Increases IL-5 and IL-5 Receptor Levels", The Journal of Allergy and Clinical Immunology, 121(6):1473-1483.
Stein et al. (Nov. 2010) "Targeting Interleukin (IL) 5 for Asthma and Hypereosinophilic Diseases", Recent Patents on Inflammation & Allergy Drug Discovery, 4(3):201-209.
Stothard P. (Jun. 2000) "Javascript Programs for Analyzing and Formatting Protein and DNA Sequences", BioTechniques, 28(6):1102-1104.
Straumann et al. (Nov. 2010) "Budesonide Is Effective in Adolescent and Adult Patients With Active Eosinophilic Esophagitis", Gastroenterology, 139(5):1526-1537.
Straumann et al. (Feb. 2005) "Eosinophilic esophagitis: escalating epidemiology?", The Journal of Allergy and Clinical Immunology, 115(2):418-419.
Straumann Alex (Feb. 3, 2012) "Eosinophilic Esophagitis: Rapidly Emerging Disorder", Swiss Medical Weekly, w13513, 142:8 pages.
Straumann et al. (Dec. 2001) "Idiopathic Eosinophilic Esophagitis is Associated with a T(H)2-type Allergic Inflammatory Response", The Journal of Allergy and Clinical Immunology, 108(6):954-961.
Straumann et al. (May 2011) "Long-term Budesonide Maintenance Treatment is Partially Effective for Patients with Eosinophilic Esophagitis", Clinical Gastroenterology and Hepatology, 9(5):370-372.
Straumann et al. (Apr. 2012) "Pediatric and Adult Eosinophilic Esophagitis: Similarities and Differences", Allergy, 67(4):477-490.
Strausberg et al. (2002) "Reading the Molecular Signatures of Cancer", Microarrays and Cancer Research, 11-16.
Suire et al. (Apr. 2005) "p84, a New Gβγ-activated Regulatory Subunit of the Type IB Phosphoinositide 3-kinase p110γ", Current Biology, 15(6):566-570.
Svensson et al. (Apr. 2005) "Human Eosinophils Selectively Recognize and Become Activated by Bacteria Belonging to Different Taxonomic Groups", Microbes and Infection, 7(4):720-728.
Talley et al. (Jan. 1990) "Eosinophilic Gastroenteritis: A Clinicopathological Study of Patients with Disease of the Mucosa, Muscle Layer, and Subserosal Tissues", Gut, 31(1):54-58.
Tan et al. (Mar. 15, 2011) "HYAL1 Overexpression is Correlated with the Malignant Behavior of Human Breast Cancer", International Journal of Cancer, 128(6):1303-1315.
Teitelbaum et al. (May 2002) "Eosinophilic Esophagitis in Children: Immunopathological Analysis and Response to Fluticasone Propionate", Gastroenterology, 122(5):1216-1225.
Tezza et al. (Jun. 2013) "Epigenetics of Allergy", Early Human Development, 89(Suppl 1):S20-S21.
Tian et al. (Oct. 1, 2010) "Visualizing of the Cellular Uptake and Intracellular Trafficking of Exosomes by Live-cell Microscopy", Journal of Cellular Biochemistry, 111(2):488-496.
Tkachuk et al. (Nov. 19, 1996) "Regulation and Role of Urokinase Plasminogen Activator in Vascular Remodelling", Clinical and Experimental Pharmacology and Physiology, 23(9):759-765.
Todorov et al. (2018) "Principal Components Analysis: Theory and Applicaiton to Gene Expression Data Analysis", Genomics and Computational Biology, e100041, 4(2):7 pages.
Trapnell et al. (Apr. 2009) "TopHat: Discovering Splice Junctions with RNA-Seq", Bioinformatics, 25(9):1105-1111.
Trapnell et al. (May 2010) "Transcript Assembly and Quantification by RNA-seq Reveals Unannotated Transcripts and Isoform Switching During Cell Differentiation", Nature Biotechnology, 28(5):511-515.
Tsang et al. (Mar. 2010) "Oncofetal H19-derived MIR-675 Regulates Tumor Suppressor RB in Human Colorectal Cance", Carcinogenesis, 31(3):350-358.
Tsuchiya et al. (Jan. 7, 2011) "MicroRNA-210 Regulates Cancer Cell Proliferation through Targeting Fibroblast Growth Factor Receptor-like 1 (FGFRLI)", Journal of Biological Chemistry, 286(1):420-428.
Tsukamoto et al. (Mar. 15, 2010) "MicroRNA-375 is Downregulated in Gastric Carcinomas and Regulates Cell Survival by Targeting PDK1 and 14-3-3ζ", Cancer Research, 70(6):2339-2349.
Tzvetkov et al. (Jul. 5, 2013) "Morphine is a substrate of the organic cation transporter OCT1 and polymorphisms in OCT1 gene affect morphine pharmacokinetics after codeine administration", Biochemical Pharmacology, 86(5):666-678.
Ueda et al. (Jun. 6, 2005) "Inflammation and the Reciprocal Production of Granulocytes and Lymphocytes in Bone Marrow", Journal of Experimental Medicine, 201(11):1771-1780.
United States Patent and tradema, "Office Action, issued in corresponding U.S. Appl. No. 13/051,873", dated Jan. 10, 2012, 25 pages.
Vaishnavi et al. (2013) "Oncogenicand Drug-Sensitive NTRK1 Rearrangements in Lung Cancer", Nature Medicine, 19(11):1469-1472.
Tsuchiya et al., "MicroRNA-210 Regulates Cancer Cell Proliferation through Targeting Fibroblast Growth Factor Receptor-like 1 (FGFRLI)", Journal of Biological Chemistry, Jan. 7, 2011, 286(1):420-428.
Assa'ad et al. (Mar. 2007) "Pediatric Patients With Eosinophilic Esophagitis: An 8-year Follow-up", The Journal of Allergy and Clinical Immunology, 119(3):731-738.
Attwood et al. (Jan. 1993) "Esophageal Eosinophilia with Dysphagia. A Distinct Clinicopathologic Syndrome", Digestive Diseases and Sciences, 38(1):109-116.
Aune et al. (Mar. 2009) "Epigenetics and T heler 1 Differentiation", Immunology, 126(3):299-305.
Ayala et al. (May 15, 1996) "Differential Induction of Apoptosis in Lymphoid Tissues during Sepsis: Variation in Onset, Frequency, and the Nature of the Mediators", Blood, 87(10):4261-4275.
Baker et al. (Apr. 2, 2003) "The Central Role of Receiver Operating Characteristic (ROC) Curves in Evaluating Tests for the Early Detection of Cancer", Journal of the National Cancer Institute, 95(7):511-515.
Baldrick et al. (Jul.-Aug. 2007) "Pollinex Quattro Ragweed: Safety Evaluation of a New Allergy Vaccine Adjuvanted with Monophosphoryl Lipid a (MPL) for the Treatment of Ragweed Pollen Allergy", Journal of Applied Toxicology, 27(4):399-409.
Barratt et al. (Apr. 18, 2012) "ABCB1 haplotype and OPRM1 118A > G genotype interaction in methadone maintenance treatment pharmacogenetics", 5(1):53-62.
Barski et al. (Oct. 2009) "Chromatin Poises miRNA- and Protein-coding Genes for Expression", Genome Research, 19(10):1742-151.
Bass D.A. (Jun. 1975) "Behavior of Eosinophil Leukocytes in Acute Inflammation. I. Lack of Dependence on Adrenal Function", Journal of Clinical Investigation, 55(6):1229-1236.
Bass D.A. (Oct. 1975) "Behavior of Eosinophil Leukocytes in Acute Inflammation. II. Eosinophil Dynamics During Acute Inflammation", Journal of Clinical Investigation, 56(4):870-879.
Ben-Dor et al. (2000) "Tissue Classification with Gene Expression Profiles", Journal of Computational Biology, 7(3-4):559-583.
Berkman et al. (Jun. 2001) "Eotaxin-3 but Not Eotaxin Gene Expression Is Upregulated in Asthmatics 24 Hours after Allergen Challenge", American Journal of Respiratory Cell and Molecular Biology, 24(6):682-687.
Bhattacharya et al. (Dec. 2007) "Increased Expression of Eotaxin-3 Distinguishes Between Eosinophilic Esophagitis and Gastroesophageal Reflux Disease", Human Pathology, 38(12):1744-1753.

(56) References Cited

OTHER PUBLICATIONS

Biesiada et al. (Nov. 2014) "Genetic risk signatures of opioid-induced respiratory depression following pediatric tonsillectomy", Pharmacogenomics, 15(14):1749-1762.
Biton et al. (Mar. 2011) "Epithelial MicroRNAs Regulate Gut Mucosal Immunity Via Epithelium-T Cell Crosstalk", Nature Immunology, 12(3):239-246.
Blanchard et al. (Jan. 2011) "A Striking Local Esophageal Cytokine Expression Profile in Eosinophilic Esophagitis", The Journal of Allergy and Clinical Immunology, e7, 127(1):208-217.
Blanchard et al. (Jan. 2008) "Basics Pathogenesis of Eosinophilic Esophagitis", Gastrointestinal Endoscopy Clinics of North America, 18(1):133-143.
Blanchard et al. (Apr. 1, 2010) "Coordinate Interaction Between IL-13 and Epithelial Differentiation Cluster Genes in Eosinophilic Esophagitis", Journal of Immunology, 184(7):4033-4041.
Blanchard et al. (Sep. 19, 2006) "Eosinophilic Esophagitis: Pathogenesis, Genetics, and Therapy", The Journal of Allergy and Clinical Immunology, 118(5):1054-1059.
Blanchard et al. (Feb. 2006) "Eotaxin-3 and a Uniquely Conserved Gene-Expression Profile in Eosinophilic Esophagitis", Journal of Clinical investigation, 116(2):536-547.
Blanchard et al. (Dec. 2005) "Eotaxin-3/CCL26 Gene Expression in Intestinal Epithelial Cells is Up-regulated by Interleukin-4 and Interleukin-13 Via the Signal Transducer and Activator of Transcription 6", The International Journal of Biochemistry & Cell Biology, 37(12):2559-2573.
Blanchard et al. (Dec. 2007) "IL-13 Involvement in Eosinophilic Esophagitis: Transcriptome Analysis and Reversibility with Glucocorticoids", Journal of Allergy and Clinical Immunology, 120(6):1292-1300.
Blanchard et al. (Jan. 2007) "IL-13 Is Overexpressed in Eosinophilic Esophagitis and Induces Eotaxin-3 Expression in Esophageal Epithelial Cells", The Journal of Allergy and Clinical Immunology, S240, 1 page.
Blanchard et al. (Aug. 24, 2005) "Inhibition of Human lnterleukin-13-induced Respiratory and Oesophageal Inflammation by Anti-human-interleukin-13 Antibody (CAT-354)", Clinical and Experimental Allergy, 35(8):1096-1103.
Blanchard et al. (Jul. 2008) "Periostin Facilitates Eosinophil Tissue Infiltration in Allergic Lung and Esophageal Responses", Mucosal Immunology, 1(4):289-296.
Blennow Kaj (Apr. 2004) "Cerebrospinal Fluid Protein Biomarkers for Alzheimer's Disease", NeuroRx, 1(2):213-225.
Bochner et al. (Jul. 2010) "What Targeting the Eosinophil has Taught Us About their Role in Diseases", The Journal of Allergy and Clinical Immunology, 126(1):16-25.
Boeuf et al. (Mar. 4, 2005) "CyProQuant-PCR: A Real Time RT-PCR Technique for Profiling Human Cytokines, Based on External RNA Standards, Readily Automatable for Clinical Use", BMC Immunology, 6:14 pages.
Bonini et al. (Oct. 1, 1996) "Circulating Nerve Growth Factor Levels are Increased in Humans with Allergic Diseases and Asthma", Proceedings of the National Academy of Sciences of the United States of America, 93(20):10955-10960.
Boon et al. (Oct. 23, 2003) "Comparison of Medulloblastoma and Normal Neural Transcriptomes Identifies a Restricted Set of Activated Genes", Oncogene, 22(48):7687-7694.
Branford et al. (Jul. 27, 2012) "Opioid genetics: the key to personalized pain control?", Clinical Genetics, 82(4):301-310.
Brightling et al. (Jan. 2010) "Interleukin-13: Prospects for New Treatments", Clinical & Experimental Allergy, 40(1):42-49.
Brodeur et al. (Jan. 1997) "Expression of TrkA, TrkB and TrkC in Human Neuroblastomas", Journal of Neuro-Oncology, 31(1-2):49-55.
Broide et al. (Mar. 2011) "Advances in Mechanisms of Asthma, Allergy, and Immunology in 2010", The Journal of Allergy and Clinical Immunology, 127(3):689-695.
Broide et al. (2009) "Immunomodulation of Allergic Disease", Annual Review of Medicine, 60:279-291.
Buitenhuis et al. (Jun. 1, 2005) "Differential Regulation of Granulopoiesis by the Basic Helix-loop-helix Transcriptional Inhibitors Id1 and Id2", Blood, 105(11):4272-4281.
Bullens et al. (Nov. 3, 2006) "IL-17 mRNA in Sputum of Asthmatic Patients: Linking T Cell Driven Inflammation and Granulocytic Influx?", Respiratory Research, 7(1):9 pages.
Bullock et al. (Jul. 2007) "Interplay of Adaptive Th2 Immunity with Eotaxin-3/c-C Chemokine Receptor 3 in Eosinophilic Esophagitis", Journal of Pediatric Gastroenterology and Nutrition, 45(1):22-31.
Burnett et al. (Jan. 27, 2012) "RNA-based Therapeutics: Current Progress and Future Prospects", Chemistry & Biology, 19(1):60-71.
Buscaglia et al. (Jun. 2011) "Apoptosis and the Target Genes of MicroRNA-21", Chinese Journal of Cancer, 30(6):371-380.
Busse et al. (Apr. 2010) "A Review of Treatment with Mepolizumab, an Anti-il-5 Mab, in Hypereosinophilic Syndromes and Asthma", The Journal of Allergy and Clinical Immunology, 25(4):803-813.
Cai et al. (Mar. 2017) "The Imprinted H19 Noncoding RNA is a Primary MicroRNA Precursor", RNA, 13(3):313-316.
Caldwell et al. (Sep. 2017) "Cadherin 26 is an alpha Integrin-binding Epithelial Receptor Regulated during Allergic Inflammation", Mucosal Immunology, 10(5):1190-1201.
Caldwell et al. (Feb. 2011) "Global Gene Expression Profile Analysis in Eosinophilic Gastritis Identifies CDH26", The Journal of Allergy and Clinical Immunology, Abstract 831, 127(2):1 page.
Caldwell et al. (Apr. 2010) "Glucocorticoid-regulated Genes in Eosinophilic Esophagitis: A Role for FKBP51", American Academy of Allergy, Asthma & Immunology, 125(4):879-888.
Cameron et al. (Mar. 2000) "Evidence for Local Eosinophil Differentiation Within Allergic Nasal Mucosa: Inhibition with Soluble IL-5 Receptor", The Journal of Immunology, 164(3):1538-1545.
Caramori et al. (Aug. 2005) "Anti-inflammatory Mechanisms of Glucocorticoids Targeting Granulocytes", Current Drug Targets—Inflammation & Allergy, 4(4):455-463.
Carriere et al. (Jan. 2, 2007) "IL-33, the IL-1-like Cytokine Ligand for ST2 Receptor, is a Chromatin-associated Nuclear Factor in Vivo", Proceedings of the National Academy of Sciences of the United States of America, 104(1):282-287.
Carthew et al. (Feb. 20, 2009) "Origins and Mechanisms of miRNAs and siRNAs", Cell, 136(4):642-655.
Chehade et al. (Jun. 2010) "Food Allergy and Eosinophilic Esophagitis", Current Opinion in Allergy and Clinical Immunology, 10(3):231-237.
Sahin et al. (Oct. 2014) "MRNA-Based Therapeutics—Developing a New Class of Drugs", Nature reviews, 13(10):759-780.
TaqMan(R) Human MicroRNA Arrays, Carlsbad, CA, USA, Jun. 1, 2008, pp. 1-2.
The Merck Manual, 1992,1229-1230 & 1233.
The Merck Manual, 1992, 646-649.
Ordoñez et al. (Dec. 2000) "Epithelial Desquamation in Asthma", American Journal of Respiratory and Critical Care Medicine, 162(6):2324-2329.
Anthony et al. (Dec. 2007) "Protective Immune Mechanisms in Helminth Infection", Nature Reviews Immunology, 7(12):975-987.
Johnnidis et al. (Feb. 28, 2008) "Regulation of Progenitor Cell Proliferation and Granulocyte Function by MicroRNA-223", Nature, 451:1125-1129.
Azouz et al. (May 27, 2020) "Functional role of kallikrein 5 and proteinase-activated receptor 2 in eosinophilic esophagitis", Sci. Transl. Med. 12, eaaz773. pp 1-15.
Azouz et al. (May 27, 2020) Supplementary Materials for "Functional role of kallikrein 5 and proteinase-activated receptor 2 in eosinophilic esophagitis", (Sci. Transl. Med. 12, eaaz773) stm.sciencemag.org/cgi/content/full/12/545/eaaz7773/DC1.
Madhusudan et al. (2007) "Tyrosine Kinase Inhibitors and Cancer Therapy", Recent Results in Cancer Research, 172:25-44.
Markowitz et al. (Apr. 2003) "Elemental Diet Is an Effective Treatment for Eosinophilic Esophagitis in Children and Adolescents", The American Journal of Gastroenterology, 98(4):777-782.
Martin et al. (May 2003) "Role of Innate Immune Factors in the Adjuvant Activity of Monophosphoryl Lipid A", Infection and Immunity, 71(5):2498-2507.
Martinez-Nunez et al. (Jan. 21, 2011) "The Interleukin 13 (IL-13) Pathway in Human Macrophages is Modulated by MicroRNA-155

(56) References Cited

OTHER PUBLICATIONS

Via Direct Targeting of Interleukin 13 Receptor Alpha 1 (IL13Ralpha1)", Journal of Biological Chemistry, 286(3):1786-1794.

Matsushima (2010) "MicroRNAs and Esophageal Squamous Cell Carcinoma", Digestion, 82(3):38-144.

Mattes et al. (Nov. 3, 2009) "Antagonism of microRNA-126 Suppresses the Effector Function of TH2 Cells and the Development of Allergic Airways Disease", Proceedings of the National Academy of Sciences of the United States of America, 106(44):18704-18709.

Mayer et al. (Apr. 27, 2001) "Identification of Receptor Binding and Activation Determinants in the N-Terminal and N-loop Regions of the CC Chemokine Eotaxin", Journal of Biological Chemistry, 276(17):13911-13916.

Mayo Clinic (Oct. 10, 2017) "Eosinophilic Esophagitis", Available at: http://www.mayoclinic.org/diseases-conditions/eosinophilic-esophagitis/basics/treatment/con-20035681.

Mayoral et al. (Jan. 1, 2009) "MicroRNA-221-222 Regulate the Cell-Cycle in Mast Cells", Journal of Immunology, 182(1):433-445.

McGettrick et al. (Sep. 25, 2007) "Toll-like Receptors: Key Activators of Leucocytes and Regulator of Haematopoiesis", British Journal of Haematology, 139(2):185-193.

Medina et al. (Sep. 2, 2010) "OncomiR Addiction in an in Vivo Model of microRNA-21-induced Pre-Pβ-cell Lymphoma", Nature, 467(7311):86-90.

Meineke et al. (Dec. 2002) "Pharmacokinetic modelling of morphine, morphine-3-glucuronide and morphine-6-glucuronide in plasma and cerebrospinal fluid of neurosurgical patients after short-term infusion of morphine", British Journal of Clinical Pharmacology, 54(6):592-603.

Menard-Katcher et al. (2012) "MicroRNAs are Altered in Eosinophilic Esophagitis", Gastroenterology, 142(5):8440.

Menzies-Gow et al. (Apr. 2003) "Anti-IL-5 (Mepolizumab) Therapy Induces Bone Marrow Eosinophil Maturational Arrest and Decreases Eosinophil Progenitors in the Bronchial Mucosa of Atopic Asthmatics", The Journal of Allergy and Clinical Immunology, 111(4):714-719.

Meyer et al. (Jan. 2013) "The UCSC Genome Browser database: Extensions and Updates 2013", Nucleic Acids Research, 41:D64-D69.

Michaels et al. (Feb. 5-11, 2005) "Prediction of Cancer Outcome with Microarrays: A Multiple Random Validation Strategy", Lancet, 365(9458):488-492.

Milbrandt J. (Nov. 6, 1987) "A Nerve Growth Factor-induced Gene Encodes a Possible Transcriptional Regulatory Factor", Science, 238(4828):797-799.

Milgrom et al. (Dec. 23, 1999) "Treatment of Allergic Asthma with Monoclonal Anti-IgE Antibody", The New England Journal of Medicine, 341(26):1966-1973.

Mishra et al. (Jan. 1, 2001) "An Etiological Role for Aeroallergens and Eosinophils in Experimental Esophagitis", Journal of Clinical Investigation, 107(1):83-90.

Mishra et al. (Jan. 2008) "Esophageal Remodeling Develops as a Consequence of Tissue Specific IL-5-induced Eosinophilia", Gastroenterology, 134(1):204-214.

Mishra et al. (Mar. 1, 2002) "IL-5 Promotes Eosinophil Trafficking to the Esophagus", The Journal of Immunology, 168(5):2464-2469.

Mishra et al. (Nov. 2003) "Intratracheal IL-13 Induces Eosinophilic Esophagitis by an IL-5, Eotaxin-1, and STAT6-Dependent Mechanism", Gastroenterology, 125(5)1419-1427.

Mitchell et al. (Jul. 29, 2008) "Circulating microRNAs as Stable Blood-based Markers for Cancer Detection", Proceedings of the National Academy of Sciences of the United States of America, 105(30):10513-10518.

Mizuno et al. (2013) "Genotype of Abcc3-211c > T Influences the Pharmacokinetics of Morphine Glucuronide in Children", Clinical Pharmacology & Therapeutics, 93:S63.

Mogil et al. (Jul. 6, 1999) "The genetic mediation of individual differences in sensitivity to pain and its inhibition", PNAS, 96(14):7744-7751.

Molina-Infante et al. (May 7, 2008) "Overlap of Reflux and Eosinophilic Esophagitis in Two Patients Requiring Different Therapies: A Review of the Literature", World Journal of Gastroenterology, 14(9):1463-1466.

Mori et al. (Jan. 16, 2009) "Identification of the Human Eosinophil Lineage-committed Progenitor: Revision of Phenotypic Definition of the Human Common Myeloid Progenitor", Journal of Experimental Medicine, 206(1):183-193.

Mukhopadhyay et al. (Jul. 2010) "Matrix Metalloproteinase-12 is a Therapeutic Target for Asthma in Children and Young Adults", The Journal of Allergy and Clinical Immunology, 126(1):70-76.

Mulder et al. (Jan. 12, 2011) "Understanding Eosinophilic Esophagitis: The Cellular and Molecular Mechanisms of an Emerging Disease", Mucosal Immunology, 4(2):139-147.

Murata et al. (Jul. 2008) "Activation of Toll-like Receptor 2 by a Novel Preparation of Cell Wall Skeleton from *Mycobacterium bovis* BCG Tokyo (SMP-105) Sufficiently Enhances Immune Responses Against Tumors", Cancer Science, 99(7):1435-1440.

Nagai et al. (Jun. 2006) "Toll-like Receptors on Hematopoietic Progenitor Cells Stimulate Innate Immune System Replenishment", Immunity, 24(6):801-812.

Nagase et al. (Oct. 15, 2003) "Expression and Function of Toll-like Receptors in Eosinophils: Activation by Toll-like Receptor 7 Ligand", Journal of Immunology, 171(8):3977-3982.

Navarro et al. (Jun. 1, 2010) "Small RNAs Guide Hematopoietic Cell Differentiation and Function", Journal of Immunology, 184(11):5939-5947.

Naya et al. (May 7, 2001) "Discovery of a Novel CCR3 Selective Antagonist", Bioorganic & Medicinal Chemistry Letters, 11(9):1219-1223.

Naya et al. (Jun. 2003) "Structure-Activity Relationships of 2-(Benzothiazolylthio)acetamide Class of CCR3 Selective Antagonist", Chemical and Pharmaceutical Bulletin, 51(6):697-701.

Newberry et al. (Nov. 2005) "Strongyloides Hyperinfection Presenting as Acute Respiratory Failure and Gram-negative Sepsis", Chest, 128(5):3681-3684.

Noel et al. (Jul. 2004) "Clinical and Immunopathologic Effects of Swallowed Fluticasone for Eosinophilic Esophagitis", Clinical Gastroenterology and Hepatology, 2(7):568-575.

Notterman et al. (2002) "Tumor Biology and Microarray Analysis of Solid Tumors: Colorectal Cancer as a Model System", Microarrays and Cancer Research, 81-111.

Novak et al. (Apr. 1, 2007) "CCL23 Expression Is Induced by IL-4 in a STAT6-Dependent Fashion", Journal of Immunology, 178(7):4335-4341.

Ogbogu et al. (Dec. 2009) "Hypereosinophilic Syndromes: A Multicenter, Retrospective Analysis of Clinical Characteristics and Response to Therapy", The Journal of Allergy and Clinical Immunology, 124(6):1319-1325.

Ozawa et al. (Oct. 2009) "BRAK/CXCL14 Expression Oral Carcinoma Cells Completely Suppresses Tumor Cell Xenografts in SCID Mouse", Biomedical Research, 30(5):315-318.

Ozawa et al. (Oct. 11, 2009) "Restoration of BRAK/CXCL14 Gene Expression by Gefitinib is Associated with Antitumor Efficacy of the Drug in Head and Neck Squamous Cell Carcinoma", Cancer Science, 100(11):2202-2209.

Ozdas et al. (Sep. 2004) "Investigation of Vocal Jitter and Glottal Flow Spectrum as Possible Cues for Depression and Near-Term Suicidal Risk", Transactions on Biomedical Engineering, 51(9):1530-1540.

Papagiannakopoulos et al. (Oct. 1, 2008) "MicroRNA-21 Targets a Network of Key Tumor-Suppressive Pathways in Glioblastoma Cells", Cancer Research, 68(19):8164-8172.

Park et al. (Dec. 27, 2006) "Genetic Polymorphisms in the ABCB1 Gene and the Effects of Fentanyl in Koreans", Clinical Pharmacology & Therapeutics, 81(4):539-546.

Patent Cooperation Treaty "International Preliminary Report on Patentability and Written Opinion" in corresponding International application No. PCT/US2012/044061, dated Dec. 23, 2013, 7 pages.

Patent Cooperation Treaty "International Search Report dated Nov. 9, 2015 for International Application No. PCT/US2015/044461", 11 pages.

(56) References Cited

OTHER PUBLICATIONS

Peeters et al. (Apr. 8, 2005) "Real-time RT-PCR Quantification of mRNA Encoding Cytokines and Chemokines in Histologically Normal Canine Nasal, Bronchial and Pulmonary Tissue", Veterinary Immunology and Immunopathology, 104(3-4):195-204.
Persson et al. (Jun. 2001) "Bactericidal Activity of Human Eosinophilic Granulocytes Against *Escherichia coli*", Infection and Immunity, 69(6):3591-3596.
Petriv et al. (Aug. 31, 2010) "Comprehensive MicroRNA Expression Profiling of the Hematopoietic Hierarchy", Proceedings of the National Academy of Sciences of the United States of America, 107(35):15443-15448.
Liesveld, Jane., "Hypereosinophilic Syndrome" Merck Manuals Professional Edition—last revised Dec. 2018, 5 pages.
Butz et al., "Efficacy, Dose Reduction, and Resistance to High-Dose Fluticasone in Patients With Eosinophilic Esophagitis" Gastroenterology 2014;147:324-333.
Kalinin et al., "Deep learning in pharmacogenomics: from gene regulation to patient stratification" Pharmacogenomics (2018) 19(7) 629-650.
Siddique et al., "Clinicopathologic and gene expression analysis of initial biopsies from patients with eosinophilic esophagitis refractory to therapy" Human Pathology (2017) 68,79-86.
Eisen et al. 1998. Proc. Natl. Acad. Sci. USA (25)95, p. 14863-14868.
European Search Report and Written Opinion, 16885429.7, dated Jul. 23, 2019, 15 pages.
Prakash et al. Expert Rev. Resp. Med. 4(3), 395-411 (2010).
Transcription Profiling of *Drosophila* 40 Homozygous Raleigh Lines to Understand the Genetic Basis of Compelx Traits in *Drosophila*, Accession of No. E-MEXP-1594, (2013).
Arefi et al. 2012. Internat. Journ. of Hemataology, 96(3):320-326.
Elsner et al. 1997. Euro. J. of Immuno. vol. 27, pp. 2892-2898.
GeneSpring User Manual, version 6.1. Silicon Genetics. Nov. 14, 2003.
Sinicropi et al., BioMEMS and biomedical nanotechnology. Springer US, 2006. 23-46.
"Rs77569859", Dec. 16, 2010, pp. 1-2, Retrieved from the Internet: URL: http://www.ncbi.nlm.nih.gov/projects/SNP/snp-SS.cgi?subsnp_id=276404309.
"Rs8041227", Dec. 16, 2010, pp. 1-2, Retrieved from the Internet: URL: http://www.ncbi.nlm.nih.gov/projects/SNP/snp-SS.cgi?subsnp_id=90109558.
"Rs2898261", Dec. 16, 2010, pp. 1-2, Retrieved from the Internet: URL: http://www.ncbi.nlm.nih.gov/projects/SNP/snp-SS.cgi?subsnp_id=279682708.
Shoda et al. Lancet. Gastroenterology Hepatol. Jul. 2018; 3(7):477-488; Epub 2018.
Descamps et al., Cancer Res. 61,4337-4340 (2001).
Oyoshi Current Opinion in Pediatrics, 2015, 27(6), 741-747.
Chen et al. Jiepoukexue Jinzhan (2007), 13(4), 388-391.
Rochlitzer et al. Biochem Soc. Trans (2006), 34(4), 594-599.
Massenstein et al. J. Allergy Clin. Immuno. 2006; 118:597-605.
International Search Report and Written Opinion, PCT/US2016/068236, dated Dec. 22, 2016.
Recombinant Mouse N-Cadherin Fc Chimera Protein, CF 6626-NC . . . https://www.mdsysytems.com> N-Cadherin Jan. 14, 2011—Mouse N-Caderin protein (6626-NC) is manufactured by R&D Systems. Retrieved Aug. 15, 2018.
Recombinant Human VE-Cadherin Fc Chimera Protein, CF . . . https://www.mdsysytems.com> N-Cadherin Jul. 4, 2015—Huamn VW-Caderin protein (938-VC) is manufactured by R&D Systems. Retrieved Aug. 15, 2018.

\* cited by examiner 3-(3-chlorophenyl)carboxy-7-hydroxymethyl coumarin $IC_{50} = 52 \pm 12$ μM (lit. 94 nM)

II
3-carboxy-7-hydroxymethyl coumarin

COMPOSITIONS AND METHODS FOR TREATING ALLERGIC INFLAMMATORY CONDITIONS

CROSS REFERENCE TO RELATED APPLICATIONS

This application is a continuation of U.S. patent application Ser. No. 16/069,412, filed on Jul. 11, 2018, which is a national stage entry, filed under 35 U.S.C. § 371, of International Application No. PCT/US2016/068238, filed on Dec. 22, 2016, which claims the benefit of U.S. Provisional Patent Application No. 62/278,246, filed Jan. 13, 2016, the content of which is incorporated herein by reference in its entirety.

FIELD OF THE INVENTION

The invention disclosed herein generally relates to compositions and methods for treating an allergic inflammatory condition.

BACKGROUND

Epithelial barrier impairment has been implicated in the development of allergic disease. However, the molecular mechanisms by which impaired epithelial barrier function induces Th2-type immune responses remain largely unknown.

Epithelial cells are uniquely positioned as the first line of defense against type-2 (Th2)-cell-mediated immune insults (Hammad, H. & Lambrecht, B. N. *Immunity* 43, 29-40 (2015)). In response to perturbation of barrier integrity, acute injury and/or immune stimulation, epithelial cells secrete discrete pro-inflammatory cytokines such as interleukin-1 (IL-1), IL-25, IL-33, and TSLP, which prime dendritic cells to promote Th2 immune responses (Hammad, H. & Lambrecht, B. N. *Immunity* 43, 29-40 (2015)). The esophageal epithelium is comprised of non-keratinized stratified squamous cells, including a layer of mitotically-active cells (stratum basalis), several layers of actively transporting cells (stratum spinosum), and the most luminal layers (stratum corneum) comprised of apical cell membranes, apical junctional complexes, and a matrix of glycoproteins and structural proteins such as filaggrin that together provide a tight epithelial barrier which allows sampling but not penetration of external antigens (Orlando, R. C. *Best practice & research. Clinical gastroenterology* 24, 873-882).

The importance of loss of barrier integrity in eliciting Th2 responses is illustrated by predisposition to atopy in individuals harboring loss of function mutations in the proteinase inhibitor SPINK5. Homozygous loss of SPINK5 results in uncontrolled proteolytic activity in the skin which leads to barrier defect and atopy. An imbalance between SPINK5 and proteinases has been proposed to contribute to the pathogenesis of atopic dermatitis (AD) (Furio, L. et al. *The Journal of experimental medicine* 211, 499-513). Whether a similar process is generalizable to other inflammatory diseases has not been demonstrated.

Eosinophilic esophagitis (EoE) is an inflammatory Th2 type immune disease of the esophagus. EoE is considered to be a chronic immune system disease. Although it was identified only during the last twenty years, it is now considered a major cause of digestive system (gastrointestinal) illness. In EoE, eosinophils (a type of white blood cell) build up in the lining of the esophagus. This buildup, which may be a reaction to foods, allergens or acid reflux, can inflame and/or injure the esophageal tissue. Damaged esophageal tissue can lead to difficulty swallowing or lead to other complications. Symptoms include difficulty swallowing (dysphagia), food impaction, chest pain that is often centrally located and does not respond to antacids, persistent heartburn, upper abdominal pain, lack of response to gastroesophageal reflux disease (GERD) medication, and backflow of undigested food (regurgitation).

Current clinical standards for diagnosis of EoE include (i) endoscopy to inspect the lining of the esophagus for inflammation and swelling, horizontal rings, vertical furrows, narrowing (strictures) and white spots; (ii) biopsy of esophageal tissue with one biopsy showing more than 15 eosinophils per high power field in patients using a proton pump inhibitor (PPI) for approximately 8 weeks.

Treatment for EoE that is not responsive to PPIs includes an orally administered topical steroid, such as fluticasone or budesonide. Where topical steroids prove ineffective, prednisone may be prescribed. There is a need for new treatment options for EoE and similar allergic inflammatory disorders characterized by inflammation of squamous epithelium. The present disclosure addresses this need.

SUMMARY OF THE INVENTION

The present disclosure generally provides methods of treating an allergic inflammatory condition in a subject in need thereof, the allergic inflammatory condition characterized by inflammation of a squamous epithelium in a target tissue of the subject, by replenishing SPINK7 protein and/or SPINK7 anti-proteinase activity in the target tissue. In embodiments, the target tissue is esophageal tissue and the methods are for treating EoE.

In embodiments, the disclosure provides methods of treating an allergic inflammatory condition in a subject in need thereof, the allergic inflammatory condition characterized by inflammation of a squamous epithelium in a target tissue of the subject, the method comprising administering to the subject a pharmaceutical composition comprising an amount of a therapeutic agent effective to replenish SPINK7 protein and/or SPINK7 anti-proteinase activity in the target tissue. In embodiments, the squamous epithelium is of esophageal tissue. In embodiments, the allergic inflammatory condition is esophageal eosinophilia (EE) or eosinophilic esophagitis (EoE).

In embodiments, the therapeutic agent is a serine proteinase inhibitor. In embodiments, the therapeutic agent is an alpha-1 proteinase inhibitor. In embodiments, the alpha-1 proteinase inhibitor is an alpha-1 antitrypsin (A1AT) inhibitor.

In embodiments, the therapeutic agent is an inhibitor of urokinase plasminogen activator (uPA) or kallikrein 5 (KLK5) in the target tissue. In embodiments, the therapeutic agent is a proteinase inhibitor, a KLK5-Fc fusion protein, a KLK5 anti-sense polynucleotide, a KLK5-directed miRNA, a KLK5-directed shRNA, or a KLK5-directed antibody. In embodiments, the therapeutic agent is selected from 3-(3-chlorophenyl)carboxy-7-hydroxymethyl coumarin or 3-carboxy-7-hydroxymethyl coumarin.

In embodiments, the therapeutic agent comprises a recombinant mRNA encoding a SPINK7 protein, or a recombinant SPINK7 polypeptide. In embodiments, the therapeutic agent comprises a recombinant mRNA encoding a member of the SPINK protein family, or a recombinant mRNA encoding a SPINK family member polypeptide.

In embodiments, the methods further comprise subjecting the patient to a dietary modification to eliminate one or more potential food allergens.

In embodiments, the subject is human.

BRIEF DESCRIPTION OF THE DRAWINGS

FIG. 3A shows a heatmap representing the fold change of 17 EDC genes that are significantly ($p<0.05$) altered by SPINK7 depletion in EPC2 cells following ALI differentiation (day 14). FIG. 3B is a bar graph showing FLG mRNA expression in NSC or SPINK7-depleted EPC2 or primary esophageal epithelial cells following ALI differentiation from three independent experiments performed in triplicates. FIG. 3C is a gel showing filaggrin protein expression in NSC or SPINK7-depleted EPC2 cells following ALI differentiation was assessed by western blot.

FIG. 5A shows GO analysis of the SPINK7-EoE overlap gene set depicting human phenotypes.

FIG. 6A shows Hematoxylin and eosin (H&E)-stained sections of NSC or SPINK7-depleted EPC2 cells and primary esophageal epithelial cells following ALI differentiation (day 14). Arrows point on the non-cellular associated areas that were formed.

FIG. 6B shows H&E-stained sections of NSC or SPINK7-depleted EPC2 cells grown for 7, 9 or 11-14 days in the ALI cultures. The percent of non-cell associate areas in the tissues is represented. Arrow point on the blabbing of the stratified layers at day 11-14. FIG. 6C shows Electron microscopy images of NSC or SPINK7-depleted EPC2 cells following ALI differentiation (day 14). Arrows depict microplicae at the epithelial junctions. Dashed arrows depict absent of microplicae at epithelial junctions.

FIG. 9A is a heat map of cytokine and chemokine expression derived from supernatants of NSC or SPINK7-depleted EPC2 cells following ALI differentiation (day 14) that were altered (All the indicated cytokines and chemokines were expressed at a concentration >1 pg/ml, $-2>$Fold Change (FC)$>2$, $P<0.05$). Data presented as the mean fold change (FC) of three independent experiments performed in duplicate and triplicate. *CXCL1/2/3-detection of CXCL1, CXCL2 and CXCL3 together. FIG. 9B is a bar graph showing IL-8 protein expression in supernatants of either NSC or SPINK7-depleted EPC2 cells that were treated either with a vehicle or with cyclosporine A (CsA), or FK506 during ALI differentiation. FIG. 9C is a bar graph showing eosinophils derived from human peripheral blood were subjected to migration assay using a transwell chamber with 5 μm pore size. KSFM media was placed at the bottom chamber and was either fresh KSFM media with or without eotaxin-1 or KSFM media derived from supernatants of differentiated EPC2 cells that were either transduced with NSC or SPINK7 shRNA.

FIG. 10A is a bar graph showing quantification of uPA activity in supernatants derived from (NSC) or SPINK7-depleted EPC2 cells following during ALI differentiation (day 7-9). FIG. 10B is a bar graph showing quantification of the activity of serine proteinases with trypsin-like activity in supernatants derived from (NSC) or SPINK7-depleted EPC2 cells and primary esophageal cells following ALI differentiation. Proteinase activity in the supernatants is calculated as nM concentrations according to standard dilutions of recombinant hKLK5. In vitro activity assays of KLK5 (FIG. 10C), KLK7 (FIG. 10D) and KLK11 (FIG. 10E) in the presence of the indicated concentrations of SPINK7. Data are represented as the mean±s.e.m.

FIG. 11A shows quantitative analysis of cells demonstrating alterations of junctional proteins from the total number of cells from NSC or SPINK7-depleted EPC2 cells following ALI differentiation. FIG. 11B shows a graph depicting FITC-dextran flux measured at day 14 of ALI differentiation from NSC and SPINK7-depleted EPC2 cells for the indicated time points. All data are representative of at least three experiments performed in triplicate and are represented as the mean±SD.

FIG. 12A is a bar graph showing FPKM values of uPA in the esophagus of EoE patients and controls. FIG. 12B is a bar graph showing analysis of the uPA proteolytic activity (active units-AU) in esophageal biopsies from 6 normal and 6 EoE patients. FIG. 12C shows expression of uPAR (according to the mean fluorescence intensity-MFI) on the cell surface of eosinophils ($7AAD^{low}$, $CD45^+$, $CD11B^+$, Siglec $8^+$) derived from blood or esophageal biopsies from 8 EoE patients using flow cytometry. FIG. 12D is a bar graph showing quantification of trypsin-like activity in supernatants derived from NSC or SPINK7-depleted EPC2 cells that were treated with A1AT or a vehicle following ALI differentiation. FIG. 12E are electrical resistance measurements of NSC or SPINK7-depleted EPC2 cells that were treated with A1AT or a vehicle during ALI differentiation (Day 7). FIG. 12F are H&E staining images of NSC or SPINK7-depleted EPC2 cells that were treated with A1AT or a vehicle after ALI differentiation (Day 14)-add. FIG. 12G are images of co-immunofluorescence staining of E-cadherin and Filaggrin of NSC or SPINK7-depleted EPC2 cells that were treated with A1AT or a vehicle following ALI differentiation.

FIG. 13 shows a provisional model (a schematic model of SPINK7 anti-inflammatory checkpoint). Loss of SPINK7 resulted in uncontrolled proteolytic activity including increased uPA and KLK5 activity which promoted impaired epithelial differentiation including down-regulation of SPINK5 and FLG and IBF which enabled dendritic cells (DC) to encounter luminal antigens and promote Th2 response. Restoring the controlled proteolytic activity by A1AT administration ameliorated the epithelial differentiation and barrier function. Loss of SPINK7 also promoted retention of NFATC1 in the nucleus and expression of pro-inflammatory cytokines from IL-8, G-CSF, GM-CSF, IL-15, IL-18, IL-16, SCF, TNFα and CCL2 which was partially NFATC1 dependent and can be blocked by the NFATC1 inhibitors CsA and FK506. In addition, a local increase in uPA activity facilitated eosinophil infiltration to the esophagus upon binding of uPA to uPAR.

Figure 14A:
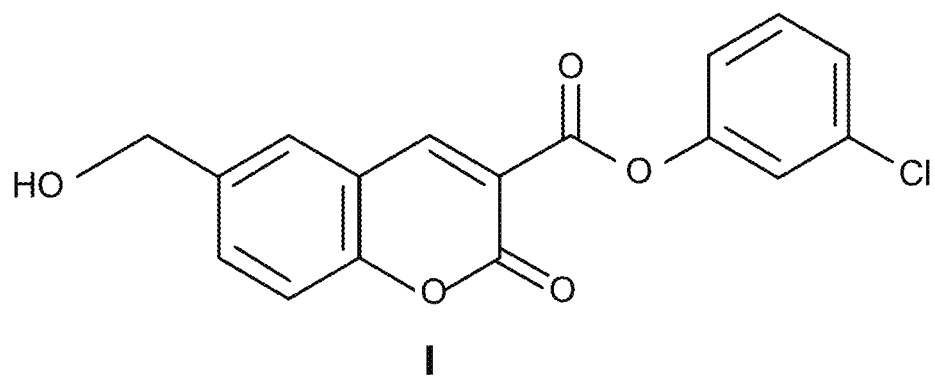
Figure 14B:
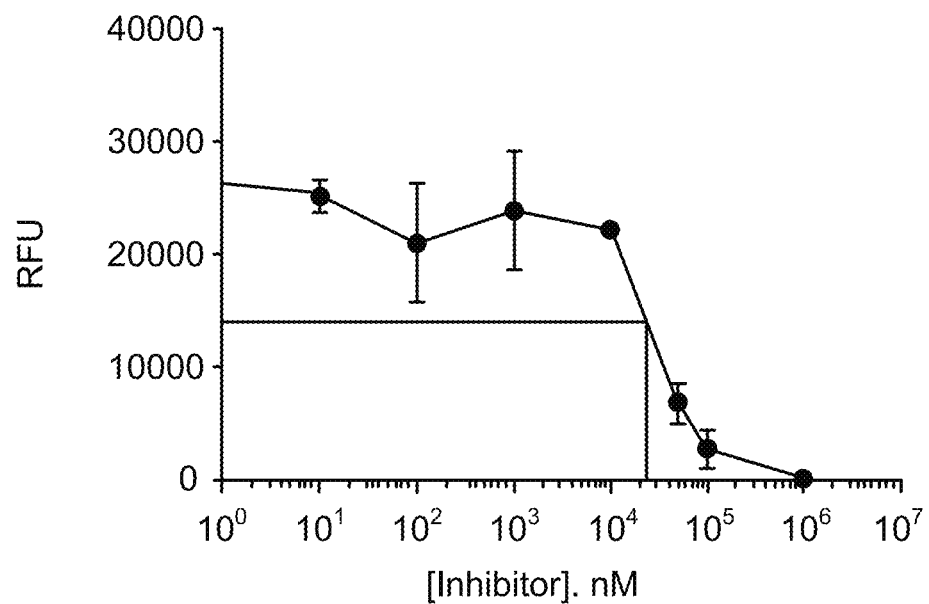
Figure 14C:
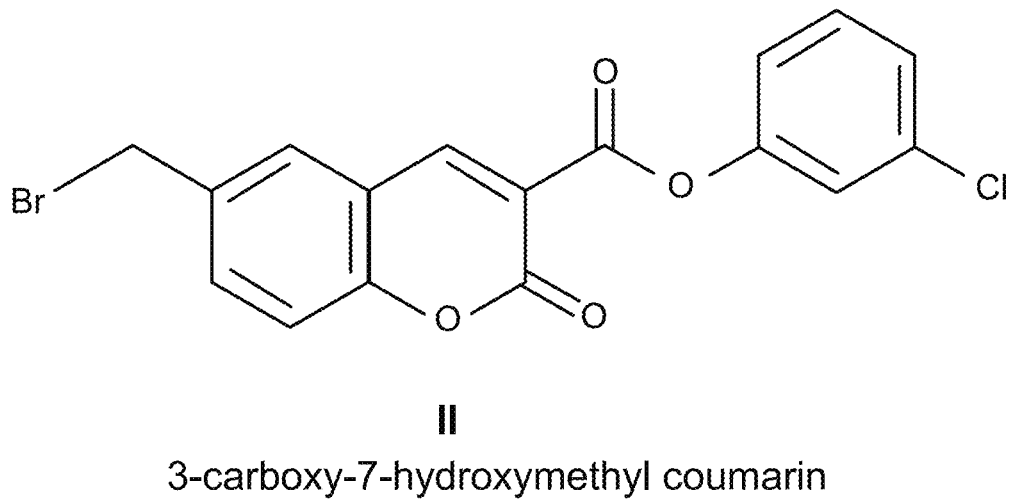
Figure 14D:
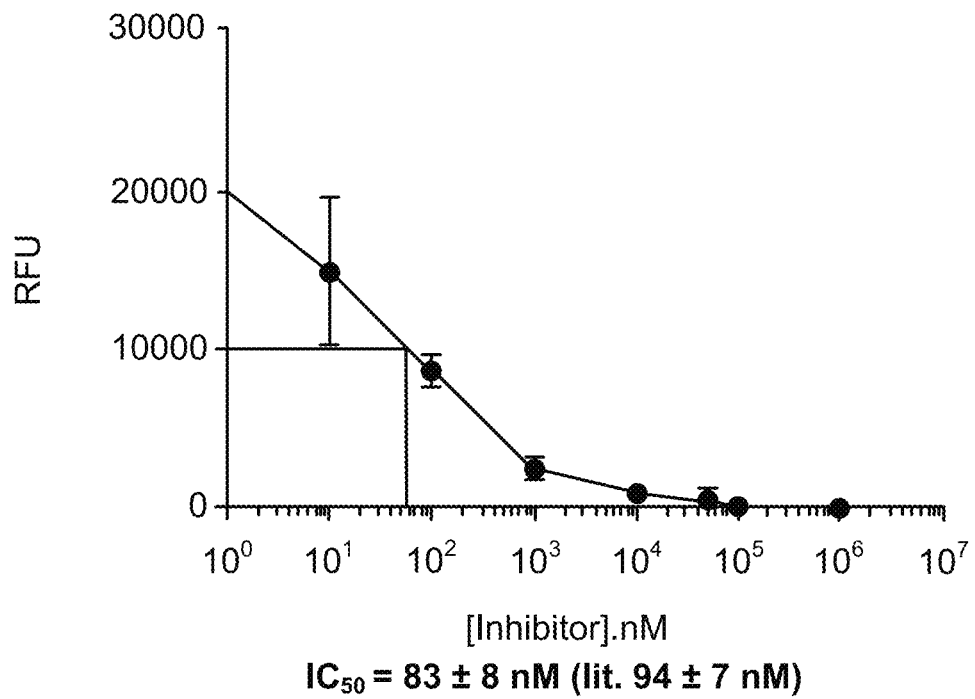

FIGS. 14A-14D show the effect of organic compounds on KLK5 activity. FIG. 14A is a structure of 3-(3-chlorophenyl) carboxy-7-hydroxymethyl coumarin. FIG. 14B is a dose response curve for 3-(3-chlorophenyl)carboxy-7-hydroxymethyl coumarin. FIG. 14C is a structure of 3-carboxy-7-hydroxymethyl coumarin. FIG. 14D is a dose response curve for 3-carboxy-7-hydroxymethyl coumarin.

DETAILED DESCRIPTION OF THE INVENTION

The methods described here are based, in part, on the identification of the serine proteinase inhibitor kazal-type 7 (SPINK7) as a key anti-inflammatory regulator which is lost in allergic inflammation of the squamous epithelium, for example as occurs in the esophageal tissue of patients suffering from EoE. EoE is historically defined as esophageal eosinophilia (EE) that does not respond to proton pump inhibitor (PPI) therapy. It is now apparent, however, that EoE overlaps with PPI-Responsive EE, such that both disease entities are now considered the same basic process (see, e.g., Proton pump inhibitor-responsive oesophageal eosinophilia: an entity challenging current diagnostic criteria for eosinophilic oesophagitis, Molina-Infante J et al., PPI-REE Task Force of the European Society of Eosinophilic Oesophagitis (EUREOS). Gut. 2016 March; 65(3): 524-31).

EoE can also be considered proteotypic for conditions characterized by inflammation of the squamous epithelium, particularly allergic inflammation. Also discovered by the present inventors is that the key molecular targets of SPINK7 include the proteinases urokinase type plasminogen activator (uPA) and kallikrein 5 (KLK5). The term "proteinase" is synonymous with the term "protease" and both terms refer to a proteolytic enzyme that acts on proteins and polypeptides by hydrolysis of peptide bonds.

The results described infra demonstrate that the loss of SPINK7 hampers esophageal barrier formation and promotes pro-inflammatory changes in epithelial cells. These pro-inflammatory changes are mediated by the uncontrolled proteolytic activity of uPA and KLK5, which are normally repressed by SPINK7. The resulting changes in the epithelial cells cause aberrant epithelial cell differentiation and impaired barrier function. These changes enable immune cells to encounter luminal antigens and promote a Th2 response. This provides the rationale for pharmacological targeting of uPA and KLK5 for the treatment of EoE, since inhibiting the proteolytic activity of these proteins would at least partially restore a key function of SPINK7 that is lost in the disease state, the downregulation of these proteinases. The data provided here further demonstrate that protein replacement with an alpha-1 anti-trypsin (A1AT) proteinase inhibitor restored some responses associated with loss of SPINK7 in vitro. This data supports the therapeutic potential of the methods described herein.

Thus, the methods described herein aim to reestablish SPINK7 checkpoint control in the squamous epithelium of a target tissue where that control has been lost or diminished, e.g., in tissues characterized by inflammation of the squamous epithelium, especially allergic inflammation. SPINK7 checkpoint control may be reestablished according to the present methods, for example, by increasing SPINK7 anti-proteinase activity directly, e.g., by replenishing SPINK7 protein in the target tissue, or indirectly, e.g., by introducing one or more serine proteinase inhibitors to the target tissue.

In embodiments, the methods described here may comprise introducing SPINK7 protein to a target tissue, for example by administering a recombinant polynucleotide encoding a SPINK7 protein, or by introducing a recombinant SPINK7 polypeptide. The methods may also comprise increasing the expression of endogenous SPINK7 in the target tissue.

In embodiments, the methods described here may also comprise administering one or more therapeutic agents that are proteinase inhibitors. In embodiments, the proteinase inhibitor is a serine proteinase inhibitor. In embodiments, the serine proteinase inhibitor is an inhibitor of an alpha-1 proteinase, a trypsin-like serine proteinase, a urokinase-type serine proteinase, or an inhibitor of uPA or KLK5, or any combination of the foregoing. In accordance with any of the foregoing embodiments, the therapeutic agent may be a small organic molecule, a polypeptide, or a nucleic acid. In embodiments, the small organic molecule is selected from the group consisting of the KLK5 inhibitors 3-(3-chlorophenyl)carboxy-7-hydroxymethyl coumarin and 3-carboxy-7-hydroxymethyl coumarin. In embodiments, the polypeptide is selected from the group consisting of an Fc fusion protein and an inhibitory antibody, e.g., targeted against uPA or KLK5, or both. In embodiments, the nucleic acid is selected from the group consisting of an anti-sense polynucleotide and an inhibitory RNA such as an miRNA or shRNA, e.g., targeted against uPA or KLK5, or both.

In embodiments, the therapeutic agent is an anti-KLK5-based therapeutic agent. In embodiments, the anti-KLK5 agent is a KLK5-Fc fusion protein, an KLK5 anti-sense polynucleotide, an KLK5-directed miRNA, an KLK5-directed shRNA, or a KLK5-directed antibody. In embodiments, the anti-KLK5-based therapeutic agent is a serine proteinase inhibitor. In embodiments, the anti-KLK5 agent is selected from 3-(3-chlorophenyl)carboxy-7-hydroxymethyl coumarin and 3-carboxy-7-hydroxymethyl coumarin.

In embodiments, the therapeutic agent may also include at least one of a compound or composition that suppresses uPA or KLK5 proteinase activity. In some embodiments, the compound or composition that suppresses uPA or KLK5 proteinase activity includes a proteinase inhibitor, an NTRK1-Fc fusion protein (neurotrophic receptor kinase 1), an NTRK1 anti-sense polynucleotide, an NTRK1-directed miRNA, an NTRK1-directed shRNA, or an NTRK1-directed antibody, including a humanized antibody.

In embodiments, uPA or KLK5 activity is suppressed by inhibiting uPA or KLK5 gene expression, inhibiting uPA or KLK5 protein expression, or inhibiting uPA or KLK5 proteinase activity, or any combination thereof. For example uPA or KLK5 proteinase activity may be inhibited directly, by an agent that inhibits the proteinase function of the protein, or indirectly, for example, by inhibiting gene or protein expression, thereby reducing the amount of uPA or KLK5 protein in the target tissue and thereby indirectly inhibiting uPA or KLK5 proteinase activity in the target tissue.

In embodiments, the therapeutic agent is a proteinase inhibitor. In embodiments, the therapeutic agent is a serine proteinase inhibitor. In embodiments, the therapeutic agent is an alpha-1 proteinase inhibitor. In embodiments, the alpha-1 proteinase inhibitor is a recombinant protein. In embodiments, the alpha-1 proteinase inhibitor is selected from PROLASTIN-C™, ZEMAIRA™, and ARALAST™.

In embodiments, the one or more therapeutic agents may be administered in the form of a pharmaceutical composition. The pharmaceutical composition may in any suitable form, as described in more detail infra.

In embodiments, the pharmaceutical composition is administered to the subject by any suitable route of administration. For example, the composition may be administered intravenously, intradermally, subcutaneously, or perorally. In embodiments, the pharmaceutical composition is administered to the subject by inhalation.

Methods of Treatment

The present disclosure provides methods for the treatment of an allergic inflammatory condition in a subject in need thereof, the allergic inflammatory condition characterized by inflammation of a squamous epithelium in a target tissue of the subject. In embodiments, the allergic inflammatory condition is EE or EoE. As discussed above the methods generally comprise increasing SPINK7 anti-proteinase activity either directly, e.g., by replenishing SPINK7 protein in the target tissue, or indirectly, e.g., by introducing one or more serine proteinase inhibitors to the target tissue.

In embodiments, an effective amount of a therapeutic agent is administered to the subject in need of treatment. In embodiments, the effective amount is a therapeutically effective amount. In embodiments, the effective amount is the amount effective to ameliorate one or more symptoms of an allergic inflammatory condition of the squamous epithelium. In embodiments, the effective amount is the amount effective to ameliorate one or more symptoms of EE or EoE. In embodiments, the effective amount is the amount effective to suppress KLK5 proteinase activity in a target tissue. In embodiments, the target tissue is esophageal tissue.

Also envisioned are methods comprising combination therapy for the treatment of an allergic inflammatory condition in a subject in need of such treatment. As used herein, "combination therapy" or "co-therapy" includes the administration of an effective amount of a primary therapeutic agent as described herein as part of a specific treatment regimen intended to provide the beneficial effect from the co-action of the primary therapeutic agent and an additional active agent, e.g., an additional active pharmaceutical ingredient (API). The beneficial effect of the combination includes, but is not limited to, pharmacokinetic or pharmacodynamic co-action resulting from the combination of therapeutic compounds. The beneficial effect of the combination may also relate to the mitigation of a toxicity, side effect, or adverse event associated with another agent in the combination. "Combination therapy" is not intended to encompass the administration of two or more of these therapeutic compounds as part of separate monotherapy regimens that incidentally and arbitrarily result in a beneficial effect that was not intended or predicted.

The at least one additional active agent may be a therapeutic agent, for example an anti-inflammatory agent, or a non-therapeutic agent, and combinations thereof. With respect to therapeutic agents, the beneficial effect of the combination includes, but is not limited to, pharmacokinetic or pharmacodynamic co-action resulting from the combination of therapeutically active compounds. With respect to nontherapeutic agents, the beneficial effect of the combination may relate to the mitigation of a toxicity, side effect, or adverse event associated with a therapeutically active agent in the combination.

Thus, in embodiments, the methods described here may further comprise administering to the subject at least one additional active agent. In embodiments, the at least one additional active agent is an anti-inflammatory agent. In embodiments, the at least one additional active agent is an IL-13 inhibitor, a non-steroidal anti-inflammatory drug (NSAID), a cytokine inhibitor, or a steroid. In embodiments, the at least one additional active agent is a proton pump inhibitor.

In the context of combination therapy, the administration of the primary therapeutic agent, may be simultaneous with or sequential to the administration of the one or more additional active agents. In another embodiment, administration of the different components of a combination therapy may be at different frequencies. The one or more additional agents may be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a primary therapeutic agent as described herein.

The one or more additional active agents can be formulated for co-administration with the primary therapeutic agent in a single dosage form. The one or more additional active agents can be administered separately from the dosage form that comprises the primary therapeutic agent. When the additional active agent is administered separately from the primary therapeutic agent, it can be by the same or a different route of administration as the primary therapeutic agent.

Preferably, the administration of a composition comprising the primary therapeutic agent in combination with one or more additional active agents provides a synergistic response in the subject being treated. In this context, the term "synergistic" refers to the efficacy of the combination being more effective than the additive effects of either single therapy alone. The synergistic effect of a combination therapy according to the disclosure can permit the use of lower dosages and/or less frequent administration of at least one agent in the combination compared to its dose and/or frequency outside of the combination. Additional beneficial effects of the combination can be manifested in the avoidance or reduction of adverse or unwanted side effects associated with the use of either therapy in the combination alone (also referred to as monotherapy).

"Combination therapy" also embraces the administration of the compounds of the present disclosure in further combination with non-drug therapies (e.g., diet modification). Where the combination therapy further comprises a non-drug treatment, the non-drug treatment may be conducted at any suitable time so long as a beneficial effect from the co-action of the combination of the therapeutic compounds and non-drug treatment is achieved. For example, in appropriate cases, the beneficial effect is still achieved when the non-drug treatment is temporally removed from the administration of the therapeutic compounds, perhaps by days or even weeks.

In embodiments, the amount of the therapeutic agent administered to the subject is a therapeutically effective amount. The term "therapeutically effective amount" refers to an amount sufficient to treat, ameliorate a symptom of, reduce the severity of, or reduce the duration of the disease or disorder being treated or enhance or improve the therapeutic effect of another therapy, or sufficient to exhibit a detectable therapeutic effect in the subject.

An effective amount of the therapeutic agent can be administered once or twice daily, from two to five times daily, up to two times or up to three times daily, or up to eight times daily.

In accordance with the methods described herein, a "subject in need thereof" is a subject having an allergic inflammatory condition characterized by inflammation of the squamous epithelium in a target tissue. In specific embodiments, the subject is a subject having EE or EoE.

A "subject" includes a mammal. The mammal can be any mammal, for example, a human, primate, vertebrate, bird, mouse, rat, fowl, dog, cat, cow, horse, goat, camel, sheep or a pig. Preferably, the subject is a human. The term "patient" refers to a human subject.

The present disclosure also provides a monotherapy for the treatment of EoE. As used herein, "monotherapy" refers to the administration of a single active or therapeutic compound, e.g., a proteinase inhibitor or an anti-KLK5-based therapeutic agent, to a subject in need thereof.

As used herein, "treatment", "treating" or "treat" describes the management and care of a patient for the purpose of combating a disease, condition, or disorder and includes the administration of a proteinase inhibitor or an anti-KLK5-based therapeutic agent to alleviate the symptoms or complications of the allergic inflammatory disease, disorder, or condition.

As used herein, "prevention", "preventing" or "prevent" describes reducing or eliminating the onset of the symptoms or complications of the allergic inflammatory disease, disorder, or condition and includes the administration of a proteinase inhibitor or an anti-KLK5-based therapeutic agent to reduce the onset, development or recurrence of symptoms of the disease, disorder, or condition.

In one embodiment, the administration of a proteinase inhibitor or an anti-KLK5-based therapeutic agent leads to the elimination of a symptom or complication of the disease or condition being treated, however elimination of the disease, disorder, or condition is not required. In one embodiment, the severity of the symptom is decreased.

Pharmaceutical Compositions and Formulations

The present disclosure provides pharmaceutical compositions comprising an amount of a therapeutic agent as described supra. For example, the therapeutic agent may comprise a recombinant polynucleotide encoding a SPINK7 protein, a recombinant SPINK7 polypeptide, or another agent effective to increase the expression and/or amount of endogenous SPINK7 mRNA and/or protein in the target tissue. The therapeutic agent may also be proteinase inhibitor and/or a specific inhibitor of uPA and/or KLK5.

In embodiments, the proteinase inhibitor, anti-uPA or anti-KLK5 based therapeutic agent is combined with at least one additional active agent in a single dosage form. In embodiments, the at least one additional active agent is selected from an anti-inflammatory agent selected from an IL-13 inhibitor, a non-steroidal anti-inflammatory drug (NSAID), a steroid, and a cytokine inhibitor, a PPI inhibitor, and combinations thereof.

A "pharmaceutical composition" is a formulation containing the therapeutic agent in a pharmaceutically acceptable form suitable for administration to a subject. As used herein, the phrase "pharmaceutically acceptable" refers to those compounds, materials, compositions, carriers, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

"Pharmaceutically acceptable excipient" means an excipient that is useful in preparing a pharmaceutical composition that is generally safe, non-toxic and neither biologically nor otherwise undesirable, and includes excipient that is acceptable for veterinary use as well as human pharmaceutical use. Examples of pharmaceutically acceptable excipients include, without limitation, sterile liquids, water, buffered saline, ethanol, polyol (for example, glycerol, propylene glycol, liquid polyethylene glycol and the like), oils, detergents, suspending agents, carbohydrates (e.g., glucose, lactose, sucrose or dextran), antioxidants (e.g., ascorbic acid or glutathione), chelating agents, low molecular weight proteins, or suitable mixtures thereof.

A pharmaceutical composition can be provided in bulk or in dosage unit form. It is especially advantageous to formulate pharmaceutical compositions in dosage unit form for ease of administration and uniformity of dosage. The term "dosage unit form" as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the disclosure are dictated by and directly dependent on the unique characteristics of the active compound and the particular therapeutic effect to be achieved. A dosage unit form can be an ampoule, a vial, a suppository, a dragee, a tablet, a capsule, an IV bag, or a single pump on an aerosol inhaler.

In therapeutic applications, the dosages vary depending on the agent, the age, weight, and clinical condition of the recipient subject or patient, and the experience and judgment of the clinician or practitioner administering the therapy, among other factors affecting the selected dosage. Generally, the dose should be a therapeutically effective amount. Dosages can be provided in mg/kg/day units of measurement (which dose may be adjusted for the patient's weight in kg, body surface area in m2, and age in years). An effective amount of a pharmaceutical composition is that which provides an objectively identifiable improvement as noted by the clinician or other qualified observer. For example, alleviating a symptom of a disorder, disease or condition. As used herein, the term "dosage effective manner" refers to amount of a pharmaceutical composition to produce the desired biological effect in a subject or cell.

For example, the dosage unit form can comprise 1 nanogram to 2 milligrams, or 0.1 milligrams to 2 grams; or from 10 milligrams to 1 gram, or from 50 milligrams to 500 milligrams or from 1 microgram to 20 milligrams; or from 1 microgram to 10 milligrams; or from 0.1 milligrams to 2 milligrams.

The pharmaceutical compositions can take any suitable form (e.g, liquids, aerosols, solutions, inhalants, mists, sprays; or solids, powders, ointments, pastes, creams, lotions, gels, patches and the like) for administration by any desired route (e.g., pulmonary, inhalation, intranasal, oral, buccal, sublingual, parenteral, subcutaneous, intravenous, intramuscular, intraperitoneal, intrapleural, intrathecal, transdermal, transmucosal, rectal, and the like). For example, a pharmaceutical composition of the disclosure may be in the form of an aqueous solution or powder for aerosol administration by inhalation or insufflation (either through the mouth or the nose), in the form of a tablet or capsule for oral administration; in the form of a sterile aqueous solution or dispersion suitable for administration by either direct injection or by addition to sterile infusion fluids for intravenous infusion; or in the form of a lotion, cream, foam, patch, suspension, solution, or suppository for transdermal or transmucosal administration.

A pharmaceutical composition may be in a form suitable for administration by inhalation, for example as an aqueous or non-aqueous aerosol, or as a dry powder. In embodiments, the pharmaceutical composition is an aqueous solution adapted for delivery via a nebulizer, including jet, vibrating mesh, and static mesh or orifice nebulizers. In embodiments, the pharmaceutical composition is a dry powder adapted for delivery via a dry powder inhaler device.

A pharmaceutical composition can be in the form of an orally acceptable dosage form including, but not limited to, capsules, tablets, buccal forms, troches, lozenges, and oral liquids in the form of emulsions, aqueous suspensions, dispersions or solutions. Capsules may contain mixtures of a compound of the present disclosure with inert fillers and/or diluents such as the pharmaceutically acceptable starches (e.g., corn, potato or tapioca starch), sugars, artificial sweetening agents, powdered celluloses, such as crystalline and microcrystalline celluloses, flours, gelatins, gums, etc. In the case of tablets for oral use, carriers which are commonly used include lactose and corn starch. Lubricating agents, such as magnesium stearate, can also be added. For oral administration in a capsule form, useful diluents include lactose and dried corn starch. When aqueous suspensions and/or emulsions are administered orally, the compound of the present disclosure may be suspended or dissolved in an oily phase is combined with emulsifying and/or suspending agents. If desired, certain sweetening and/or flavoring and/or coloring agents may be added.

A pharmaceutical composition can be in the form of a tablet. The tablet can comprise a unit dosage of a compound of the present disclosure together with an inert diluent or carrier such as a sugar or sugar alcohol, for example lactose, sucrose, sorbitol or mannitol. The tablet can further comprise a non-sugar derived diluent such as sodium carbonate, calcium phosphate, calcium carbonate, or a cellulose or derivative thereof such as methyl cellulose, ethyl cellulose, hydroxypropyl methyl cellulose, and starches such as corn starch. The tablet can further comprise binding and granulating agents such as polyvinylpyrrolidone, disintegrants (e.g. swellable crosslinked polymers such as crosslinked carboxymethylcellulose), lubricating agents (e.g. stearates), preservatives (e.g. parabens), antioxidants (e.g. BHT), buffering agents (for example phosphate or citrate buffers), and effervescent agents such as citrate/bicarbonate mixtures.

The tablet can be a coated tablet. The coating can be a protective film coating (e.g. a wax or varnish) or a coating designed to control the release of the active agent, for example a delayed release (release of the active after a predetermined lag time following ingestion) or release at a particular location in the gastrointestinal tract. The latter can be achieved, for example, using enteric film coatings such as those sold under the brand name Eudragit®.

Tablet formulations may be made by conventional compression, wet granulation or dry granulation methods and utilize pharmaceutically acceptable diluents, binding agents, lubricants, disintegrants, surface modifying agents (including surfactants), suspending or stabilizing agents, including, but not limited to, magnesium stearate, stearic acid, talc, sodium lauryl sulfate, microcrystalline cellulose, carboxymethylcellulose calcium, polyvinylpyrrolidone, gelatin, alginic acid, acacia gum, xanthan gum, sodium citrate, complex silicates, calcium carbonate, glycine, dextrin, sucrose, sorbitol, dicalcium phosphate, calcium sulfate, lactose, kaolin, mannitol, sodium chloride, talc, dry starches and powdered sugar. Preferred surface modifying agents include nonionic and anionic surface modifying agents. Representative examples of surface modifying agents include, but are not limited to, poloxamer 188, benzalkonium chloride, calcium stearate, cetostearyl alcohol, cetomacrogol emulsifying wax, sorbitan esters, colloidal silicon dioxide, phosphates, sodium dodecylsulfate, magnesium aluminum silicate, and triethanolamine.

A pharmaceutical composition can be in the form of a hard or soft gelatin capsule. In accordance with this formulation, the compound of the present disclosure may be in a solid, semi-solid, or liquid form.

A pharmaceutical composition can be in the form of a sterile aqueous solution or dispersion suitable for parenteral administration. The term parenteral as used herein includes subcutaneous, intracutaneous, intravenous, intramuscular, intra-articular, intraarterial, intrasynovial, intrastemal, intrathecal, intralesional and intracranial injection or infusion techniques.

A pharmaceutical composition can be in the form of a sterile aqueous solution or dispersion suitable for administration by either direct injection or by addition to sterile infusion fluids for intravenous infusion, and comprises a solvent or dispersion medium containing, water, ethanol, a polyol (e.g., glycerol, propylene glycol and liquid polyethylene glycol), suitable mixtures thereof, or one or more vegetable oils. Solutions or suspensions of the compound of the present disclosure as a free base or pharmacologically acceptable salt can be prepared in water suitably mixed with a surfactant. Examples of suitable surfactants are given below. Dispersions can also be prepared, for example, in glycerol, liquid polyethylene glycols and mixtures of the same in oils.

The pharmaceutical compositions for use in the methods of the present disclosure can further comprise one or more additives in addition to any carrier or diluent (such as lactose or mannitol) that is present in the formulation. The one or more additives can comprise or consist of one or more surfactants. Surfactants typically have one or more long aliphatic chains such as fatty acids which enables them to insert directly into the lipid structures of cells to enhance drug penetration and absorption. An empirical parameter commonly used to characterize the relative hydrophilicity and hydrophobicity of surfactants is the hydrophilic-lipophilic balance ("HLB" value). Surfactants with lower HLB values are more hydrophobic, and have greater solubility in oils, while surfactants with higher HLB values are more hydrophilic, and have greater solubility in aqueous solutions. Thus, hydrophilic surfactants are generally considered to be those compounds having an HLB value greater than about 10, and hydrophobic surfactants are generally those having an HLB value less than about 10. However, these HLB values are merely a guide since for many surfactants, the HLB values can differ by as much as about 8 HLB units, depending upon the empirical method chosen to determine the HLB value.

Among the surfactants for use in the compositions of the disclosure are polyethylene glycol (PEG)-fatty acids and PEG-fatty acid mono and diesters, PEG glycerol esters, alcohol-oil transesterification products, polyglyceryl fatty acids, propylene glycol fatty acid esters, sterol and sterol derivatives, polyethylene glycol sorbitan fatty acid esters, polyethylene glycol alkyl ethers, sugar and its derivatives, polyethylene glycol alkyl phenols, polyoxyethylene-polyoxypropylene (POE-POP) block copolymers, sorbitan fatty acid esters, ionic surfactants, fat-soluble vitamins and their salts, water-soluble vitamins and their amphiphilic derivatives, amino acids and their salts, and organic acids and their esters and anhydrides.

The present disclosure also provides packaging and kits comprising pharmaceutical compositions for use in the methods of the present disclosure. The kit can comprise one or more containers selected from the group consisting of a bottle, a vial, an ampoule, a blister pack, and a syringe. The kit can further include one or more of instructions for use in treating and/or preventing a disease, condition or disorder of the present disclosure, one or more syringes, one or more applicators, or a sterile solution suitable for reconstituting a pharmaceutical composition of the present disclosure.

All percentages and ratios used herein, unless otherwise indicated, are by weight. Other features and advantages of the present disclosure are apparent from the different examples. The provided examples illustrate different components and methodology useful in practicing the present disclosure. The examples do not limit the claimed disclosure. Based on the present disclosure the skilled artisan can identify and employ other components and methodology useful for practicing the present disclosure.

EXAMPLES

The following non-limiting examples are provided to further illustrate embodiments of the invention disclosed herein. It will be appreciated by those of skill in the art that the techniques disclosed in the examples that follow represent approaches that have been found to function well in the practice of the invention and thus can be considered to constitute examples of modes for its practice. However, those of skill in the art will, in light of the present disclosure, appreciate that many changes can be made in the specific embodiments that are disclosed and still obtain a like or similar result without departing from the spirit and scope of the invention.

SUMMARY

As described more fully below, we show that the serine peptidase inhibitor kazal-type 7 (SPINK7) is an important anti-inflammatory check in the esophageal epithelium and is markedly down-regulated in eosinophilic esophagitis (EoE), an inflammatory TH2 type immune disease of the esophagus, while being expressed at relatively high levels in normal esophageal epithelium. We further show that loss of SPINK7 results in an epithelial cell differentiation defect, reduced barrier protein expression, impaired barrier function, and pro-inflammatory cytokine production. Protein replacement with an alpha-1 anti-trypsin proteinase inhibitor restored some responses associated with loss of SPINK7 in vitro. Our data show that the endogenous balance between SPINK7 and its target proteinases (uPA and KLK5) is a key checkpoint in regulating mucosal differentiation, barrier function and Th2-associated responses. Moreover, our data suggest that protein replacement with proteinase inhibitors holds therapeutic promise.

To investigate the role of SPINK7 in EoE, an in vitro system of human esophageal epithelial cells that were subjected to air-liquid interface (ALI) to induce squamous cell differentiation was used. Cells were stably transduced with either non-silencing control or SPINK7 shRNAs. The integrity of the epithelium was examined by barrier function assays complemented by histological and ultrastractural analyses and immune-fluorescence of junctional proteins. Proteinase activity, transcriptional alterations and identification SPINK7's downstream targets were also assessed. Cytokine and chemokine secretion was analyzed after SPINK7 gene silencing. The results demonstrated that SPINK7 was a key anti-inflammatory checkpoint in the esophageal epithelium.

The results showed that depletion of SPINK7 in esophageal epithelial cells induced architectural changes in esophageal epithelial cells reminiscent of those observed in patients with EoE including acantholysis and epithelial cleft formation, as well as impaired barrier function. The loss of SPINK7 also increased trypsin-like (>2 fold increase; $P=0.004$) and urokinase-type plasminogen activator (uPA) activity (2-fold, $P=006$). In vitro, SPINK7 inhibited the serine proteinase-kallikrein (KLK)5, but not KLK7 nor KLK11.

KLK5 is known to be involved in the regulation of the skin barrier. Furthermore, loss of SPINK7 was sufficient for induction of architectural alterations in junctional complexes, loss of ultrastructural zipper-like intercellular junctions, delocalization of the junctional proteins E-cadherin, β-catenin and desmoglein-1, decreased expression of the barrier protein filaggrin, as well as impaired barrier function.

In addition, SPINK7-depleted epithelial cells over-expressed a unique set of cytokines and chemokines that promote immune responses. Loss of SPINK7 unleashed the production of a series of pro-inflammatory cytokines and chemokines including TSLP, GM-CSF, TNFα, and IL-8. RNA sequencing substantiated that loss of SPINK7 was an upstream event in eliciting innate immune responses and cellular changes characteristic of inflammatory diseases of the epithelium.

Finally, a genetic interaction between SPINK7, TSLP and PLAU in EoE patients was identified, further linking SPINK7 to allergic responses. Epistasis between genetic variants in the SPINK, TSLP and PLAU loci were shown to contribute to EoE susceptibility. Susceptibility for EoE was impacted by epistasis between genetic variants in SPINK7 and PLAU (gene product uPA) with atopy risk variants in ST2 and TSLP.

Collectively, the data demonstrate that deficiency of SPINK7 in epithelial cells induces a profound pro-inflammatory state characterized by impaired barrier function, defect in cellular differentiation, and cytokine production. Combined with genetic interaction between SPINK and TSLP, the endogenous balance between the natural proteinase inhibitor SPINK7 and proteinases (uPA and KLK5) is a key checkpoint in regulating mucosal Th2-associated immune responses.

Example 1: Specific SPINK7 Expression in Eosinophilic Esophagitis (EoE)

Of 8 SPINK members expressed in the esophagus; the most highly expressed were SPINK5 and SPINK7 (1450 and 831 FPKM, respectively) based on genome wide RNA sequencing data of the human esophagus (data not shown, shows the normalized FPKM values for SPINKs expression in healthy and EoE patients from RNAseq data of esophageal biopsies from 6 healthy controls (Normal), and 10 patients with active EoE) (Sherrill, J. D. et al. *Genes and immunity* 15, 361-369 (2014)). SPINK7 FPKM value was >150-fold greater than SPINK8 (5 FPKM), which was the most highly expressed SPINK besides SPINK5 and SPINK7. Four of the 8 expressed SPINKs were decreased in EoE with SPINK7 showing the most statistically significant downregulation (16-fold reduction; $p=3\times10^{-8}$) compared to control (data not shown).

Analysis of esophageal biopsies (n=133 patients) demonstrated that SPINK7 mRNA was down regulated in EoE compared to controls (data not shown) (Wen, T. et al. *Gastroenterology* 145, 1289-1299 (2013)). Microarray data of esophageal biopsies from 14 healthy controls (Normal), 22 patients with inactive or 19 patients with active EoE was also performed (data not shown). This was further validated by quantitative PCR (data not shown).

Figure 1:
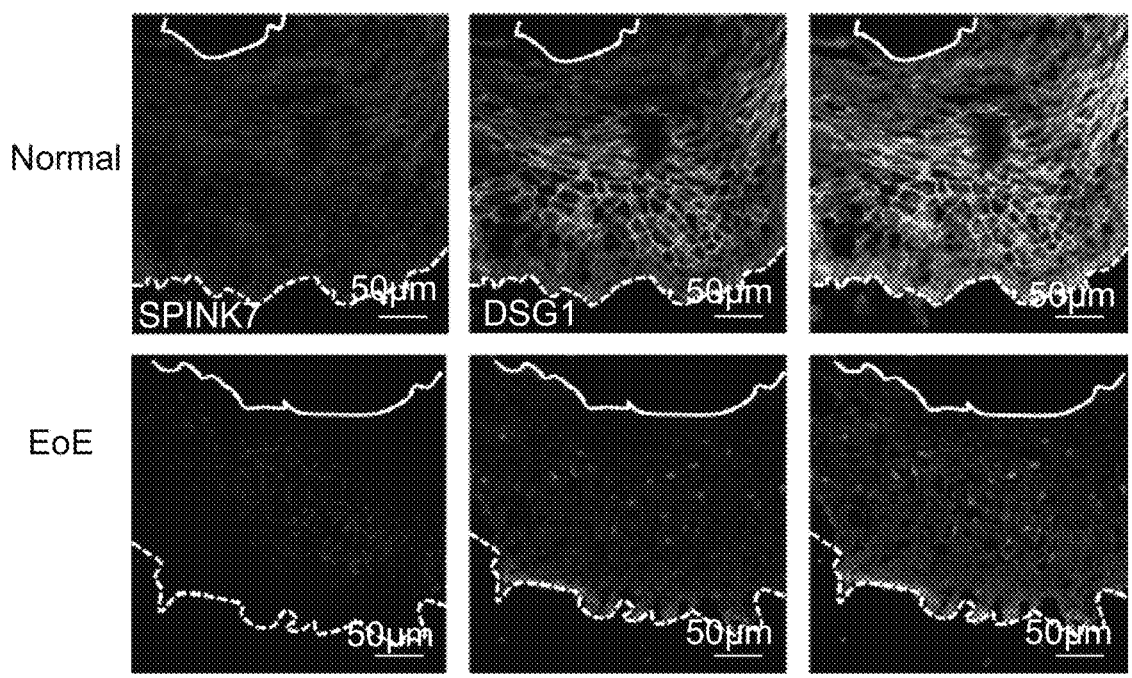
FIG. 1 shows immunofluorescence staining images of esophageal biopsy sections for DSG1 and SPINK7 with DAPI-stained nuclei; representative images of control patients (Normal) and patients with EoE (EoE) are shown. A solid line separates the lumen from the epithelium, and a dashed line separates the epithelium from the lamina propria.

Confocal microscopy revealed SPINK7 expression throughout all epithelial layers with the highest expression in the suprabasal epithelium and its expression was significantly down-regulated together with DSG1 in EoE patients compared to control individuals (FIG. 1). There was a positive correlation between SPINK7 and epithelial products including differentiation and adhesion molecules and a negative correlation between SPINK7 and cytokines such as IL-5 and CCL26 (data not shown), demonstrating that the loss of SPINK7 might regulate epithelial integrity and promote increased inflammatory response.

Figure 2:
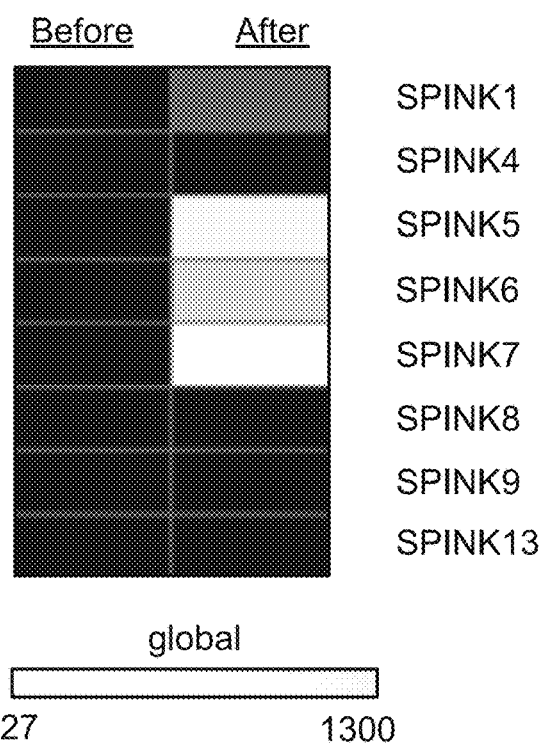
FIG. 2 shows a heat map of SPINKs expression before differentiation of EPC2 cells (day 0) or after 14 days of ALI differentiation.

Example 2: SPINK Expression is Part of the Epithelial Differentiation Program Epithelial differentiation was induced by culture of either an esophageal epithelial progenitor cell line (EPC2) or primary esophageal epithelial cells exposed to the air-liquid interface (ALI), as reported (Sherrill, J. D. et al. *Mucosal immunology* 7, 718-729 (2014), Kalabis, J. et al. *Nature protocols* 7, 235-246 (2012), and Frankart, A. et al. *Experimental dermatology* 21, 871-875 (2012)). Under these conditions, the expression of SPINK5 and SPINK7 increased by 915-fold and 752-fold, respectively ($p=0.0007$, $p<10^{-10}$, respectively). SPINK5 and SPINK7 were the most highly expressed SPINK family members following epithelial cell differentiation in vitro (FIG. 2), consistent with the in vivo expression pattern.

Example 3: Loss of SPINK7 Impairs Epithelial Differentiation

SPINK7 expression was silenced specifically by shRNAi targeting a region of SPINK7 that exhibited relatively less conservation with SPINK5 which on average exhibits 51% identity to SPINK7 (data not shown). EPC2 cells and primary esophageal epithelial cells were stably transduced with vector expressing either shRNA target SPINK7 or non-silencing control (NSC) shRNA. In cells expressing the SPINK7-directed shRNA, near complete loss of SPINK7 expression was observed with no effect on SPINK5, indicating specificity of the gene silencing construct (data not shown).

Whole transcriptome sequencing analysis was performed on EPC2 cells after ALI differentiation (data not shown). This analysis revealed 270 genes that were differentially expressed in the SPINK7-deficient cells compared to NSC cells ($p<0.05$, fold change>2, RPKM>1) (Table 1, below). The modified genes were enriched for those involved in epidermal differentiation and inflammation including the transcription factors STAT1 and NFATC2 and cytokines such as IL23, IL37, and CCL24 and included decreased expression of FLG, FLG2, LOR, keratins, tranglutaminases and interleukin 36 receptor antagonist (IL36RN) (data not shown and Table 1). Functionally, it was predicted that loss of SPINK7 regulated innate immune responses and interferon regulatory factors (data not shown).

TABLE 1

Transcriptomic analysis of genes differentially expressed after SPINK7-silencing compared to control in differentiated EPC2 cells

| Gene_ID | RPKM Control | RPKM SPINK7 | Fold Change | p-value |
|---|---|---|---|---|
| AADACL2 | 8.660 | 0.353 | 0.041 | 3.12E-10 |
| ABCG4 | 1.252 | 0.292 | 0.233 | 0.001276785 |
| ABHD12B | 1.025 | 0.217 | 0.212 | 0.000227346 |
| ABP1 | 6.362 | 0.491 | 0.077 | 2.62E-08 |
| ACER1 | 10.451 | 1.513 | 0.145 | 5.26E-13 |
| ACP5 | 3.783 | 1.509 | 0.399 | 0.000721352 |
| ACPP | 9.356 | 3.554 | 0.380 | 2.79E-06 |
| ALDH1A3 | 200.888 | 675.867 | 3.364 | 1.95E-10 |
| ALDH5A1 | 1.778 | 0.651 | 0.366 | 0.000678249 |
| ALOX12B | 17.886 | 5.411 | 0.303 | 7.18E-05 |
| ANKRD35 | 8.693 | 2.993 | 0.344 | 8.95E-06 |
| APOE | 22.695 | 5.167 | 0.228 | 0.001409301 |
| AQP3 | 70.172 | 34.698 | 0.494 | 0.000320651 |
| ARL4A | 10.506 | 3.386 | 0.322 | 0.000103552 |
| ASAP3 | 7.982 | 2.973 | 0.372 | 1.37E-07 |
| ASPG | 3.398 | 0.462 | 0.136 | 0.000822682 |
| ASPRV1 | 22.411 | 0.570 | 0.025 | 9.80E-29 |
| BCAS1 | 6.504 | 0.615 | 0.095 | 9.62E-05 |
| BGN | 0.535 | 1.463 | 2.735 | 0.004746858 |
| BNIPL | 27.186 | 12.137 | 0.446 | 0.000101291 |
| BST2 | 4.337 | 46.397 | 10.697 | 2.01E-21 |
| C10orf10 | 2.086 | 3.710 | 1.779 | 5.88E-05 |
| C10orf99 | 89.123 | 23.786 | 0.267 | 3.08E-09 |
| C17orf109 | 1.834 | 0.297 | 0.162 | 0.000325599 |
| C19orf66 | 5.604 | 16.880 | 3.012 | 0.001476392 |
| C1orf68 | 3.792 | 0.177 | 0.047 | 1.67E-14 |
| C2orf54 | 12.718 | 2.398 | 0.189 | 8.82E-06 |
| C5orf46 | 17.411 | 2.016 | 0.116 | 5.67E-07 |
| C6orf15 | 22.207 | 6.762 | 0.305 | 4.70E-11 |
| CA13 | 1.737 | 0.749 | 0.431 | 0.001446637 |
| CALB2 | 10.486 | 4.100 | 0.391 | 0.00031438 |
| CALML5 | 49.497 | 4.000 | 0.081 | 6.89E-15 |
| CAMK1D | 1.690 | 0.582 | 0.344 | 0.001481232 |
| CASP14 | 11.974 | 0.941 | 0.079 | 8.46E-31 |
| CCL24 | 3.902 | 0.074 | 0.019 | 1.27E-05 |
| CDH26 | 1.359 | 0.337 | 0.248 | 3.76E-05 |
| CEACAM5 | 24.091 | 2.054 | 0.085 | 1.62E-14 |
| CEACAM7 | 10.835 | 0.495 | 0.046 | 3.64E-05 |
| CERCAM | 3.872 | 8.326 | 2.150 | 0.000384542 |
| CERS4 | 20.319 | 8.394 | 0.413 | 0.000100833 |
| CHRNB1 | 2.566 | 6.303 | 2.457 | 0.000303905 |
| CLCA4 | 35.921 | 3.034 | 0.084 | 0.003852654 |
| CLDN17 | 108.849 | 49.550 | 0.455 | 0.005591202 |
| CLDN4 | 35.014 | 71.975 | 2.056 | 0.000880654 |
| CMPK2 | 3.097 | 18.705 | 6.039 | 1.21E-06 |
| CMTM8 | 2.033 | 0.754 | 0.371 | 0.002603997 |
| CORO6 | 0.597 | 1.792 | 3.000 | 0.000206577 |
| CPPED1 | 5.802 | 1.148 | 0.198 | 2.67E-12 |
| CRISP3 | 12.852 | 0.217 | 0.017 | 0.000162726 |
| CSF2RB | 1.931 | 0.592 | 0.306 | 0.003264803 |
| CSGALNACT1 | 5.004 | 2.257 | 0.451 | 0.000148176 |
| CXCL14 | 106.453 | 52.935 | 0.497 | 2.68E-06 |
| CXCL17 | 12.814 | 1.546 | 0.121 | 0.000343615 |
| CXCR2 | 2.104 | 0.796 | 0.378 | 0.001546073 |
| CYP2C18 | 15.091 | 6.752 | 0.447 | 1.79E-05 |
| CYP4B1 | 10.572 | 0.701 | 0.066 | 2.85E-15 |
| CYP4F11 | 0.253 | 1.372 | 5.423 | 9.65E-05 |
| CYP4F22 | 6.983 | 1.593 | 0.228 | 3.91E-07 |
| DACT2 | 0.164 | 1.356 | 8.269 | 1.16E-08 |

TABLE 1-continued

Transcriptomic analysis of genes differentially expressed after SPINK7-silencing compared to control in differentiated EPC2 cells

| Gene_ID | RPKM Control | RPKM SPINK7 | Fold Change | p-value |
|---|---|---|---|---|
| DAPL1 | 9.630 | 1.303 | 0.135 | 1.23E−07 |
| DDX58 | 8.009 | 31.227 | 3.899 | 0.00063373 |
| DDX60L | 5.122 | 21.791 | 4.254 | 3.76E−05 |
| DGAT2 | 26.942 | 8.160 | 0.303 | 9.38E−07 |
| DHX58 | 1.742 | 4.709 | 2.704 | 0.002056853 |
| DIO2 | 8.295 | 0.638 | 0.077 | 1.31E−05 |
| DSC1 | 19.955 | 0.412 | 0.021 | 1.16E−88 |
| DSG1 | 196.343 | 36.276 | 0.185 | 1.40E−20 |
| DTX3L | 6.590 | 22.720 | 3.448 | 0.000215309 |
| EIF2AK2 | 9.327 | 29.432 | 3.155 | 0.00059743 |
| ENTPD2 | 1.248 | 3.743 | 3.000 | 0.000431713 |
| EPHA4 | 8.987 | 2.517 | 0.280 | 4.79E−10 |
| EPHB6 | 1.121 | 0.401 | 0.358 | 0.000982833 |
| EPHX1 | 10.980 | 4.997 | 0.455 | 0.000148811 |
| EPS8 | 1.132 | 4.527 | 3.998 | 0.001324941 |
| EPSTI1 | 2.301 | 14.709 | 6.391 | 1.49E−06 |
| ERP27 | 2.173 | 0.475 | 0.219 | 8.93E−05 |
| FABP5 | 474.430 | 213.745 | 0.451 | 1.09E−05 |
| FAM3D | 28.282 | 2.147 | 0.076 | 2.78E−06 |
| FAM40B | 2.439 | 5.374 | 2.204 | 0.002121605 |
| FAM83C | 1.187 | 0.268 | 0.226 | 2.81E−05 |
| FCRLA | 0.313 | 1.057 | 3.375 | 0.004394847 |
| FETUB | 10.757 | 0.296 | 0.028 | 8.13E−14 |
| FLG | 16.017 | 1.814 | 0.113 | 1.33E−32 |
| FLG2 | 33.534 | 0.625 | 0.019 | 1.14E−58 |
| FLVCR2 | 11.514 | 4.513 | 0.392 | 7.86E−08 |
| FUOM | 3.130 | 0.919 | 0.294 | 0.007959923 |
| GBP1 | 6.595 | 15.532 | 2.355 | 0.00358778 |
| GCNT3 | 33.422 | 8.056 | 0.241 | 0.000598123 |
| GJB6 | 128.769 | 53.132 | 0.413 | 2.39E−06 |
| GLA | 28.411 | 11.992 | 0.422 | 0.000244569 |
| GPLD1 | 2.115 | 0.512 | 0.242 | 1.10E−05 |
| GPR111 | 1.087 | 0.359 | 0.330 | 7.52E−05 |
| GPRIN2 | 1.144 | 0.165 | 0.144 | 0.000662353 |
| GSTA4 | 16.732 | 6.224 | 0.372 | 2.12E−05 |
| GUCY1A3 | 4.661 | 1.665 | 0.357 | 0.000244799 |
| HAL | 2.715 | 0.163 | 0.060 | 3.72E−29 |
| HERC5 | 1.420 | 4.324 | 3.045 | 0.003040819 |
| HERC6 | 6.827 | 31.523 | 4.618 | 5.00E−06 |
| HEXA | 14.359 | 3.140 | 0.219 | 1.67E−08 |
| HLA-A | 64.534 | 156.953 | 2.432 | 1.12E−06 |
| HLA-B | 77.075 | 217.200 | 2.818 | 5.00E−08 |
| HLA-C | 44.366 | 105.895 | 2.387 | 2.37E−05 |
| HLA-F | 6.775 | 19.874 | 2.934 | 1.88E−05 |
| HOPX | 1132.244 | 344.550 | 0.304 | 0.000505595 |
| HPGD | 40.814 | 11.103 | 0.272 | 0.008896222 |
| HS3ST6 | 5.377 | 1.160 | 0.216 | 5.44E−05 |
| HYAL4 | 2.019 | 0.523 | 0.259 | 0.000599287 |
| IFI27 | 172.272 | 556.810 | 3.232 | 1.09E−07 |
| IFI35 | 5.633 | 25.363 | 4.502 | 2.46E−05 |
| IFI44 | 19.200 | 90.249 | 4.700 | 2.05E−06 |
| IFI44L | 1.920 | 25.357 | 13.210 | 1.68E−10 |
| IFI6 | 66.483 | 434.423 | 6.534 | 4.58E−12 |
| IFIH1 | 9.872 | 33.182 | 3.361 | 6.38E−06 |
| IFIT1 | 26.543 | 231.184 | 8.710 | 8.67E−07 |
| IFIT2 | 2.513 | 10.464 | 4.164 | 0.000772178 |
| IFIT3 | 13.555 | 85.022 | 6.272 | 8.89E−06 |
| IFIT5 | 5.205 | 16.352 | 3.142 | 9.23E−06 |
| IFITM1 | 42.317 | 156.612 | 3.701 | 1.08E−07 |
| IFITM3 | 127.955 | 312.570 | 2.443 | 7.41E−06 |
| IFNK | 0.570 | 10.002 | 17.540 | 7.94E−10 |
| IGFBP2 | 11.995 | 4.819 | 0.402 | 0.000117061 |
| IGFL2 | 171.138 | 49.633 | 0.290 | 3.37E−08 |
| IGFL3 | 14.557 | 7.769 | 0.534 | 0.001665316 |
| IL1F10 | 3.103 | 0.894 | 0.288 | 0.001679465 |
| IL23A | 13.831 | 3.996 | 0.289 | 0.002157056 |
| IL36B | 2.940 | 0.640 | 0.218 | 8.71E−05 |
| IL36RN | 51.959 | 10.819 | 0.208 | 1.28E−07 |
| IL37 | 1.898 | 0.271 | 0.143 | 0.002081829 |
| IRF7 | 5.425 | 21.631 | 3.987 | 1.82E−05 |
| ISG15 | 60.183 | 239.167 | 3.974 | 6.01E−05 |
| KLK1 | 1.831 | 0.489 | 0.267 | 0.001107183 |
| KLK12 | 46.708 | 14.034 | 0.300 | 0.001227423 |
| KLK5 | 197.057 | 480.144 | 2.437 | 9.30E−09 |
| KPRP | 31.654 | 10.894 | 0.344 | 5.07E−08 |
| KRT10 | 1006.965 | 62.168 | 0.062 | 5.27E−14 |
| KRT19 | 340.813 | 666.430 | 1.955 | 0.001106237 |
| KRT2 | 16.754 | 1.845 | 0.110 | 1.18E−07 |
| KRT23 | 195.775 | 93.248 | 0.476 | 0.00690264 |
| KRT24 | 2.346 | 3.062 | 1.306 | 7.22E−05 |
| KRT27 | 3.380 | 0.312 | 0.092 | 4.64E−09 |
| KRT4 | 460.140 | 54.598 | 0.119 | 9.88E−10 |
| KRT79 | 1.505 | 0.520 | 0.346 | 0.005201351 |
| KRTDAP | 2272.468 | 139.936 | 0.062 | 6.55E−24 |
| LAMP3 | 1.053 | 5.514 | 5.235 | 1.49E−05 |
| LCE1A | 64.188 | 17.932 | 0.279 | 1.92E−06 |
| LCE1C | 45.575 | 5.458 | 0.120 | 2.18E−13 |
| LCE1D | 23.419 | 2.908 | 0.124 | 3.98E−09 |
| LCE1E | 15.082 | 1.425 | 0.094 | 3.73E−10 |
| LCE2A | 36.115 | 8.891 | 0.246 | 1.42E−05 |
| LCE2B | 72.175 | 12.031 | 0.167 | 1.64E−11 |
| LCE2C | 71.599 | 21.581 | 0.301 | 4.29E−06 |
| LCE2D | 43.298 | 18.662 | 0.431 | 0.000129137 |
| LCP1 | 1.212 | 7.302 | 6.024 | 1.47E−05 |
| LGALS7B | 22.811 | 8.105 | 0.355 | 0.000816353 |
| LIPK | 11.476 | 3.990 | 0.348 | 7.60E−06 |
| LIPM | 20.570 | 3.419 | 0.166 | 1.29E−06 |
| LOR | 24.228 | 2.071 | 0.085 | 1.31E−19 |
| LY6D | 16.071 | 3.964 | 0.247 | 9.66E−10 |
| LY6G6C | 41.299 | 8.997 | 0.218 | 8.14E−12 |
| LYNX1 | 516.559 | 162.668 | 0.315 | 0.000447521 |
| LYPD2 | 157.658 | 30.035 | 0.191 | 0.000101254 |
| MAFB | 1.507 | 5.373 | 3.565 | 4.90E−08 |
| MAL | 67.102 | 2.602 | 0.039 | 8.47E−06 |
| MARCH3 | 1.206 | 0.578 | 0.479 | 0.000504864 |
| MFAP3L | 2.372 | 0.892 | 0.376 | 0.001286441 |
| MT1X | 441.374 | 169.262 | 0.383 | 3.19E−05 |
| MUC15 | 21.341 | 6.225 | 0.292 | 0.001802868 |
| MX1 | 31.721 | 194.408 | 6.129 | 2.22E−06 |
| MX2 | 3.081 | 39.028 | 12.667 | 1.03E−05 |
| MYH14 | 1.521 | 0.184 | 0.121 | 0.000132386 |
| MYL9 | 9.824 | 35.926 | 3.657 | 0.000205203 |
| MYZAP | 20.038 | 8.381 | 0.418 | 1.95E−05 |
| NEBL | 14.833 | 4.070 | 0.274 | 2.62E−06 |
| NFATC2 | 1.484 | 0.557 | 0.375 | 7.22E−08 |
| NLRC5 | 0.594 | 2.995 | 5.042 | 0.000136269 |
| OAS1 | 32.972 | 95.846 | 2.907 | 7.35E−05 |
| OAS2 | 26.204 | 105.856 | 4.040 | 7.77E−05 |
| OAS3 | 6.712 | 42.148 | 6.279 | 5.04E−06 |
| OASL | 5.341 | 18.148 | 3.398 | 0.00072384 |
| OPHN1 | 0.856 | 2.336 | 2.730 | 0.000195346 |
| PAQR5 | 3.609 | 1.586 | 0.439 | 3.46E−06 |
| PARP10 | 1.734 | 5.896 | 3.401 | 0.002403439 |
| PARP12 | 6.048 | 17.888 | 2.958 | 0.000653571 |
| PARP14 | 7.261 | 25.702 | 3.540 | 5.17E−06 |
| PARP9 | 18.443 | 66.115 | 3.585 | 1.37E−05 |
| PCSK6 | 3.616 | 0.475 | 0.131 | 1.84E−11 |
| PGLYRP4 | 28.278 | 11.122 | 0.393 | 0.001807447 |
| PHEX | 3.483 | 1.178 | 0.338 | 0.00188494 |
| PI3 | 20386.800 | 6606.973 | 0.324 | 6.87E−06 |
| PLA2G3 | 3.933 | 0.556 | 0.141 | 9.00E−16 |
| PLA2G4B | 7.873 | 3.766 | 0.478 | 0.000902824 |
| PLA2G4D | 1.409 | 0.187 | 0.133 | 5.02E−07 |
| PLBD1 | 78.931 | 26.987 | 0.342 | 0.001063172 |
| PLEKHA4 | 0.531 | 2.175 | 4.098 | 0.004923693 |
| PLXDC2 | 21.965 | 8.362 | 0.381 | 0.00015418 |
| POF1B | 129.287 | 58.641 | 0.454 | 0.001401452 |
| POLR2J3 | 14.311 | 3.087 | 0.216 | 0.00017694 |
| POSTN | 3.548 | 0.767 | 0.216 | 0.001041589 |
| PPAP2C | 5.745 | 1.838 | 0.320 | 0.000432425 |
| PPFIBP2 | 8.574 | 4.602 | 0.537 | 9.00E−05 |
| PPP2R2C | 4.463 | 1.860 | 0.417 | 0.000296121 |
| PRIC285 | 3.781 | 14.161 | 3.745 | 0.006690084 |
| PRSS3 | 11.472 | 2.912 | 0.254 | 1.17E−09 |
| PSAPL1 | 1.218 | 0.077 | 0.063 | 7.33E−16 |
| PSORS1C2 | 4.636 | 1.892 | 0.408 | 0.000746804 |
| PYDC1 | 5.163 | 0.582 | 0.113 | 8.50E−08 |
| RDH12 | 60.584 | 12.719 | 0.210 | 2.35E−05 |

TABLE 1-continued

Transcriptomic analysis of genes differentially expressed after SPINK7-silencing compared to control in differentiated EPC2 cells

| Gene_ID | RPKM Control | RPKM SPINK7 | Fold Change | p-value |
|---|---|---|---|---|
| RGMA | 0.731 | 2.055 | 2.813 | 0.000957165 |
| RNF213 | 3.149 | 10.248 | 3.255 | 0.000151269 |
| RPTN | 152.773 | 23.960 | 0.157 | 7.91E−08 |
| RSAD2 | 14.663 | 51.466 | 3.510 | 0.000657584 |
| S100A4 | 10.952 | 1.743 | 0.159 | 0.000169518 |
| SAMD9L | 3.282 | 8.296 | 2.528 | 0.000122563 |
| SAPCD2 | 1.359 | 5.105 | 3.756 | 5.74E−06 |
| SCCPDH | 1.377 | 0.470 | 0.342 | 0.001095738 |
| SDR9C7 | 23.268 | 3.506 | 0.151 | 2.74E−14 |
| SEMA3B | 0.466 | 2.348 | 5.042 | 5.20E−08 |
| SERPINA12 | 17.941 | 0.441 | 0.025 | 1.41E−19 |
| SERPINB10 | 1.707 | 0.303 | 0.177 | 0.002079277 |
| SERPINB11 | 1.196 | 0.043 | 0.036 | 0.000254419 |
| SERPINB12 | 14.375 | 0.628 | 0.044 | 7.75E−25 |
| SERPINB4 | 2.135 | 1.017 | 0.476 | 0.003011842 |
| SH3GL3 | 2.644 | 0.436 | 0.165 | 9.30E−05 |
| SHF | 5.075 | 1.551 | 0.306 | 0.000279762 |
| SHISA4 | 0.777 | 2.518 | 3.240 | 0.00214213 |
| SHISA9 | 1.303 | 0.520 | 0.399 | 0.002362574 |
| SIPA1L2 | 4.620 | 1.891 | 0.409 | 5.71E−08 |
| SLC10A6 | 3.110 | 1.231 | 0.396 | 0.000694286 |
| SLC15A1 | 3.903 | 0.804 | 0.206 | 6.66E−12 |
| SLC15A3 | 0.553 | 3.453 | 6.245 | 7.80E−06 |
| SLC39A2 | 15.331 | 4.958 | 0.323 | 9.55E−06 |
| SLURP1 | 395.306 | 106.847 | 0.270 | 3.63E−08 |
| SP100 | 16.667 | 45.318 | 2.719 | 0.003767804 |
| SPINK5 | 1307.389 | 256.405 | 0.196 | 2.76E−06 |
| SPINK7 | 601.815 | 48.483 | 0.081 | 1.42E−20 |
| SPRR1A | 1630.121 | 731.475 | 0.449 | 0.000117351 |
| SPRR2B | 701.221 | 368.342 | 0.525 | 0.000175788 |
| SPRY1 | 1.568 | 0.796 | 0.507 | 0.003023006 |
| SPTLC3 | 21.596 | 10.087 | 0.467 | 1.76E−07 |
| SPTSSB | 14.270 | 0.145 | 0.010 | 3.44E−12 |
| STAT1 | 40.731 | 165.908 | 4.073 | 4.60E−05 |
| SYNGR1 | 1.143 | 0.467 | 0.408 | 0.009279141 |
| SYTL2 | 2.970 | 6.445 | 2.170 | 0.000346622 |
| SYTL5 | 1.017 | 0.137 | 0.135 | 0.000953611 |
| TAGLN | 16.779 | 45.100 | 2.688 | 0.000663656 |
| TCN1 | 22.208 | 3.108 | 0.140 | 5.41E−08 |
| TEX101 | 1.478 | 0.153 | 0.104 | 0.005571691 |
| TGM2 | 1.362 | 5.369 | 3.941 | 0.001837368 |
| TGM5 | 4.919 | 0.874 | 0.178 | 1.55E−14 |
| THEM5 | 4.333 | 0.239 | 0.055 | 2.54E−11 |
| TMEM45B | 45.839 | 18.799 | 0.410 | 0.002362663 |
| TMPRSS11B | 71.841 | 5.468 | 0.076 | 0.003055064 |
| TMPRSS11D | 14.631 | 2.846 | 0.195 | 0.000188995 |
| TPRG1 | 6.638 | 2.232 | 0.336 | 9.13E−05 |
| TRANK1 | 0.742 | 3.210 | 4.324 | 0.000934694 |
| TREX2 | 1.424 | 0.410 | 0.288 | 0.000733089 |
| TRIM25 | 12.867 | 33.370 | 2.593 | 0.000104414 |
| UPK3BL | 114.888 | 21.787 | 0.190 | 7.78E−06 |
| USP18 | 1.610 | 10.015 | 6.221 | 8.46E−06 |
| VSIG8 | 22.682 | 6.366 | 0.281 | 1.91E−05 |
| WDR76 | 0.161 | 1.464 | 9.072 | 0.004154222 |
| WFDC5 | 52.581 | 22.585 | 0.430 | 0.000134007 |
| WNT9A | 0.234 | 1.039 | 4.450 | 0.00437511 |
| XAF1 | 6.888 | 31.901 | 4.632 | 2.34E−07 |
| XKRX | 6.464 | 2.415 | 0.374 | 6.86E−05 |
| ZBTB7C | 1.037 | 0.120 | 0.115 | 1.91E−06 |
| ZNF433 | 1.908 | 0.447 | 0.234 | 0.000604875 |
| ZNF556 | 4.679 | 0.794 | 0.170 | 2.88E−05 |
| ZNF626 | 1.118 | 0.363 | 0.324 | 0.001935167 |
| ZNF662 | 1.556 | 0.164 | 0.105 | 4.66E−18 |

FPKM, fold-change (FC) and p-values of genes differentially expressed after SPINK7 gene silencing as compared to NSC in EPC2 cells differentiated at ALI cultures for 14 days identified by RNA sequencing (Fold change > 2, p < 0.05, FPKM > 1).

Furthermore, genes expression of EPC2 monolayer culture (day 0 of ALI culture) and differentiated EPC2 cells in ALI culture (Day 14 of differentiation) were compared. This analysis revealed 3225 differentially expressed genes (p<0.05, fold change>2, RPKM>1) (data not shown). The majority of SPINK7 modified genes (77%) were also differentially expressed during differentiation, including a regulator of terminal epidermal differentiation calmodulin-like 5 (CALML5), and the cornified envelope components expressed by differentiated keratinocytes such as FLG and LOR (data not shown) (Sun, B. K. et al. Genes & development 29, 2225-2230 (2015)). Importantly, the top genes which were overexpressed during differentiation were down-regulated after SPINK7 silencing. This indicated that loss of SPINK7 promoted transcriptional changes that resulted in an undifferentiated epithelial phenotype.

Figure 3A:
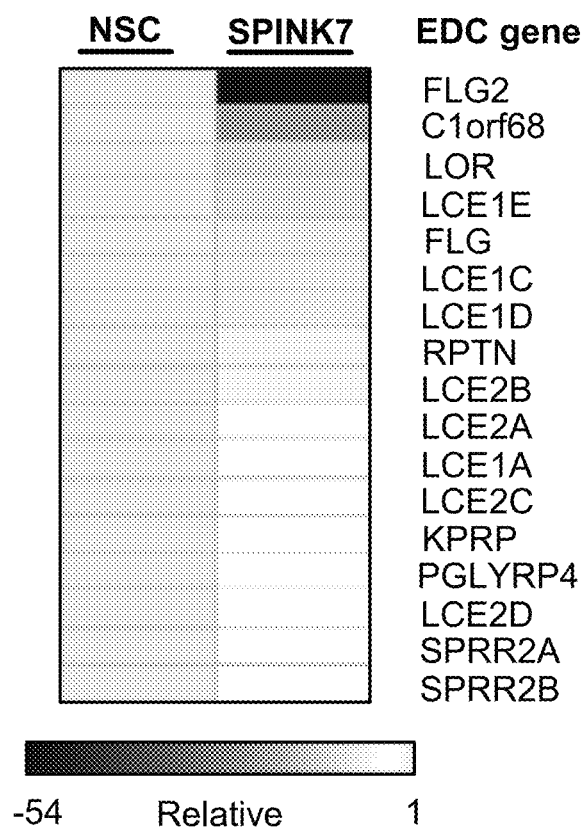
FIG. 3A-C.
Figure 3B:
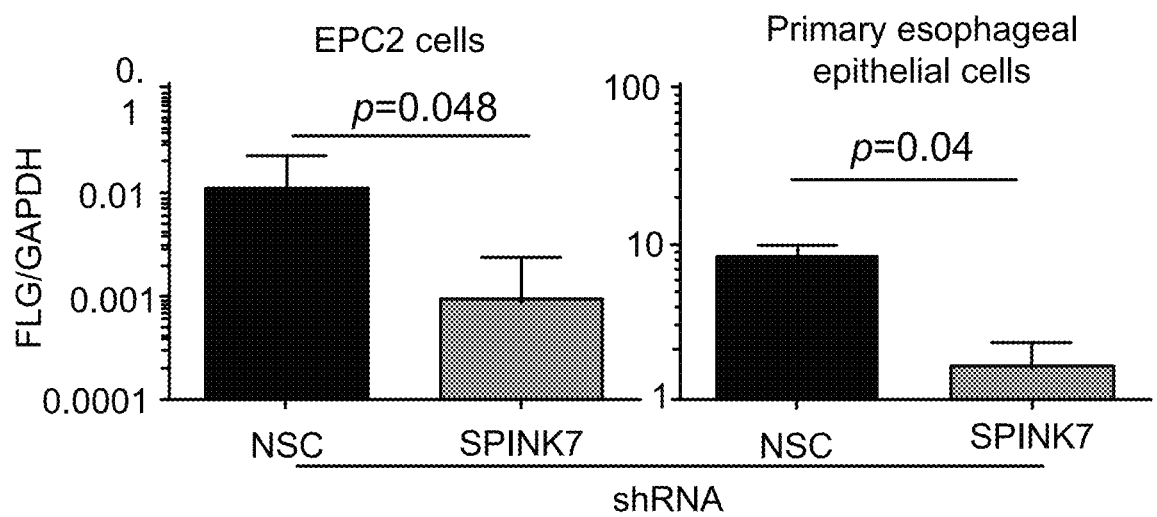
Figure 3C:
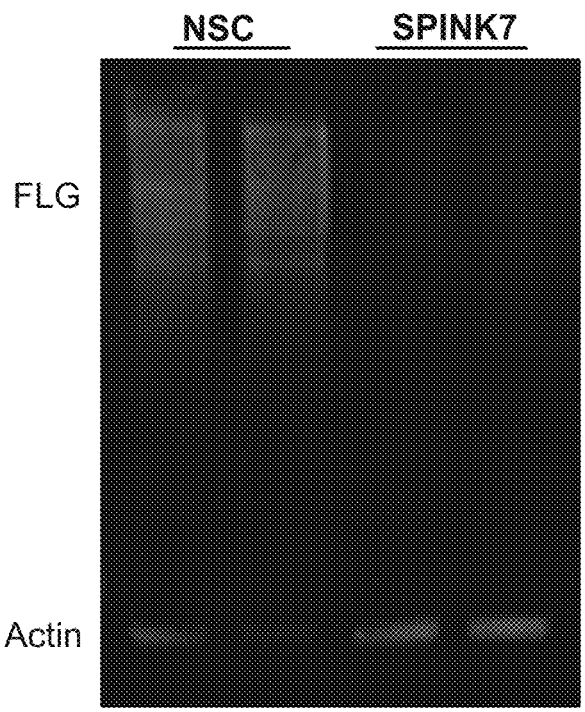

Focusing on the epidermal differentiation complex (EDC) locus on 1q21, the locus with the greatest change in expression in the EoE transcriptome, the genes altered by SPINK7 silencing and the EDC genes were intersected (Blanchard, C. et al. Journal of immunology 184, 4033-4041 (2010)). Of the 54 EDC genes expressed by differentiated epithelial cells (RPKM>1), 17 genes were significantly down-regulated by STINK7 loss (FIG. 3A). SPINK7 silencing resulted in a marked decrease in filaggrin mRNA (FIG. 3B) and protein expression as shown by western blot and immunofluorescence analyses (FIG. 3C) analyses. Notably, the expression of SPINK7 and FLG correlated in EoE patients (n=133) (data not shown).

Venn diagrams depicting the number of genes differentially expressed (<2-fold, p<0.05, FPKM>1) in SPINK7 gene silencing as compared to NSC in EPC2 cells differentiated ALI cultures for 14 days (SPINK7-269 genes) and in EPC2 cells following ALI differentiation (day 14 of culture) compared to prior ALI differentiation (day 7 of culture) (Terminal differentiation-678 genes) (data not shown) or in EPC2 cells following ALI differentiation (day 14 of culture) compared cells in monolayer (day 0) (differentiation-3225 genes) (data not shown). Genes overlapping between these two data sets were identified. The top 14 genes with the highest decrease in expression are presented. Ten epidermal differentiation complex (EDC) genes were significantly (p<0.05) altered by SPINK7 depletion in EPC2 cells following ALI differentiation (day 14). FLG mRNA expression in NSC or SPINK7-depleted EPC2 cells following ALI differentiation (data not shown; data represented as the mean±Sd from three independent experiments performed in triplicates). Correlation of normalized FLG and normalized SPINK7 expression in esophageal biopsies of 170 patients with active EoE was also performed (data not shown).

Example 4: SPINK7 Regulation is Upstream of SPINK5 in Esophageal Cells

Figure 4A:
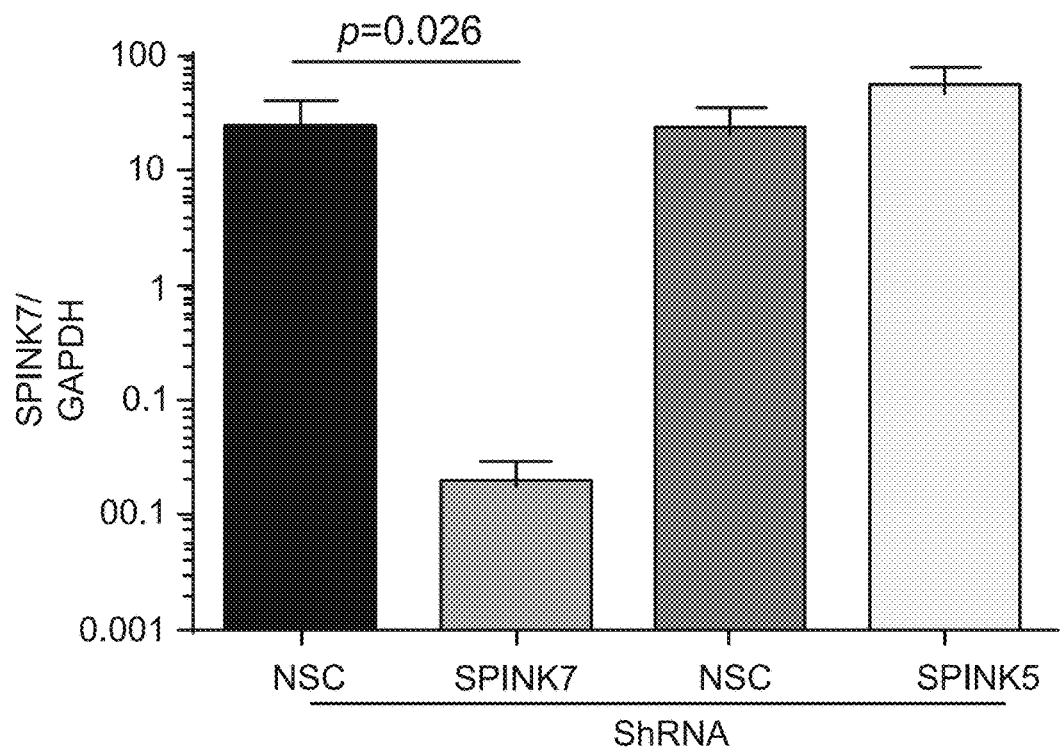
FIGS. 4A and 4B are bar graphs showing qPCR analysis of SPINK7 expression (FIG. 4A), or SPINK5 expression (FIG. 4B) of control (NSC), SPINK7-depleted and SPINK5-depleted EPC2 cells that were grown for 14 days in ALI culture.
Figure 4B:
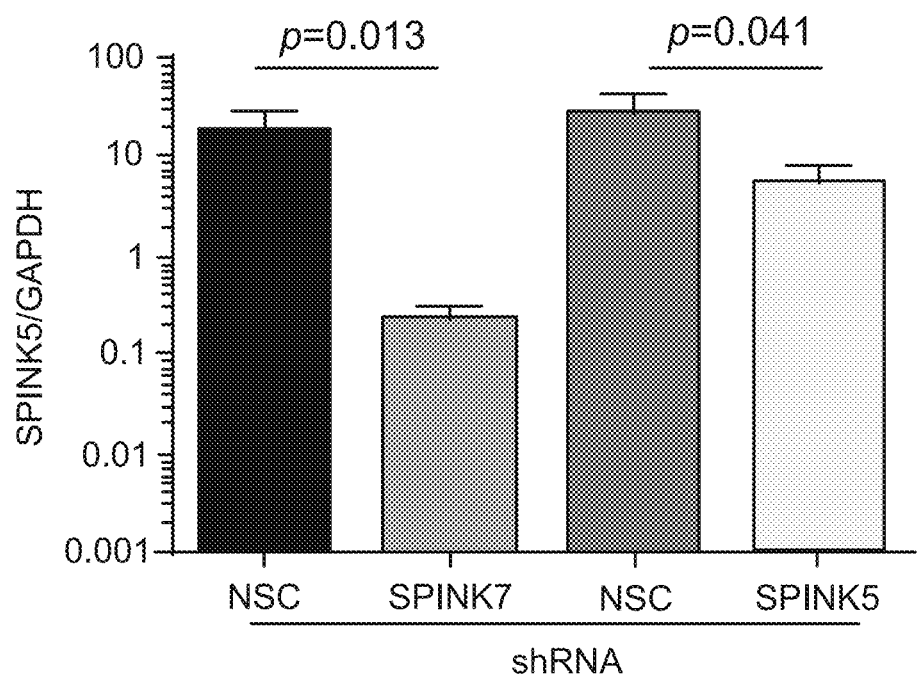

Having identified SPINK5 as part of the epithelial differentiation program (FIG. 2), the impact of SPINK7 silencing on SPINK5 expression was examined. In contrast to the absence of the effect of SPINK7 downregulation on SPINK5 mRNA level in undifferentiated EPC2 cells, SPINK7 silencing markedly reduced the expression of SPINK5 mRNA following ALI differentiation (88-fold decrease; FIG. 4B). In contrast, SPINK5 silencing did not affect SPINK7 expression (FIG. 4A). These data suggest that loss of SPINK7 expression may be upstream of loss of SPINK5.

Example 5: Silencing of SPINK7 Results in Transcriptional Changes that Overlap with the EoE and IL-13-Associated Transcriptomes The impact of loss of SPINK7 on the EoE transcriptome, the abnormal transcriptional profile of the esophagus of EoE patients was analyzed. The genes modified by SPINK7 silencing in differentiated cells were intersected with the EoE transcriptome and a substantial overlap of 36% was found (data not shown). These genes were enriched for abnormal skin inflammation, skin physiology, skin development and innate immune response (FIG. 5A) including major histocompatibility complex (MHC) genes, FLG, interferon induced with helicase C domain 1 (IFIH1) and IL36RN (data not shown).

Because it had been demonstrated that EoE pathogenesis is mediated at least in part by an IL-13-stimulated keratinocyte-derived transcriptome (Blanchard, C. et al. *The Journal of allergy and clinical immunology* 120, 1292-1300 (2007), and Kc, K., Rothenberg, et al *PloS one* 10, e0127755 (2015)), the genes modified by SPINK7 silencing were intersected with the genes modified by IL-13-treatment in EPC2 cells following ALI differentiation based on genome-wide RNA sequencing data (Kc, K., Rothenberg, et al *PloS one* 10, e0127755 (2015)). One hundred nineteen genes overlapped between these two transcript profiles (data not shown). These genes were enriched for abnormal skin including keratosis and acantholysis, skin development and differentiation as well as innate immunity (data not shown).

Analysis of the localization of these proteins revealed significant enrichment in the cornified envelope (data not shown). Further, 48% of the overlapping genes between SPINK7-regulated transcripts and EoE transcriptome were regulated by IL-13 (FIG. 5B), indicating that SPINK7 interplays between the two pathways although IL-13 did not down-regulated SPINK7 (data not shown).

A Venn diagram was made depicting the number of genes differentially expressed in EoE patients as compared to control (<2-fold, p<0.05, FPKM>1) (EoE-1607 genes) and in SPINK7 gene silencing as compared to NSC in EPC2 cells differentiated ALI cultures for 14 days (SPINK7-269 genes) identified by RNA sequencing (data not shown). Genes overlapping between these two data sets were identified (86 genes). A heatmap of the overlap gene is presented according to their fold changed expression after SPINK7 silencing as compared to control (SPINK7) and fold changed expression in EoE as compared to control. A Venn diagram was made depicting the number of genes differentially expressed by EPC2 cells following ALI differentiation after IL-13 stimulation compared to untreated cells (<2-fold, p<0.05, FPKM>1) (EoE-1161 genes) and in SPINK7 gene silencing as compared to NSC in EPC2 cells differentiated ALI cultures for 14 days (SPINK7-269 genes) identified by RNA sequencing. Genes overlapping between these two data sets were identified (80 genes) (data not shown). A Venn diagram was made depicting the number of genes that overlap between EoE and SPINK7 silencing (EoE/SPINK7-86 genes) and the number of genes that overlap between IL-13 trigger and SPINK7 silencing (IL-13/SPINK7-80 genes) (data not shown). Genes overlapping between these two data sets were identified (41 genes).

Example 6: Loss of SPINK7 Induces Epithelial Architecture

Figure 6A:
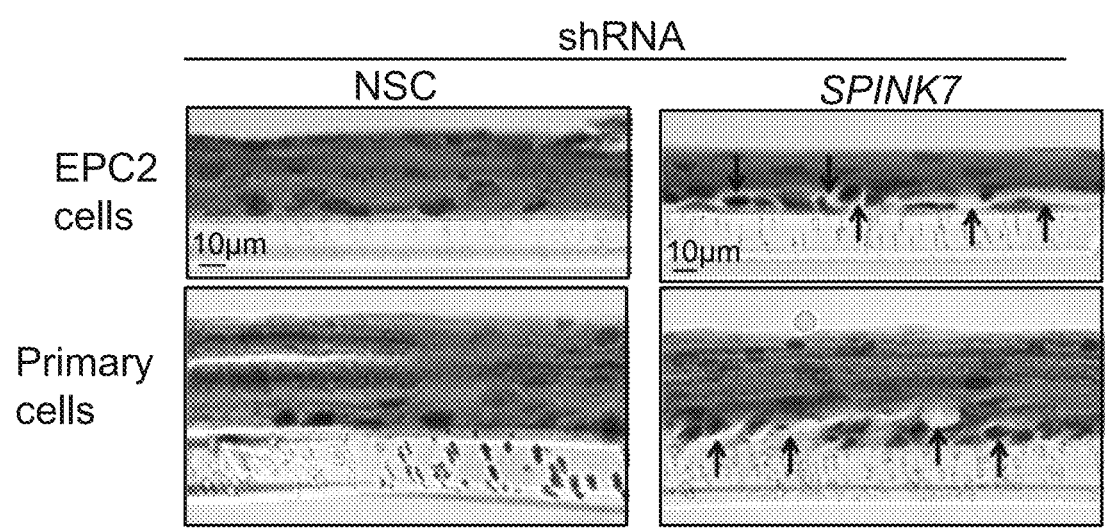
FIGS. 6A-6C show that loss of SPINK7 impairs epithelial architecture and epithelial barrier function.

SPINK7 silencing resulted in dilated intercellular spaces compared with NSC treated cells after ALI differentiation (day 14) (see arrows in FIG. 6A). Analysis of the non-associated areas revealed that SPINK7-depleted ALI cultures had a 3-fold increase (p=0.0002) in the non-cell associated tissue area compared with NSC ALI cultures (data not shown). Quantitative analyses was performed of H&E sections from NSC or SPINK7-depleted EPC2 cells following ALI differentiation and were presented as the mean volume of tissue area per a high power field minus the non-cell associate areas that were formed inside the tissues, per a high power field (data not shown), the percent of non-cell associate areas in the tissues measured as the ratio between the non-cell associate areas per high power filed and the total tissue area per a high power field.

As a control, morphometric analysis of the total area of the differentiated ALI cultures was not altered after SPINK7 silencing compared to NSC (data not shown), the percent of non-cell associate areas in the tissues measured as the ratio between the non-cell associate areas per a high power filed and the total tissue area per a high power field. Data are representative of three experiments performed in triplicate and are represented as the mean±Sd. Quantitative analysis of H&E-stained sections was performed of NSC or SPINK7-depleted EPC2 cells grown for 7, 9 and 11 days in the ALI cultures (data not shown). The percent of non-cell associate areas in the tissues was quantified from three experiments performed in triplicate and are represented as the mean±Sd.

Figure 6B:
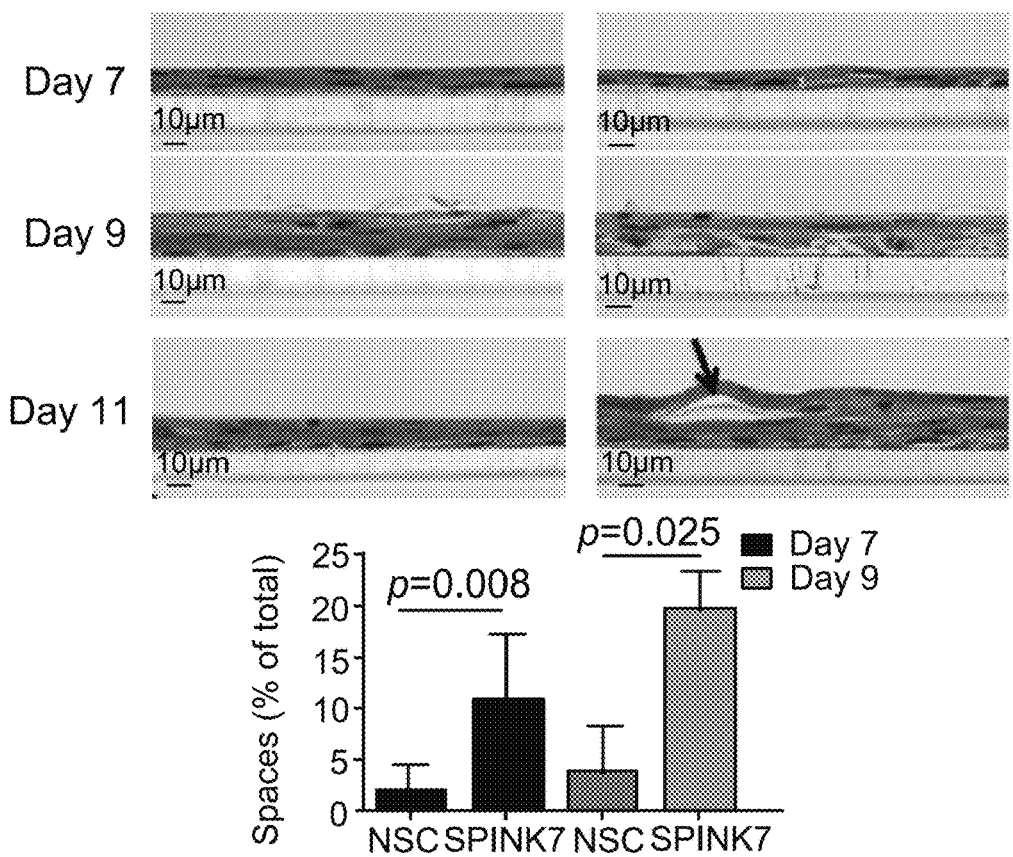
Figure 6C:
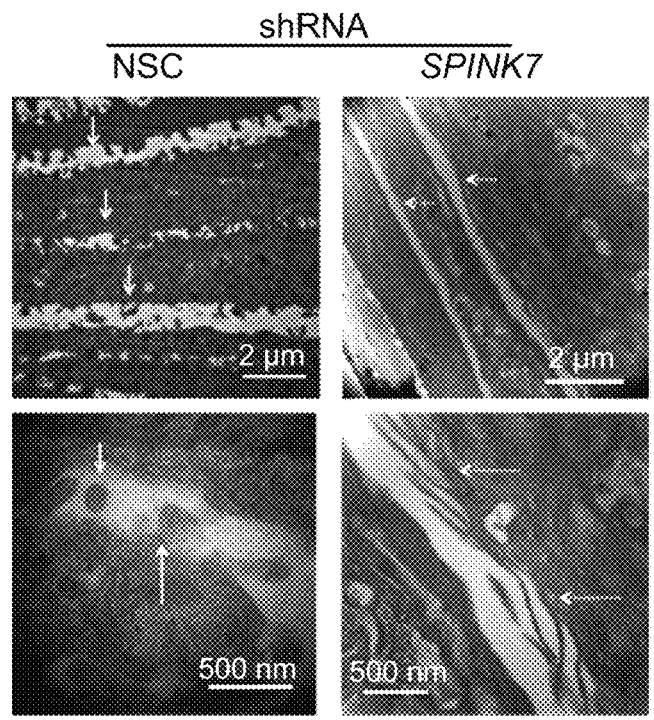

At baseline (day 7), SPINK7 silencing increased non-cellular spaces by 5.4-fold (p=0.008) compared to NSC control cells that were densely packed (FIG. 6B). The same finding was observed in SPINK7-silenced cells at day 9 (5.4-fold, p=0.025) (FIG. 6B). Notably, by 11-14 days, blebbing of the squamous layers was seen following SPINK7 silencing (see arrow in FIG. 6B). Transmission electron microscopy revealed that the microplicae, intercellular ridges and finger like projections between cells that were readily apparent in the NSC cells were nearly absent from SPINK7-silenced cells (FIG. 6C)

Example 7: SPINK7 Silencing Results in Alterations of Junctional Proteins

Figure 7:
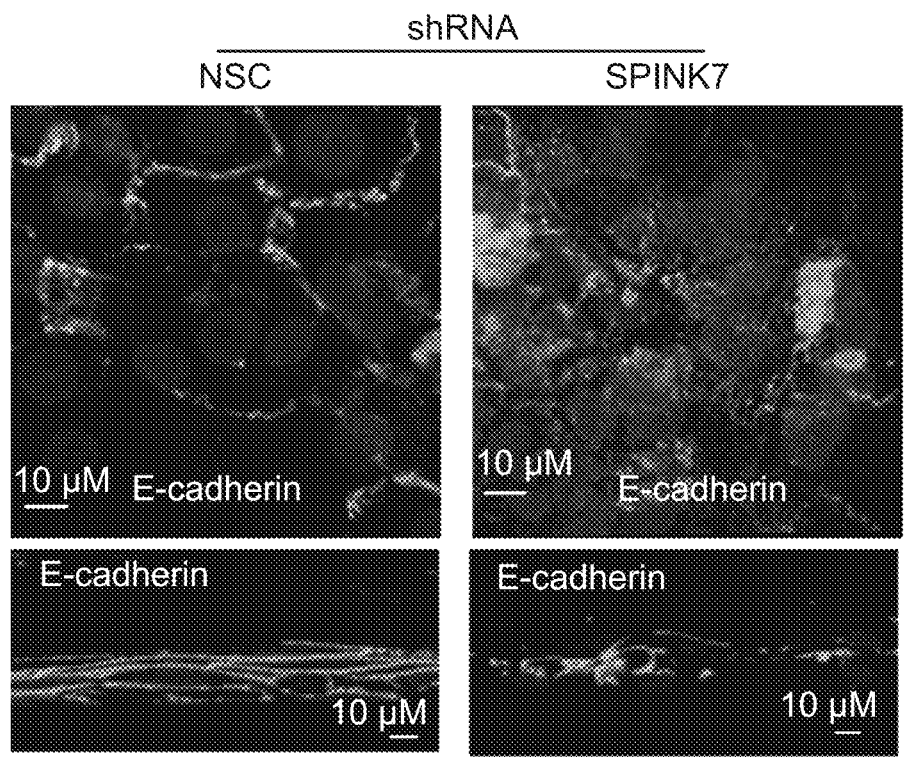
FIG. 7 shows immunostained sections of E-cadherin and DAPI of NSC or SPINK7-depleted EPC2 cells grown with high $Ca_{2+}$ or following 14 days of ALI differentiations (bottom).

Immunofluorescence analysis of submerged as well as ALI cultures of EPC2 cells revealed that E-cadherin localized to the cellular membrane and showed an organized pattern of cellular junctions (FIG. 7). The localization of β-catenin, the E-cadherin effector, was adjacent to the cells membranes (data not shown). Following SPINK7 silencing, E-cadherin was diffusely present within cells and the cellular membrane, and the staining was often found in aggregates. β-catenin was partially localized to the cytoplasm and partially remained localized in cell periphery (FIG. 7).

Immunofluorescence analysis of DSG1 expression in ALI cultures of control cells revealed membrane localization. In contrast, after SPINK7 silencing, DSG1 expression was decreased and abnormally localized in the cytoplasm (data not shown).

Example 8: SPINK7 Silencing Induced IBF

Figure 8:
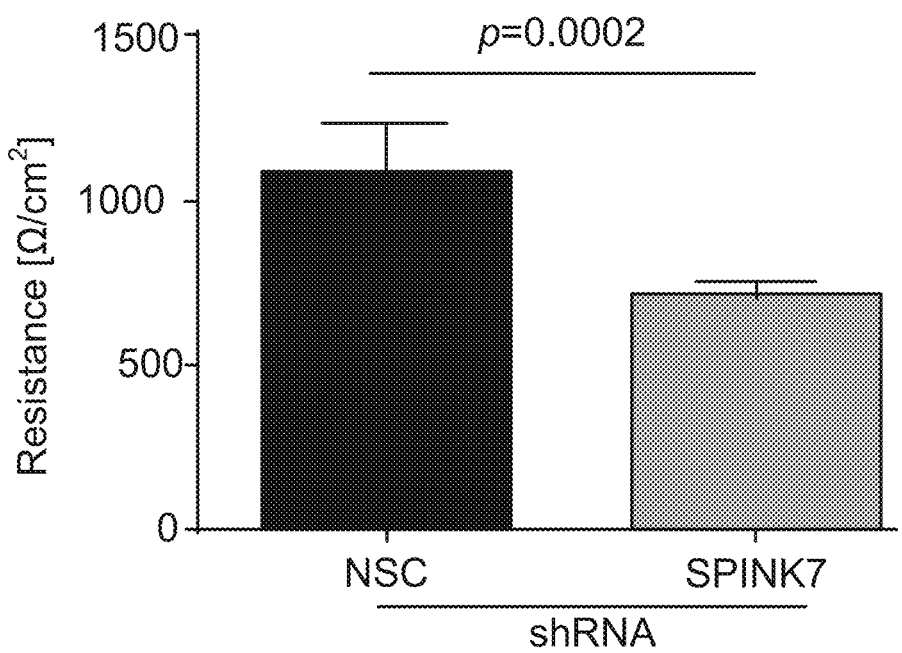
FIG. 8 shows transepithelial electrical resistance ($\Omega$) was measure from NSC and SPINK7-depleted EPC2 cells at day 7 of ALI differentiation.

Paracellular and transcellular permeability of the ALI cultured cells were analyzed. Transepithelial electrical resistance (TEER) was reduced by 36% during ALI differentiation of SPINK7-depleted cells compared to NSC cells (FIG. 8). Transepithelial electrical resistance (Ω) was measured from NSC and SPINK7-depleted EPC2 cells measured at day 7 and 8 during ALI differentiation (data not shown; data were representative of four experiments performed in triplicate and are represented as the mean±Sd). These data reveal that down regulation of SPINK7 expression was sufficient to induce IBF.

Example 9: SPINK7 Gene Silencing Unleashes the Production of Pro-Inflammatory Cytokines The supernatant of SPINK7 silenced cells was analyzed using a multiplex cytokine array. Amongst 64 cytokines, a marked change in 18 cytokines (FIG. 9A) was observed. Amongst the changes, IL-8 was increased by 12-fold (p=0.03) in the SPINK7-depleted cells compared to NSC cells (FIG. 9A); and this was verified by ELISA and qPCR analyses (data not shown). Interestingly, there was a negative correlation between SPINK7 and IL-8 mRNA expression in a cohort of 133 EoE patients (p=0.014; data not shown), supporting the inverse relationship between SPINK7 and IL-8.

In addition, IL-8 expression increased in EoE patients compared to controls (data not shown) (Persad, R. et al. *Journal of pediatric gastroenterology and nutrition* 55, 251-260 (2012), and Blanchard, C. et al. *The Journal of allergy and clinical immunology* 127, 208-217, 217 e201-207 (2011)). IL-8 release was blocked by cyclosporine A (CsA) and FK506 (FIG. 9B), suggesting that the increase cytokine release is mediated through NFAT activation. Indeed, NFATC1 was translocated to the nucleus after SPINK7 silencing compared to NSC cells (data not shown).

Multiplex cytokine array analysis of the supernatant of SPINK7 silenced cells and controls that were treated with CsA revealed that CsA partially blocked the release of several cytokines including eotaxin-1 and IL-16 while other cytokines such as G-CSF and IL-15 remained unaffected (data not shown). Notably, CsA did not affect the proteolytic activity or the barrier function (data not shown). Consistent with these findings, human eosinophils showed increased chemotaxis towards supernatants derived from SPINK7-silenced cells as compared to supernatants derived from NSC cells or media alone (data not shown).

Figure 9A:
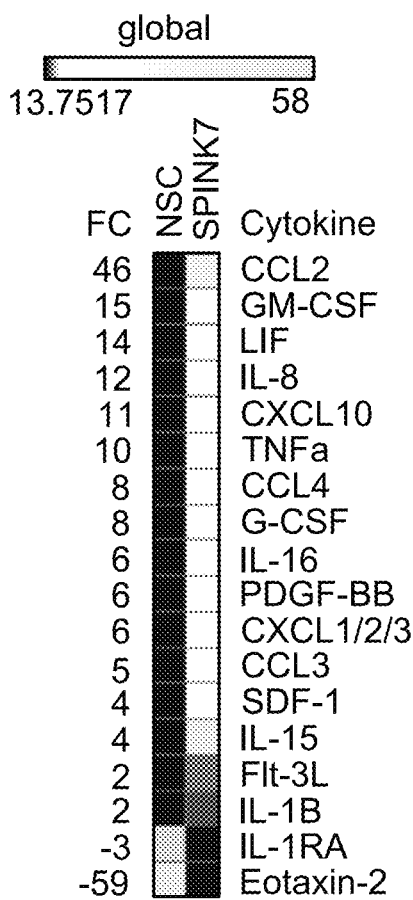
FIGS. 9A-9C show that the loss of SPINK7 induces cytokine expression and release.
Figure 9B:
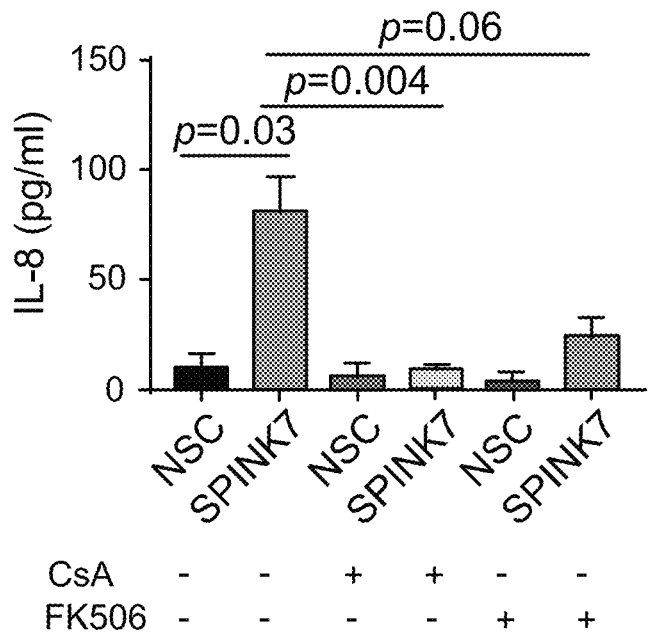

FIG. 9A shows a heatmap of cytokine and chemokine expression derived from supernatants of NSC or SPINK7-depleted EPC2 cells following ALI differentiation (day 14) that were altered Con>1 pg/mL, −2>Fold Change (FC)>2, P<0.05) after SPINK7-depletion as compared to NSC. Data presented as the mean of two independent experiments performed in quadrats. IL-8 protein expression in supernatants (data not shown) and mRNA expression from NSC or SPINK7-depleted EPC2 cells following ALI differentiation (day 14) was performed. Data represented as the mean±Sd from three independent experiments performed in triplicates. TSLP protein expression in supernatants from NSC or SPINK7-depleted EPC2 cells following ALI differentiation was performed (data not shown).

Example 10: Impact of SPINK7 Silencing on Serine Proteinases

Figure 10A:
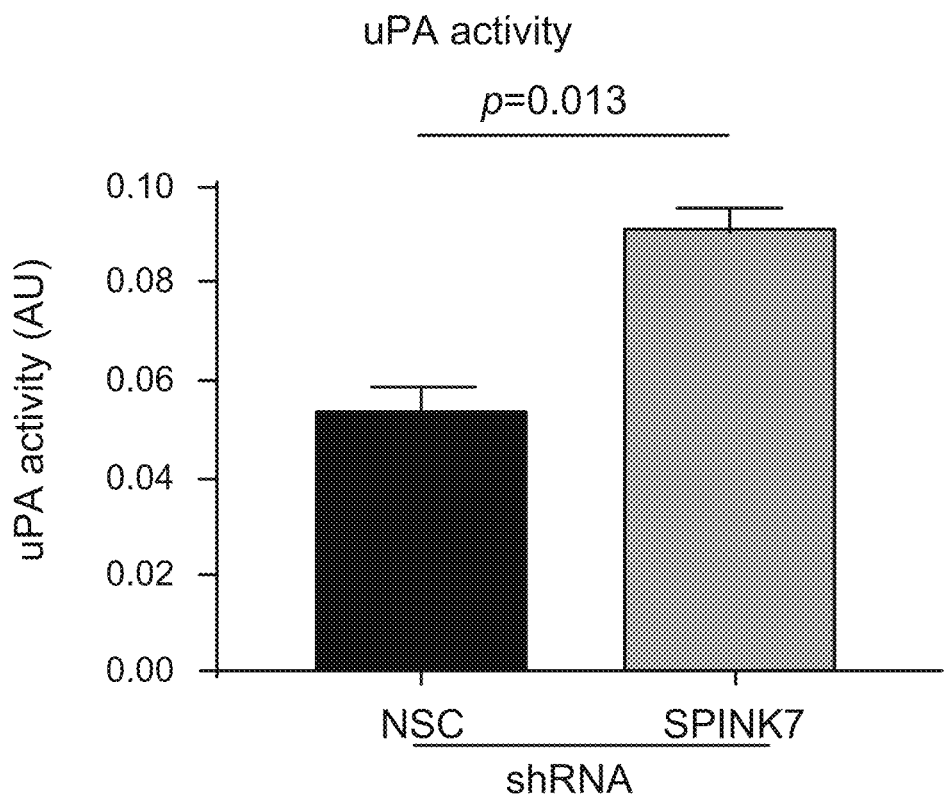
FIGS. 10A-10E show that A1AT administration reverses the aggravated inflamed mucosa and impaired barrier in SPINK7-deleted cells and shows evidence that uPA/uPAR is involved in human EoE.

The known SPINK7 target uPA (Cheng, X., Lu, S. H. & Cui, Y. *Cancer letters* 290, 87-95 (2010), and Huang, G. et al. *Carcinogenesis* 28, 2274-2281(2007)) was analyzed. Consistent with previous reports, SPINK7 directly inhibited uPA proteolytic activity (data not shown) (Cui, Y., et al *International journal of oncology* 37, 1521-1528 (2010)). In addition, supernatants from cells during differentiation revealed a 1.8-fold increase in released uPA activity after SPINK7 silencing (p=0.013) (FIG. 10A). An increased proteolytic activity using the broad trypsin-like activity substrate Val-Pro-Arg (FIG. 10B) was observed.

Figure 10B:
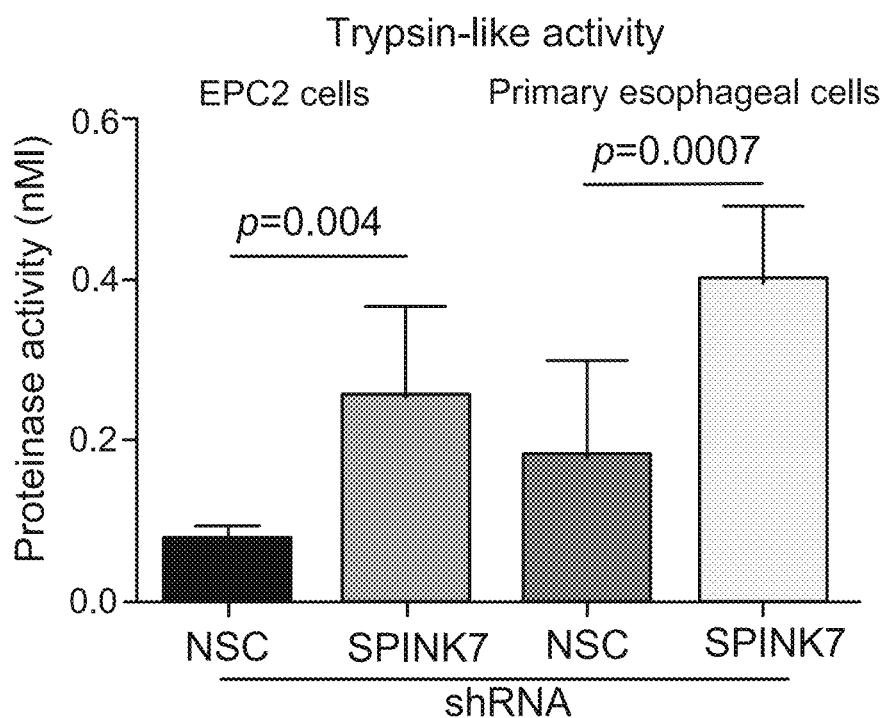
Figure 10C:
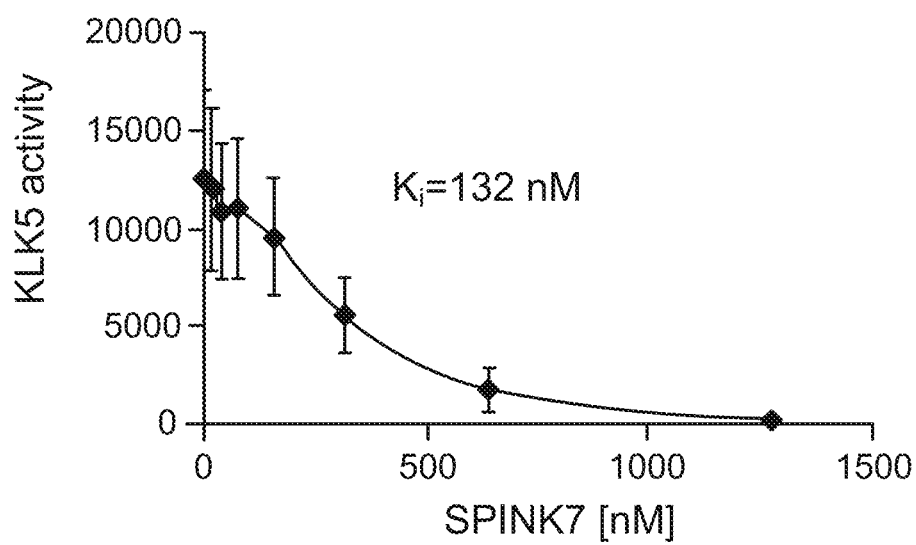
Figure 10D:
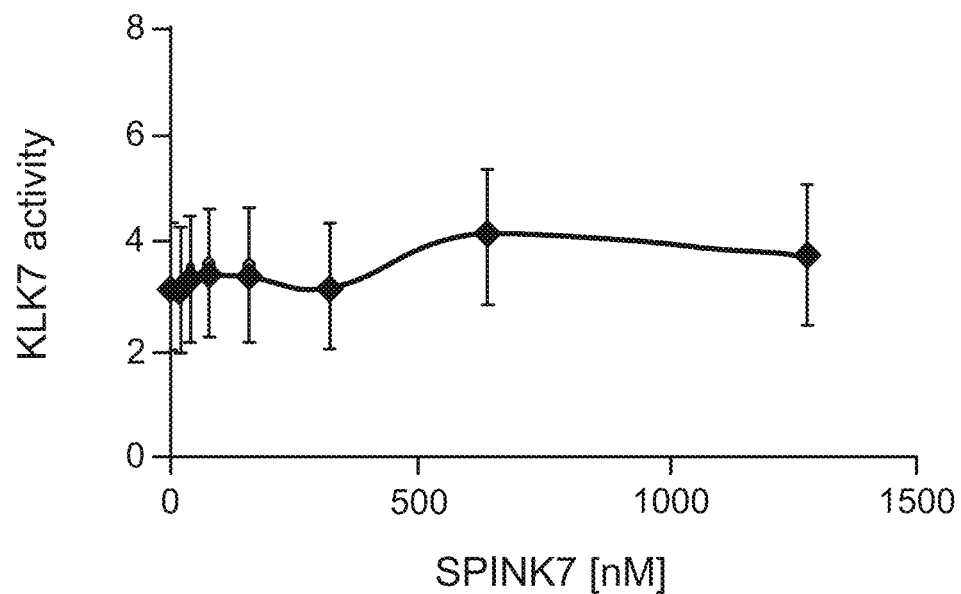
Figure 10E:
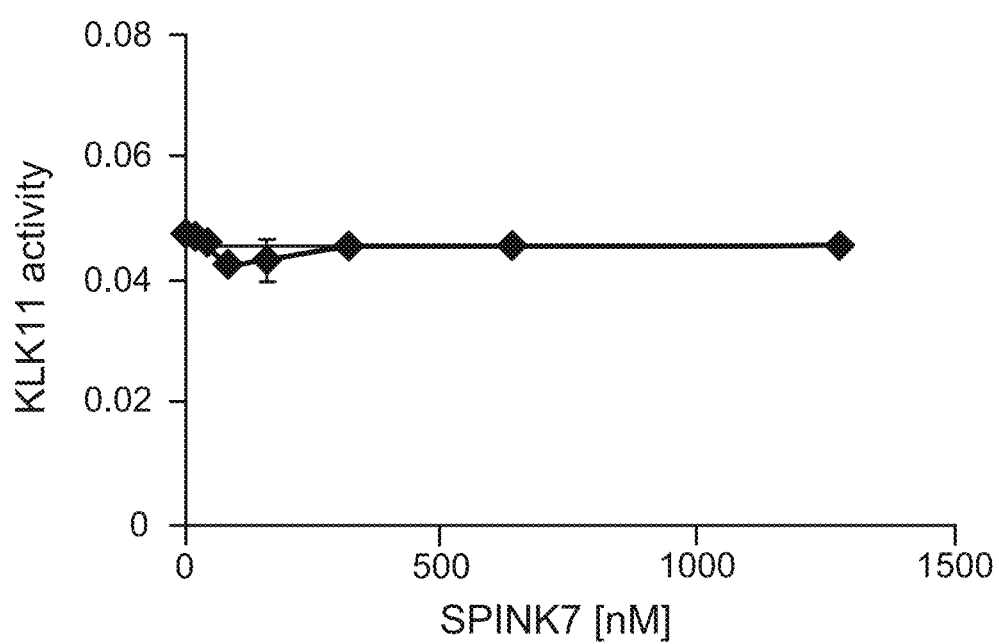

Given that most members of the KLK family have trypsin-like activity, the ability of SPINK7 to directly inhibit members from this family in vitro was tested. SPINK7 inhibited KLK5 proteolytic activity in a dose-dependent manner with a mean $K_i$ of 132±108 nM (mean±SD) (FIG. 10C) but did not inhibit KLK7 and KLK11 (FIGS. 10D and). SPINK7 silencing did not increase proteinase protein expression (data not shown) indicating that the unleashed proteinase activity was simply related to loss of proteolytic inhibition. Collectively, these data indicated that SPINK7 directly inhibits serine proteinases including uPA and KLK5, while SPINK7 gene silencing results in increase proteolytic activity of uPA and KLKs.

qPCR analysis was performed of SPINK7 and SPINK5 expression of control (NSC) or SPINK7-depleted EPC2 cells that were grown in a monolayer or differentiated in ALI culture (data not shown). Panel B shows quantification of uPA activity in supernatants derived from (NSC) or SPINK7-depleted EPC2 cells following ALI differentiation. Data are representative of three experiments performed in triplicate and are represented as the mean±Sd. FIG. 12G shows quantification of the activity of serine proteinases with trypsin-like activity in supernatants derived from (NSC) or SPINK7-depleted EPC2 cells following ALI differentiation. Data are representative of four experiments performed in triplicate and are represented as the mean±Sd. FIGS. 10A and 10B show in vitro activity assays of KLK5, KLK7 and KLK11 in the presence of the indicated concentrations of SPINK7. Data are representative of three experiments and are represented as the mean±s.e.m.

Example 11: Gene Silencing of SPINK7 Results in Alteration in Adherens Proteins and Desmosomal Proteins Followed by Impaired Epithelial Barrier Confocal microscopic analysis of high resolution 3D structures of differentiated cells revealed that DSG1 and E-cadherin staining was limited to membranes in the superficial regions of the NSC cells and demonstrated close association between the cells. In contrast, there was marked separation after SPINK7 silencing (data not shown).

Figure 11A:
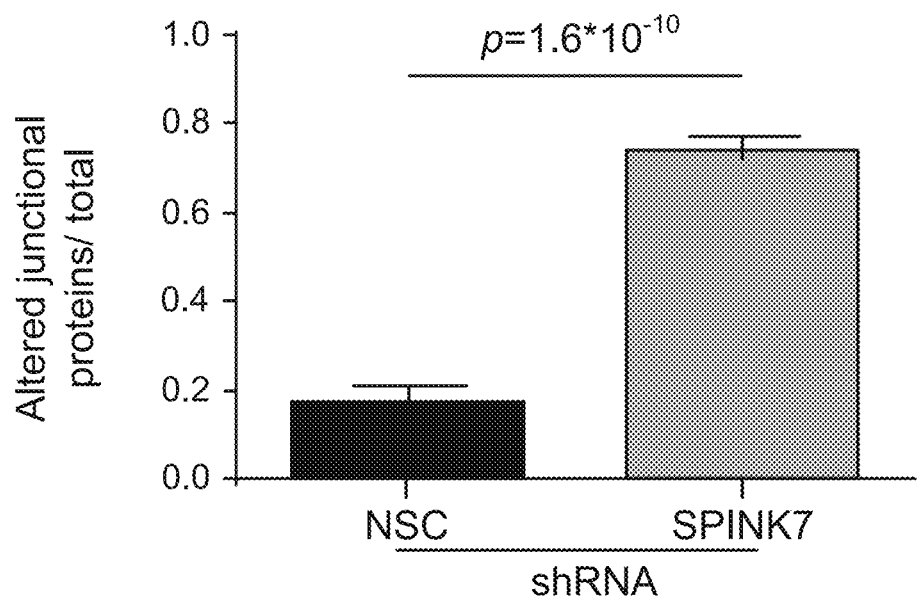
FIGS. 11A and 11B show that loss of SPINK7 impairs epithelial architecture and epithelial barrier function.
Figure 11B:
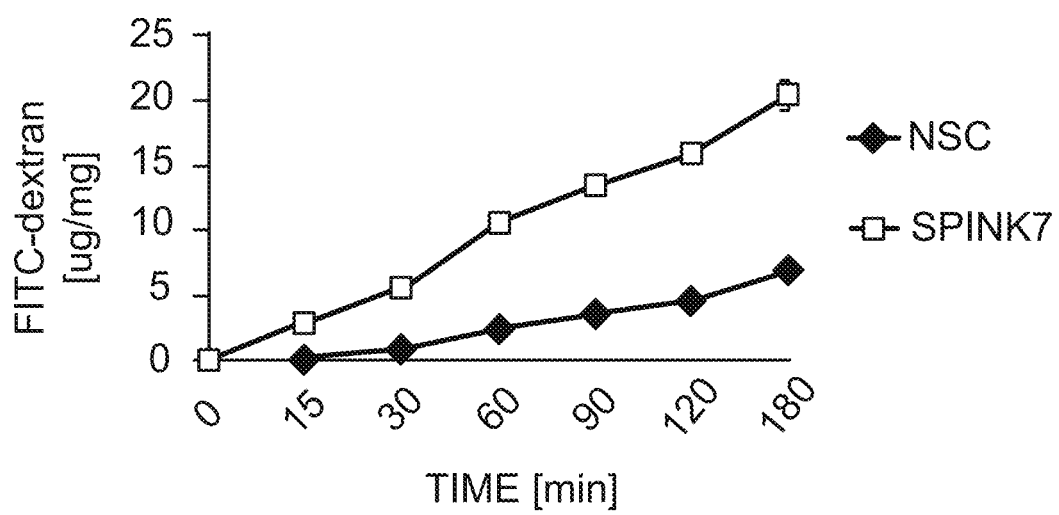

FIG. 11A shows quantitative analysis of cells demonstrating alterations of junctional proteins from the total cells from NSC or SPINK7-depleted EPC2 cells following ALI differentiation. Data are representative of four experiments performed in triplicate and are represented as the mean±Sd. FIG. 11B shows FITC-dextran flux measured at day 14 of ALI differentiation from NSC and SPINK7-depleted EPC2 cells for the indicated time points. Analysis of the transcellular permeability by measuring the flux of macromolecules (FITC-dextran) was significantly increased in SPINK7 shRNA-transduced cells compared to NSC cells and reached 2.9-fold increase (FIG. 11B).

Example 12: uPA in the Esophagus of EoE Patients

Figure 12A:
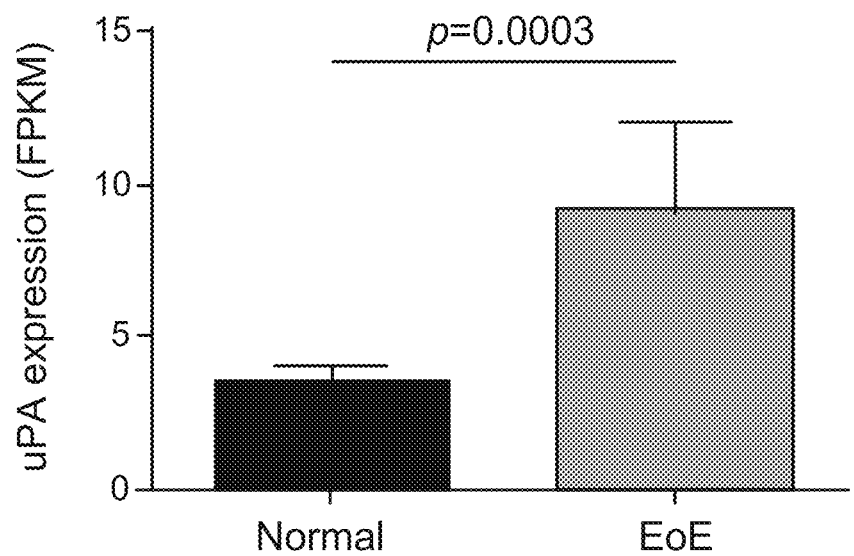
FIGS. 12A-12G show that A1AT administration reverses the aggravated inflamed mucosa and impaired barrier in SPINK7-deleted cells and shows evidence that uPA/uPAR is involved in human EoE.
Figure 12B:
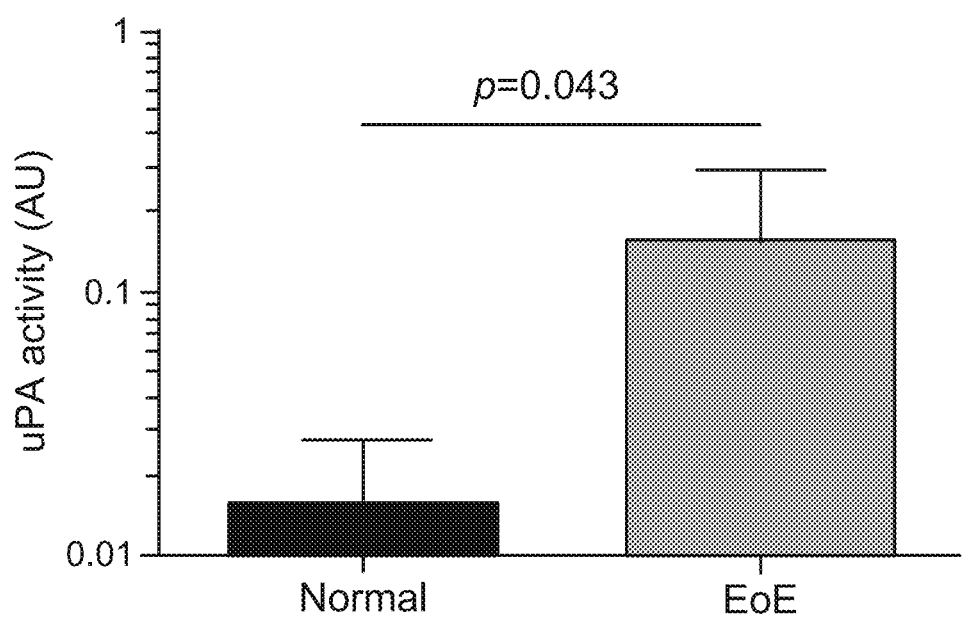
Figure 12C:
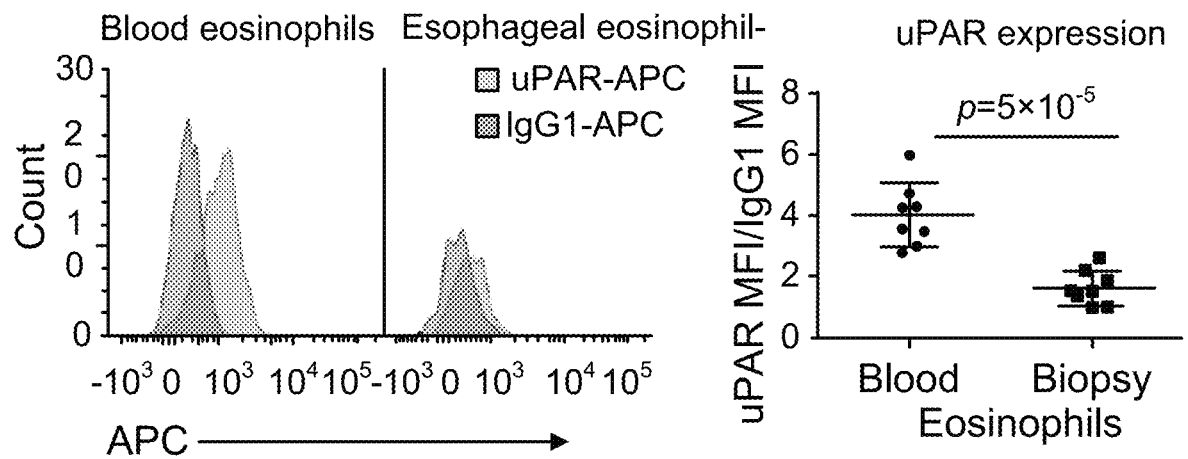

In esophageal biopsies from EoE patients, uPA mRNA expression was increased (2.7-fold; p=0.0003) and uPA activity increased by 10-fold (p=0.043) compared with control individuals (FIGS. 12A and 12B). Notably, the pan proteinase activity was not altered in EoE biopsies compared to controls (data not shown), indicating that the increased proteolytic activity observed in EoE patients was accounted by a subset of proteinases. Interestingly, uPAR expression was induced after SPINK7 silencing (data not shown). Collectively, the results provide evidence that SPINK7 mediates its function by regulating the uPA axis.

It is notable that allergic inflammatory cells including eosinophils express both uPAR and its known ligands β1 integrins (Brooks, A. M. et al. *American journal of respiratory cell and molecular biology* 35, 503-51 (2006)). In support of the involvement of this pathway in eosinophils migration, uPAR expression by esophageal eosinophils was found to be markedly decreased in the biopsies of EoE patients compared with blood eosinophils, as defined by FACS (p=5×10$^{-5}$) (FIG. 12C) (Johansson, M. W. & Mosher, D. F. *American journal of respiratory cell and molecular biology* 45, 889-897 (2011)).

Figure 12D:
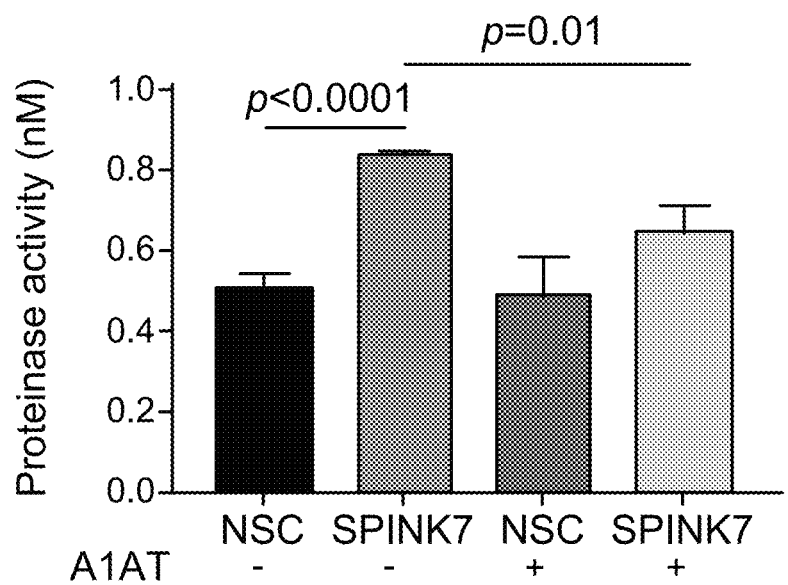

It was hypothesized that inhibition of uncontrolled proteolytic activity would ameliorate the impaired barrier and the loss of epithelial differentiation elicited by the loss of SPINK7. The serine proteinase inhibitor, al anti-trypsin (A1AT) has potential clinical benefit with a good safety profile in humans (Lewis, E. C. Molecular medicine 18, 957-970 (2012)). Administration of A1AT to the cells inhibited the trypsin-like activity of supernatant of SPINK7 silenced cells (FIG. 12D).

Figure 12E:
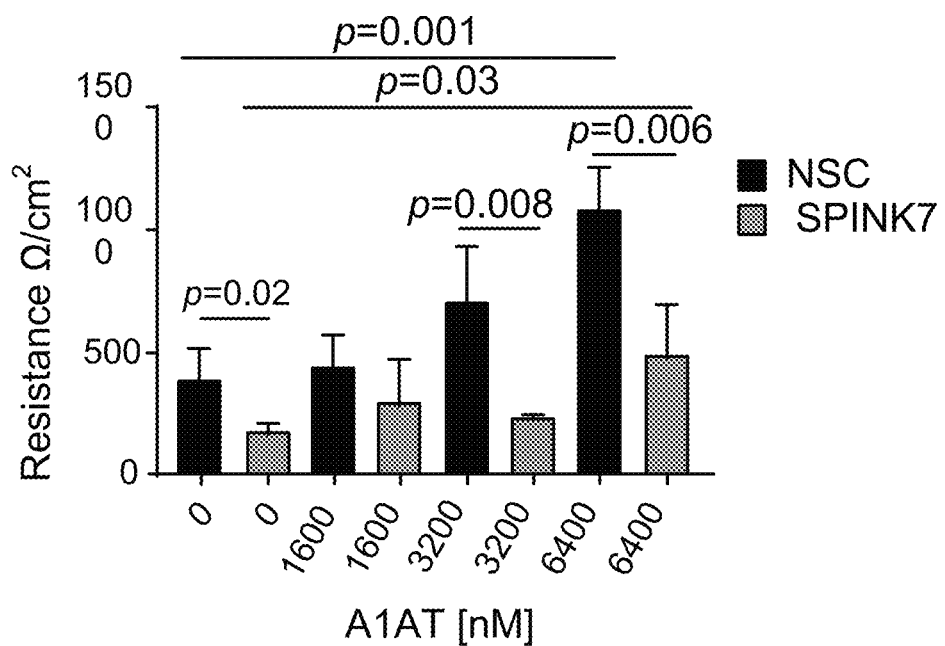
Figure 12F:
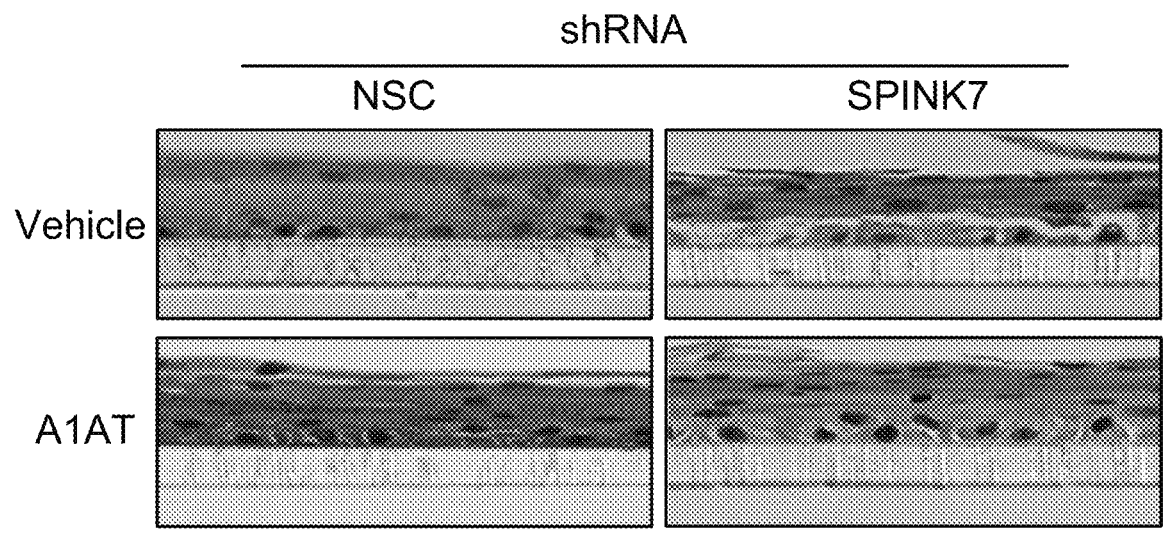
Figure 12G:
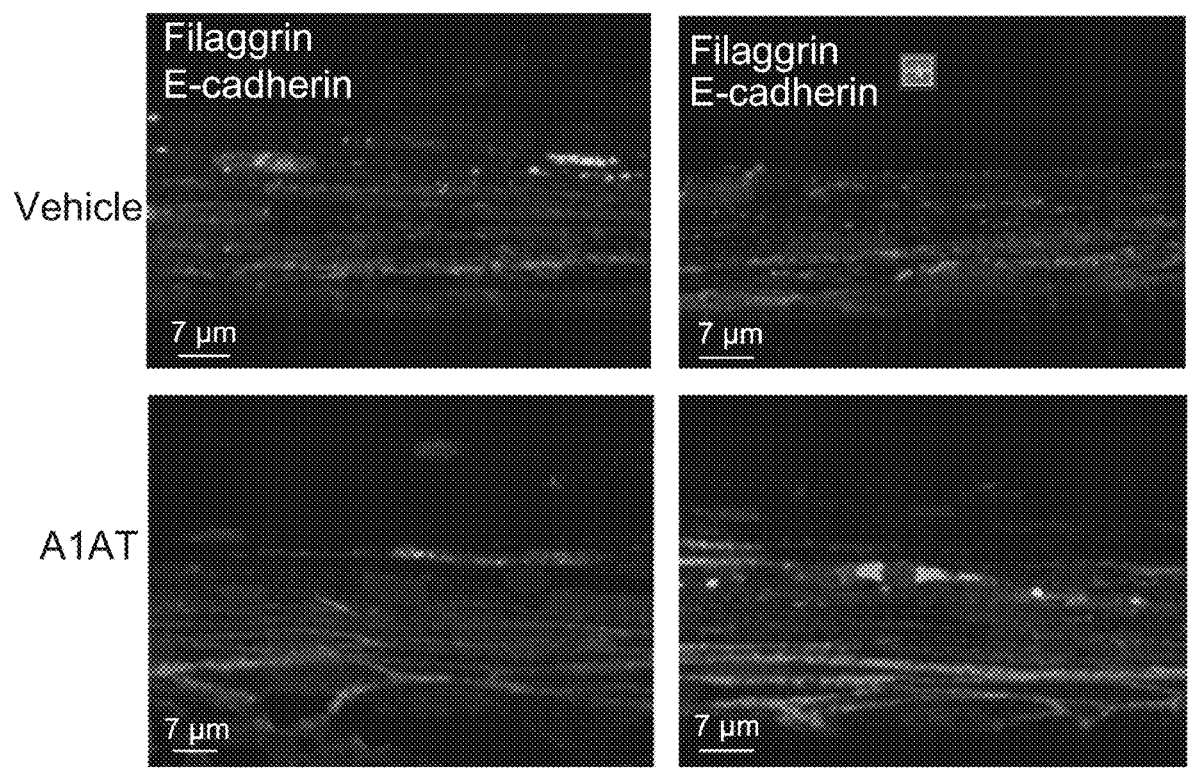
Figure 13:
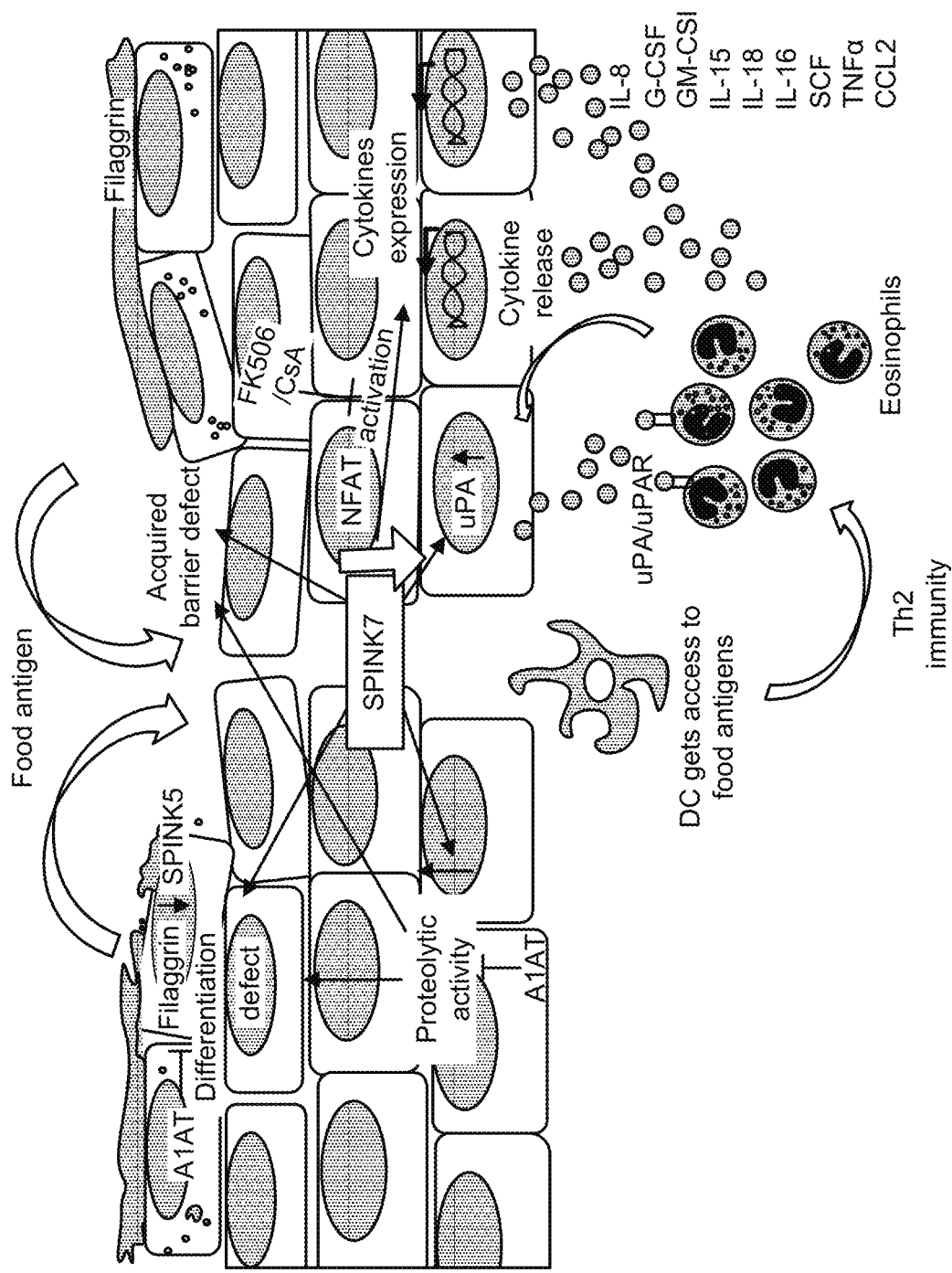

To extend the potential benefit of A1AT, its ability to restore the epithelial changes induced by SPINK7 loss was ability. Of note, A1AT demonstrated a dose-dependent ability to improve barrier function (FIG. 12E) and epithelial integrity as demonstrated by the decreased inter-cellular spaces (FIG. 12F). Consistent with these findings, A1AT administration increased filaggrin expression (FIG. 12G)

An analysis of single nucleotide polymorphism (SNP) of 700 EoE patients as compared to 412 non-atopic non-EoE controls was performed. The results revealed significant genetic interaction between TSLP and PLAU (encoding for uPA) in EoE patients (data not shown). Further analysis showed a genetic interaction between the TSLP, PLAU and SPINK locus. FIG. 12C shows the expression of uPAR on the cell surface eosinophils derived from blood or esophageal biopsies from 8 EoE patients. FIG. 12A shows uPA FPKM values in esophageal samples from normal and EoE patients. FIG. 12B shows analysis of the uPA proteolytic activity in esophageal biopsies from normal and EoE patients.

Example 13: Genetic Epistasis Between SPINK7 and ILRL1 (ST2)

To independently prove association between SPINK7 and the pathophysiology of allergic inflammation the contribution of genetic variation of SPINK7 to EoE susceptibility was determined. The genomic coordinates of SNPs in SPINK7 genomic region were intersected with a large collection of functional genomics datasets according to ENCODE data. Based on that analysis three SNPs (i.e. rs2400509, rs3749690, rs12521065) were chosen in the SPINK7 gene region that were likely to influence gene regulatory mechanisms. These SNPs were genotyped in the SPINK7 gene region in an EoE (n=501) and non-EoE allergic control cohort (n=610; data not shown). Logistic regression analysis did not reveal association with EoE susceptibility (data not shown), consistent with the recent GWAS which did not reveal association at the SPINK loci (Kottyan, L. C. et al. *Nature genetics* 46, 895-900 (2014)).

SPINK7 contributed to EoE susceptibility by interacting with other genes. As such, genetic epistasis between these SNPs and atopy-associated genes (n=79) using a custom high density SNP chip platform was identified. Analysis of EoE cases versus non-EoE allergic controls revealed significant genetic interaction between SPINK7 and genetic variants encoding for TH2-associated molecules including ST2, IL-17A, TGFβ1, TGFBR1 and epithelial genes SPRRA1 and PDE4B (data not shown). Stratified logistic regression analyses revealed that SPINK7 (rs2400509) and ST2 (rs4988958) strongly interacted (p=0.0004). Having the SPINK7 major allele in association with the minor allele of ST2 increased the risk for EoE compared to SPINK7 and ST2 minor alleles (OR 1.96; p-value<0.01) (data not shown). Analysis of EoE probability indicated that the direction of the effect for ST2 differs based on the presence of the SPINK7 allele (data not shown).

Example 14: Genetic Data Links the SPINK7 Downstream Target-uPA to EoE

TSLP, located at 5q22, is an established EoE-associated genetic locus (Sherrill, J. D. et al. *The Journal of allergy and clinical immunology* 126, 160-165 e163, (2010)). Logistic regression analysis between TSLP and atopy-associated genes on the SNP chip was performed. The most substantial SNPs that interacted with TSLP were three PLAU variants (rs2459449, rs2227551, rs2227564; p<0.0001 for each; data not shown). To understand this interaction, TSLP stratified logistic regression analyses was performed for these three PLAU variants and it was found that having the TSLP risk variant in association with the minor allele in PLAU was protective (OR 0.68-0.71; p-value range 0.011-0.004) while in those who did not have the risk variant, the minor allele in PLAU was associated with an increased risk of EoE (OR 1.99-2.10; p value range 0.0004-0.0003) (data not shown).

Example 15: Effect of Organic Compounds on KLK5 Activity

Two organic compounds were tested for their inhibition of KLK5. Compound I (3-(3-chlorophenyl)carboxy-7-hydroxymethyl coumarin) had an IC$_{50}$ value of 52±12 µM (FIGS. 14A and 14B). Compound II (3-carboxy-7-hydroxymethyl coumarin) had an IC$_{50}$ value of 83±8 nM (14C and 14D). Compound I and II were non reversible inhibitors.

Discussion

Figure 5A:
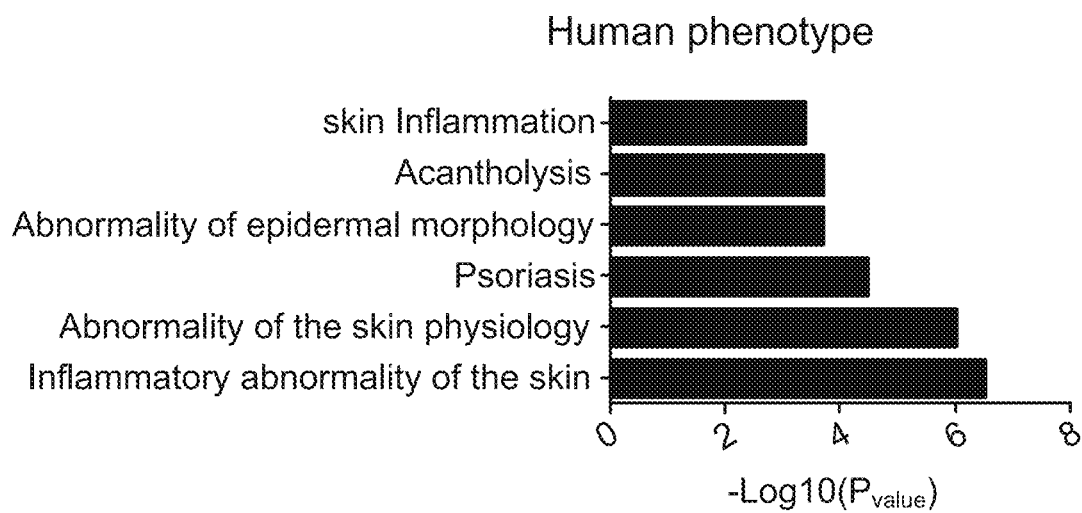
FIGS. 5A and 5B show that loss of SPINK7 induces inflamed esophageal mucosa transcriptome.
Figure 5B:
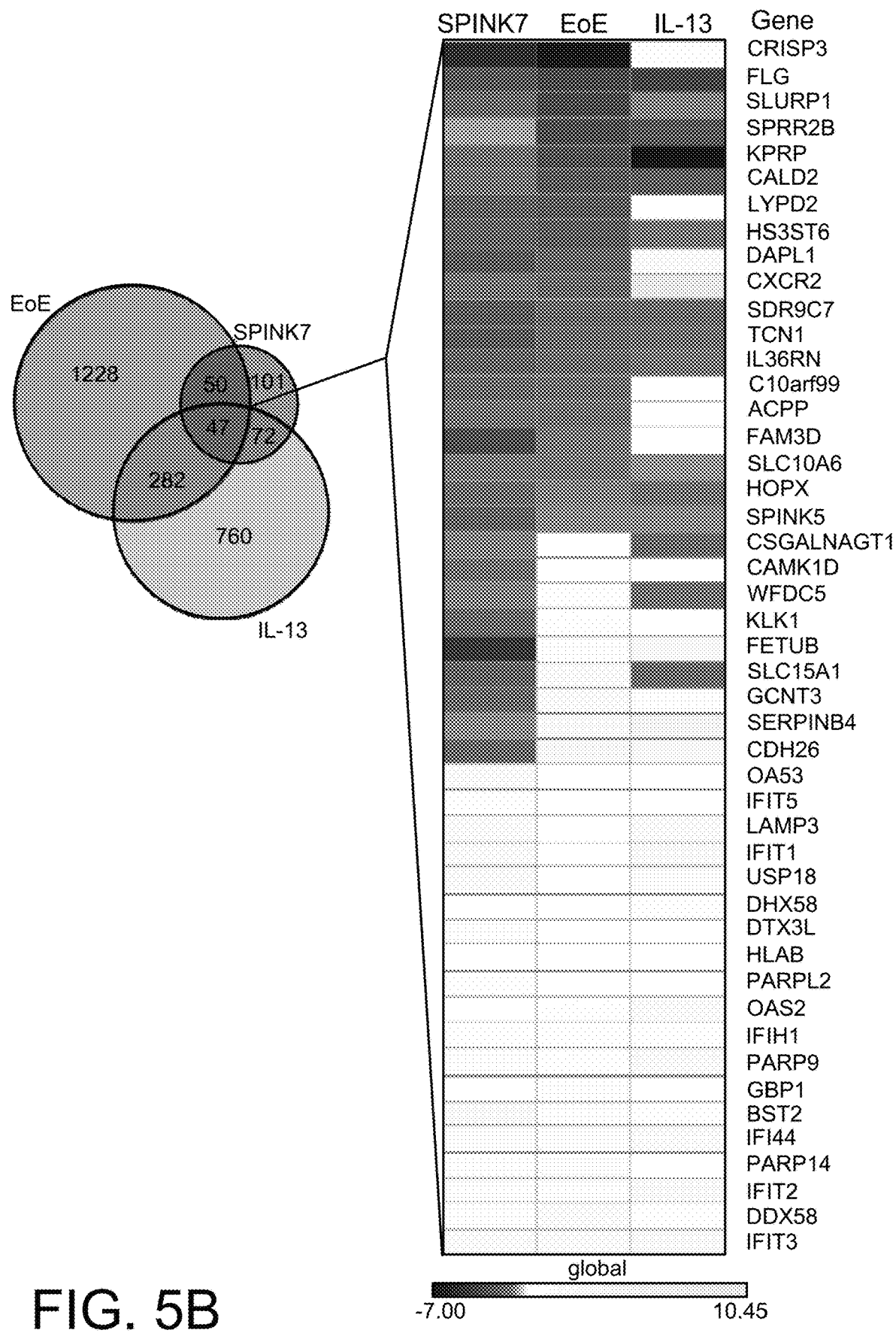
Figure 9C:
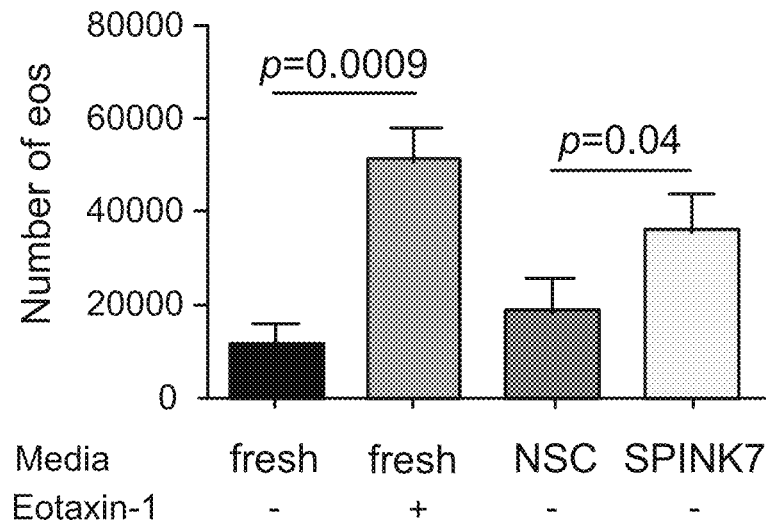

The data presented herein identify a role for the naturally occurring serine proteinase inhibitor SPINK7 as a key non-redundant checkpoint in regulating epithelial homeostatic responses in the esophagus (Summarized in FIG. 8). Multiple lines of evidence are presented showing that loss of SPINK7 is sufficient for induction of pro-inflammatory responses including:

(1) loss of barrier integrity including formation of dilated intercellular spaces (FIGS. 6A and 6B), absence of microplicae (FIG. 6C), increased paracellular permeability and reduced TEER (FIGS. 8A and 11B);

(2) epithelial acantholysis including disruption of the adherens junction proteins E-cadherin, β-catenin and DSG1 (FIG. 7);

(3) defective epithelial cell differentiation highlighted by loss of FLG expression (FIGS. 3A-3C and 4A and 4B);

(4) nuclear mobilization of NFATC1 and over-production of pro-inflammatory cytokines (FIGS. 9A-9C); and (5) induction of an innate transcript signature that overlaps with that associated with allergic inflammation (FIGS. 5A and 5B).

The known SPINK7 target uPA was identified as a mediator of the pathogenic events downstream from the loss of SPINK7 by demonstrating that uPA activity increased in the esophagus of EoE patients compared to control individuals, that uPA receptor was modulated in the esophagus, and that SPINK7 was an inhibitor of uPA, consistent with prior reports.

In addition, KLK5 was identified as a novel and direct target of SPINK7. These findings are stipulated by identifying genetic epistasis between SPINK7 and PLAU with two genes that are cardinal for Th2 immunity (i.e. ST2 and TSLP respectively; data not shown).

The relative importance of SPINK7 in the context of EoE, was demonstrated by its relative deficiency in EoE versus control individuals and its high expression in normal esophagus. Indeed, analysis of esophageal specific genes in the protein atlas revealed that SPINK7 was an esophageal enriched gene (Uhlen, M. et al. *Proteomics. Science* 347, 1260419 (2015)). Evidence is provided that loss of SPINK7 may be upstream from loss of SPINK5, which is undoubtedly contributory to the Th2-response, as demonstrated by its rare genetic deficiency (Netherton's syndrome) (Furio, L. et al. *The Journal of experimental medicine* 211, 499-513).

It is notable that SPINK7 was also known as esophageal cancer related gene 2 (ECRG2) as it was been identified as a tumor suppressor by its ability to inhibit the binding of uPA to uPAR and suppress cell migration/invasion and signaling pathways including elevated cytosolic calcium levels (Cheng, X., Lu, S. H. & Cui, Y. *Cancer letters* 290, 87-95 (2010), Huang, G. et al. *Carcinogenesis* 28, 2274-2281 (2007), Cheng, X., et al. *The Journal of biological chemistry* 284, 30897-30906 (2009), Brooks, A. M. et al. *American journal of respiratory cell and molecular biology* 35, 503-51 (2006), and Alfano, M., et al. *Journal of leukocyte biology* 74, 750-756 (2003)). The loss of SPINK7 in esophageal epithelial cells was demonstrated to increase uPA activity and that uPA activity is increased in the esophagus of EoE patients compared to controls (FIGS. 10A and 12B).

The expression of uPAR was markedly reduced in esophageal eosinophils compared to blood eosinophils (FIG. 12C), demonstrating its dynamic regulation during EoE. uPAR is known to be internalized following engagement of uPA: serpin complexes (Nykjaer, A. et al. *The EMBO journal* 16, 2610-2620 (1997)). Therefore, the reduction of uPAR expression on the cell surface of eosinophils represents local uPA hyperactivity. In addition, genetic epistasis between TSLP and PLAU (data not shown) providing independent evidence for the likely contribution of this pathway was demonstrated. These collective data sets indicated that SPINK7 mediated regulation of the uPA/uPAR complex was involved in disease pathogenesis. In addition, SPINK7 was able to specifically inhibit KLK5 in vitro which is remarkable as KLK5 is an upstream proteinase known to cleave and activate most members of the KLK family as well as uPA (Brattsand, M., et al *The Journal of investigative dermatology* 124, 198-203 (2005), Wang, S. et al. *Experimental dermatology* 23, 524-526 (2014), Furio, L. et al. *The Journal of experimental medicine* 211, 499-513, Debela, M. et al. *Biological chemistry* 389, 623-632 (2008), and Prassas, I., et al. *Nature reviews. Drug discovery* 14, 183-202 (2015)).

The possibility that loss of SPINK7 promoted NFAT activation was explored, because TSLP expression in keratinocytes is NFAT-dependent (Wilson, S. R. et al. *Cell* 155, 285-295 (2013)). Indeed, loss of SPINK7 promoted mobilization of NFATC1 to the nucleus and primed esophageal epithelial cells to release several major drivers of adaptive immunity such as GM-CSF, TNFα, and IL-8. The release of some of these cytokines was blocked by inhibiting NFAT activation by CsA and FK506.

Local fluctuations in SPINK7 expression serves a dual role in atopic reaction; firstly, by hampering the epithelial barrier which promote immune cells to encounter luminal antigens and secondly, by priming epithelial cells to secrete pro-allergic and immunomodulatory cytokines.

It has been reported that SPINK7 provides a spindle assembly checkpoint and that loss of SPINK7 results in rapid proliferation and chromosomal instability (Cheng, X., et al *The Journal of biological chemistry* 283, 5888-5898 (2008)). Therefore, the defect in the differentiation process caused by the loss of SPINK7 could be a part of programmed cell response to repair the damaged tissue by increasing the pool of undifferentiated cells with proliferative capacity.

In addition, the loss of SPINK7 caused release of several cytokines (i.e. IL-1β, TNFα and PDGF) that are key regulatory molecules of tissue repair (through uPA/uPAR-dependent mechanism) (Chabot, V. et al. *Stem cell research & therapy* 6, 188 (2015)), IL-8 is known to regulate tissue regeneration by promoting angiogenesis (Stewart, C. E., et al *Thorax* 67, 477-487 (2012)), and Alexander, R. A. et al. *Cardiovascular research* 94, 125-135 (2012)), and is increased in the esophagus of EoE patients (Persad, R. et al. *Journal of pediatric gastroenterology and nutrition* 55, 251-260 (2012) and Blanchard, C. et al. *The Journal of allergy and clinical immunology* 127, 208-217, 217 e201-207 (2011)).

This study identified a hitherto unrecognized pathway centrally mediated by SPINK7 and involving unleashed proteinase activity in allergic esophageal inflammation. Loss of SPINK7 and aberrant regulation of its downstream targets resulted in a defect in epithelial cell differentiation, loss of barrier function, and induction of an innate transcript signature that overlaps with allergic inflammation.

This pathway serves a causative role in compromising epithelial barrier and as an internal signal for epithelial damage with inflammatory consequences. SPINK7 provides a novel checkpoint for regulating a pro-inflammatory response characterized by excessive cytokine production and eosinophil infiltration in the esophagus. In addition, genetic variants in this pathway interact with undoubtedly atopic mechanisms (e.g. TSLP and IL-33/ST2) to initiate and propagate allergic inflammation at least in the esophagus.

Administration of the serine proteinase inhibitor, A1AT, was demonstrated to restore the epithelial impairment, at least in part; such that protein replacement therapy with proteinase inhibitors such as A1AT has therapeutic potential for atopic diseases such as EoE and Netherton's syndrome.

These data provide evidence that proteinases serve an important role in regulating immune response and substantiate the need to pursue therapeutic strategies that modulate relevant immune responses by suppression of uncontrolled proteinases in disease pathophysiology.

What is claimed is:

1. A method of treating an allergic inflammatory condition in a subject in need thereof, the allergic inflammatory condition characterized by inflammation of a squamous epithelium in a target tissue of the subject, the method comprising administering to the subject a pharmaceutical composition comprising a kallikrein 5 (KLK5) inhibitor, and a pharmaceutically acceptable carrier, wherein the target tissue is esophageal tissue and the allergic inflammatory condition is eosinophilic esophagitis (EoE).

2. The method of claim 1, wherein the method comprises administering an amount of the KLK5 inhibitor effective to suppress KLK5 proteinase activity in the target tissue.

3. The method of claim 1, wherein the subject is human.

* * * * *

UNITED STATES PATENT AND TRADEMARK OFFICE
CERTIFICATE OF CORRECTION

| | |
|---|---|
| PATENT NO. | : 11,564,905 B2 |
| APPLICATION NO. | : 16/946984 |
| DATED | : January 31, 2023 |
| INVENTOR(S) | : Nurit P. Azouz et al. |

It is certified that error appears in the above-identified patent and that said Letters Patent is hereby corrected as shown below:

In the Specification

Under the Cross Reference to Related Application Paragraph

Column 1, please add:
-- GOVERNMENT SUPPORT CLAUSE
This invention was made with Government support under contract AI070235 awarded by the National Institutes of Health. The Government has certain rights in the invention. --

Signed and Sealed this
Third Day of December, 2024

*Katherine Kelly Vidal*

Katherine Kelly Vidal
*Director of the United States Patent and Trademark Office*